(12) United States Patent
Vignali et al.

(10) Patent No.: US 9,198,806 B2
(45) Date of Patent: *Dec. 1, 2015

(54) CONTAINMENT PANT

(71) Applicant: Kimberly-Clark Worldwide, Inc., Neenah, WI (US)

(72) Inventors: Frederique Vignali, Appleton, WI (US); Kevin Leon LaBerge, Sherwood, WI (US); Robert Lee Popp, Hortonville, WI (US); Lewis Preole Orchard, IV, Neenah, WI (US); Jennifer Ann Diedrich, Kaukauna, WI (US); Stacy Elaine Evenson, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 31 days.

This patent is subject to a terminal disclaimer.

(21) Appl. No.: 13/933,235

(22) Filed: Jul. 2, 2013

(65) Prior Publication Data

US 2014/0018762 A1 Jan. 16, 2014

Related U.S. Application Data

(63) Continuation-in-part of application No. 13/547,974, filed on Jul. 12, 2012.

(51) Int. Cl.
*A61F 13/15* (2006.01)
*A61F 13/49* (2006.01)
(Continued)

(52) U.S. Cl.
CPC ............ *A61F 13/49006* (2013.01); *A41B 9/12* (2013.01); *A61F 13/505* (2013.01);
(Continued)

(58) Field of Classification Search
CPC ............ A61F 13/15203; A61F 13/505; A61F 13/665; A61F 13/68; A61F 13/72; A61F 13/74; A61F 2013/15284; A61F 2013/15292; A61F 2013/153; A61F 2013/15325; A61F 2013/5055; A41B 9/12
See application file for complete search history.

(56) References Cited

U.S. PATENT DOCUMENTS 1,959,282 A 5/1934 Bade
2,840,078 A 6/1958 Smith
(Continued)

FOREIGN PATENT DOCUMENTS

EP 0 274 753 A2 7/1988
EP 0 945 110 A2 9/1999
(Continued)

OTHER PUBLICATIONS

Co-pending U.S. Appl. No. 29/459,644, filed Jul. 2, 2013, by De Bruin et al. for "Portion of an Absorbent Article."
(Continued)

*Primary Examiner* — Lynne Anderson
(74) *Attorney, Agent, or Firm* — Kimberly-Clark Worldwide, Inc.

(57) ABSTRACT

A permanently closed containment pant includes an elastically extensible chassis and a sling positioned within the chassis. The sling is joined to the front waist region and the back waist region. The sling includes a fluid-impervious base sheet and a containment flap joined with the base sheet to create a fluid-impervious pouch. The sling also includes a first transition and a second transition that are elastically extensible in a longitudinal direction and in a transverse direction. Material properties of the pouch and chassis provide the proper fit for comfort and leakage protection.

18 Claims, 40 Drawing Sheets

(51) Int. Cl.
*A61F 13/74* (2006.01)
*A61F 13/72* (2006.01)
*A41B 9/12* (2006.01)
*A61F 13/505* (2006.01)

(52) U.S. Cl.
CPC ............... *A61F 13/72* (2013.01); *A61F 13/74* (2013.01); *A61F 2013/15325* (2013.01); *A61F 2013/5055* (2013.01)

(56) References Cited

U.S. PATENT DOCUMENTS

| | | |
|---|---|---|
| 2,881,761 A | 4/1959 | Kenner |
| 2,985,170 A | 5/1961 | Jack |
| 3,000,381 A | 9/1961 | Mulhole et al. |
| 3,079,922 A | 3/1963 | Papajohn |
| 3,874,385 A | 4/1975 | Gellert |
| 3,916,900 A | 11/1975 | Breyer et al. |
| 4,034,760 A | 7/1977 | Amirsakis |
| 4,381,781 A | 5/1983 | Sciaraffa et al. |
| 4,568,342 A | 2/1986 | Davis |
| 4,604,096 A | 8/1986 | Dean et al. |
| 4,605,404 A | 8/1986 | Sneider |
| 4,642,110 A | 2/1987 | Dudek |
| 4,695,279 A | 9/1987 | Steer |
| 4,735,624 A | 4/1988 | Mazars |
| 4,762,521 A | 8/1988 | Roessler et al. |
| 4,772,282 A | 9/1988 | Oakley |
| 4,834,737 A | 5/1989 | Khan |
| 4,865,597 A | 9/1989 | Mason, Jr. et al. |
| 4,865,916 A | 9/1989 | Yamaura et al. |
| 4,955,880 A | 9/1990 | Rodriquez |
| 4,964,857 A | 10/1990 | Osborn |
| 5,032,119 A | 7/1991 | Hookano |
| 5,069,672 A | 12/1991 | Wippler et al. |
| 5,098,423 A | 3/1992 | Pieniak et al. |
| 5,108,385 A | 4/1992 | Snyder |
| D327,319 S | 6/1992 | Ruffo et al. |
| 5,207,663 A | 5/1993 | McQueen |
| 5,210,882 A | 5/1993 | Moretz et al. |
| 5,217,447 A | 6/1993 | Gagnon |
| 5,217,782 A | 6/1993 | Moretz et al. |
| 5,221,277 A | 6/1993 | Beplate |
| 5,236,428 A | 8/1993 | Zajaczkowski |
| D343,681 S | 1/1994 | Hull |
| 5,290,269 A | 3/1994 | Heiman |
| 5,290,270 A | 3/1994 | Fisher |
| 5,291,617 A | 3/1994 | Moretz et al. |
| 5,306,536 A | 4/1994 | Moretz et al. |
| 5,315,717 A | 5/1994 | Moretz et al. |
| H1340 H | 7/1994 | Yetter et al. |
| 5,325,543 A | 7/1994 | Allen |
| 5,360,422 A | 11/1994 | Brownlee et al. |
| 5,387,208 A | 2/1995 | Ashton et al. |
| 5,397,318 A | 3/1995 | Drier |
| 5,405,342 A | 4/1995 | Roessler et al. |
| 5,409,476 A | 4/1995 | Coates |
| 5,458,591 A | 10/1995 | Roessler et al. |
| 5,514,104 A | 5/1996 | Cole et al. |
| 5,558,661 A | 9/1996 | Roe et al. |
| 5,562,648 A | 10/1996 | Peterson |
| 5,669,902 A | 9/1997 | Sivilich |
| 5,707,364 A | 1/1998 | Coates |
| 5,795,348 A | 8/1998 | Roe et al. |
| 5,814,037 A | 9/1998 | Coates |
| 5,830,201 A | 11/1998 | George et al. |
| 5,891,120 A | 4/1999 | Chmielewski |
| 5,891,122 A | 4/1999 | Coates |
| 6,007,528 A | 12/1999 | Osborn, III |
| D421,802 S | 3/2000 | Van Gompel et al. |
| D422,077 S | 3/2000 | Suprise et al. |
| 6,061,839 A | 5/2000 | Smolik |
| D436,400 S | 1/2001 | Kiecker |
| 6,168,585 B1 | 1/2001 | Cesco-Cancian |
| 6,183,458 B1 | 2/2001 | Ahlstrand et al. |
| D438,614 S | 3/2001 | Ratliff et al. |
| D438,615 S | 3/2001 | Dimitrijevs et al. |
| D439,662 S | 3/2001 | Ratliff et al. |
| 6,229,061 B1 | 5/2001 | Dragoo et al. |
| 6,254,583 B1 | 7/2001 | Coates |
| 6,262,331 B1 | 7/2001 | Nakahata et al. |
| D452,315 S | 12/2001 | Coates |
| 6,359,192 B1 | 3/2002 | Schmidt et al. |
| D456,508 S | 4/2002 | Schroeder et al. |
| D457,950 S | 5/2002 | Schroeder et al. |
| D457,951 S | 5/2002 | Abney et al. |
| D462,439 S | 9/2002 | Montgomery et al. |
| D463,022 S | 9/2002 | Montgomery et al. |
| D463,858 S | 10/2002 | Sherrod et al. |
| 6,468,257 B1 | 10/2002 | Ono et al. |
| 6,486,379 B1 | 11/2002 | Chen et al. |
| D470,935 S | 2/2003 | Sherrod et al. |
| 6,575,952 B2 | 6/2003 | Kirk et al. |
| 6,605,071 B1 | 8/2003 | Gray et al. |
| 6,623,466 B1 | 9/2003 | Richardson |
| 6,786,895 B1 | 9/2004 | Schmitz |
| 6,808,516 B2 | 10/2004 | Tsuji et al. |
| 6,848,121 B1 | 2/2005 | Halid |
| 6,890,325 B2 | 5/2005 | Edens et al. |
| 6,895,603 B2 | 5/2005 | Coates |
| 6,926,705 B1 | 8/2005 | Coates |
| 7,052,485 B2 | 5/2006 | Suzuki |
| 7,156,832 B2 | 1/2007 | Drevik et al. |
| 7,166,095 B1 | 1/2007 | Coates |
| 7,175,613 B2 | 2/2007 | Sugiyama et al. |
| 7,264,615 B2 | 9/2007 | Sherrod et al. |
| 7,322,966 B1 | 1/2008 | Deerin |
| D561,334 S | 2/2008 | Martynus et al. |
| 7,387,620 B2 | 6/2008 | Watanabe et al. |
| 7,393,346 B2 | 7/2008 | Morman et al. |
| D595,844 S | 7/2009 | Giloh |
| D609,805 S | 2/2010 | Moravek et al. |
| 7,749,210 B2 | 7/2010 | Mishima et al. |
| 7,824,387 B2 | 11/2010 | Lavon |
| D636,487 S | 4/2011 | Nnenna |
| 7,938,814 B2 | 5/2011 | Koyama et al. |
| D643,919 S | 8/2011 | Walker et al. |
| 8,216,201 B2 | 7/2012 | Beck |
| D679,004 S | 3/2013 | Norman et al. |
| 2002/0016579 A1 | 2/2002 | Stenberg |
| 2002/0032422 A1 | 3/2002 | Goyarts |
| 2002/0133134 A1 | 9/2002 | Wilbon |
| 2002/0143309 A1 | 10/2002 | Glasgow et al. |
| 2002/0165515 A1 | 11/2002 | Burnham |
| 2002/0169479 A1 | 11/2002 | Vesnaver |
| 2002/0177829 A1 | 11/2002 | Fell et al. |
| 2003/0004484 A1 | 1/2003 | Hammons et al. |
| 2003/0163105 A1 | 8/2003 | Tears et al. |
| 2003/0199844 A1 | 10/2003 | Lavon et al. |
| 2003/0216705 A1 | 11/2003 | Coates |
| 2004/0102751 A1 | 5/2004 | Schueler |
| 2004/0127867 A1 | 7/2004 | Odorzynski et al. |
| 2005/0124957 A1 | 6/2005 | Giloh |
| 2005/0256487 A1 | 11/2005 | Williams |
| 2006/0167432 A1 | 7/2006 | Sigari |
| 2006/0206085 A1 | 9/2006 | Gegelys et al. |
| 2006/0247599 A1* | 11/2006 | Mullen et al. ................. 604/393 |
| 2007/0135788 A1 | 6/2007 | Damay et al. |
| 2008/0065039 A1 | 3/2008 | Labit et al. |
| 2008/0082071 A1 | 4/2008 | Bryant et al. |
| 2008/0110775 A1 | 5/2008 | Beck et al. |
| 2008/0215028 A1 | 9/2008 | Brown et al. |
| 2008/0312632 A1 | 12/2008 | Fernfors |
| 2009/0299313 A1 | 12/2009 | Knightingale et al. |
| 2010/0130955 A1 | 5/2010 | Tice |
| 2010/0179495 A1 | 7/2010 | Roe |
| 2010/0179496 A1 | 7/2010 | Roe et al. |
| 2010/0179498 A1 | 7/2010 | Roe |
| 2010/0179499 A1 | 7/2010 | Roe |
| 2010/0179500 A1 | 7/2010 | Roe et al. |
| 2010/0179501 A1 | 7/2010 | Roe et al. |
| 2010/0179502 A1 | 7/2010 | Roe |
| 2010/0179503 A1 | 7/2010 | Roe et al. |
| 2010/0199496 A1 | 8/2010 | Demania et al. |

(56) References Cited

U.S. PATENT DOCUMENTS

| | | |
|---|---|---|
| 2010/0298801 A1 | 11/2010 | Beck |
| 2011/0004179 A1 | 1/2011 | Kurihara |
| 2011/0178492 A1 | 7/2011 | Coates |
| 2011/0184371 A1 | 7/2011 | Sakaguchi |
| 2011/0270211 A1 | 11/2011 | Roe et al. |
| 2012/0022492 A1 | 1/2012 | Roe |
| 2012/0029459 A1 | 2/2012 | Hallouin |
| 2012/0123364 A1 | 5/2012 | Coates |
| 2012/0123366 A1 | 5/2012 | Brownlee |
| 2013/0172844 A1* | 7/2013 | Coates .................... 604/385.14 |
| 2014/0013490 A1 | 1/2014 | Evenson et al. |
| 2014/0018756 A1 | 1/2014 | De Bruin et al. |
| 2014/0018757 A1 | 1/2014 | De Bruin et al. |
| 2014/0018760 A1 | 1/2014 | Orchard IV et al. |
| 2014/0018761 A1 | 1/2014 | Orchard IV et al. |
| 2014/0018763 A1 | 1/2014 | Evenson et al. |
| 2014/0018764 A1 | 1/2014 | Johnston et al. |
| 2015/0007382 A1* | 1/2015 | Akerley ............................ 2/406 |

FOREIGN PATENT DOCUMENTS

| | | |
|---|---|---|
| EP | 0 830 122 B1 | 11/2000 |
| EP | 2 198 818 A1 | 6/2010 |
| EP | 1 448 140 B1 | 3/2011 |
| FR | 2 975 587 A1 | 11/2012 |
| GB | 0 140 202 A | 3/1920 |
| GB | 0 400 156 A | 10/1933 |
| GB | 0 409 056 A | 4/1934 |
| GB | 1 094 143 A | 12/1967 |
| JP | 11-033055 A | 2/1999 |
| WO | WO 95/10992 A1 | 4/1995 |
| WO | WO 98/37840 A1 | 9/1998 |
| WO | WO 98/43574 A1 | 10/1998 |
| WO | WO 02/067833 A1 | 9/2002 |
| WO | WO 2004/069093 A2 | 8/2004 |
| WO | WO 2007/021734 A2 | 2/2007 |
| WO | WO 2010/083290 A1 | 7/2010 |
| WO | WO 2012/009357 A1 | 1/2012 |
| WO | WO 2012/123031 A1 | 9/2012 |
| WO | WO 2013/023035 A1 | 2/2013 |

OTHER PUBLICATIONS

Co-pending U.S. Appl. No. 29/459,639, filed Jul. 2, 2013, by Evenson et al. for "Portion of a Sling for Use in a Containment Pant."
Jamilynn84, "Goodnights true fit real underwear 60-100 lbs," personal posting on Internet web page "http://www.diaperswappers.com/forum/showthread.php?t=1437993", Aug. 30, 2012, 2 pages.

* cited by examiner

CONTAINMENT PANT

RELATED APPLICATION DATA

This application is a continuation-in-part of application Ser. No. 13/547,974 filed on Jul. 12, 2012. The entirety of application Ser. No. 13/547,974 is hereby incorporated by reference.

BACKGROUND OF THE INVENTION

While disposable absorbent garments offer a convenient way to manage bedwetting, many enuretic families are not satisfied with these products because they are viewed as "diaper-like" by the user who wants to wear conventional underwear. As such, many improvements have been made to disposable absorbent garments to make them more underwear-like. For example, gender specific graphics have been added and softer nonwoven materials have been utilized. However, many potential users still seek a product that looks and feels more like conventional underwear but is still able to help manage bedwetting. Thus, there remains a need for a pant that is underwear-like yet helps to contain urine insults.

SUMMARY OF THE INVENTION

In one aspect, the present invention provides a permanently closed containment pant. The containment pant includes an elastically extensible chassis defining a waist opening, a first leg opening, and a second leg opening. The waist opening includes a front waist region joined with a back waist region. The containment pant also includes a sling positioned within the chassis. The sling may be joined to the front waist region and the back waist region. The sling includes a fluid-impervious base sheet and a containment flap joined with the base sheet to create a fluid-impervious pouch. The sling further includes a first transition and a second transition that are elastically extensible in a longitudinal direction and in a transverse direction. The base sheet may be a fabric to define and a first fabric surface. The containment flap may be a fabric to define a second fabric surface wherein the first fabric surface is joined with the second fabric surface.

In some embodiment, the chassis has a transverse elongation of between 125% and 175% at 2000 grams force and a longitudinal elongation of between 125% and 175% at 2000 grams force. In this embodiment, the base sheet has a transverse elongation of between 10% and 40% at 1400 grams force and a longitudinal elongation of between 10% and 40% at 1400 grams force.

In other embodiments, a peak load of the chassis material and the base sheet in the transverse direction and in the longitudinal direction is between about 10,000 grams force and about 30,000 grams force.

In other embodiments, chassis materials for use in the containment pant herein have a breathability of between about 10,000 and about 35,000 grams/(m²-24 hours). In addition, the base sheet materials for use in the sling of the containment pant herein have a breathability of between about 500 and about 2500 grams/(m²-24 hours).

In some embodiments of this aspect, the sling may further include a first transition and a second transition that are elastically extensible in a longitudinal direction and in a transverse direction. In some embodiments, the first transition is a discrete piece of material joined between the pouch and the waist elastic in the front waist region and the second transition is a discrete piece of material joined between the pouch and the waist elastic in the back waist region. In some embodiments, the chassis includes a shell material and the first transition is an integral part of and a distinct projection of the shell material. The first transition is joined between the pouch and the waist elastic in the front waist region. The second transition is a discrete piece of material joined between the pouch and the waist elastic in the back waist region.

In some embodiments of this aspect, the base sheet may be a woven polyester fabric laminated with a polyurethane sheet. In some embodiments, the base sheet is a first fabric laminated with polyurethane to define a polyurethane surface and a fabric surface. The containment flap is a second fabric laminated with polyurethane to define a second fabric surface and a second polyurethane surface. In these embodiments, the first polyurethane surface may be joined with the second polyurethane surface.

In some embodiments of this aspect, the sling may be attached to the chassis in a crotch region with a tab. The tab may be a discrete piece of material that is ultrasonically bonded to the pouch and is sewed with thread to the chassis. The tab may be an integral part of the containment flap and may be a distinct projection of the containment flaps and may be sewed with thread to the chassis. The tab may be an integral part of the base sheet and may be a distinct projection of the base sheet and may be sewed with thread to the chassis. The tab may be an integral part and distinct projection of the chassis and may be sewed to the pouch.

In some embodiments of this aspect, the fluid-impervious pouch defines a pouch floor having a first end section, a second end section, and a central section extending between the first end section and the second end section. The first end section defines a maximum width, the second end section defines a maximum width equal to the maximum width of the first end section, and the central section defines a maximum width that is less than 70% the maximum width of the first and second end sections.

In some embodiments of this aspect, the chassis includes a shell material made of cotton and 2-25% spandex. In some embodiments, the permanently closed containment pant includes a waistband, a first leg elastic, and a second leg elastic. The waistband may extend around 100% of the waist opening and may be cantilevered relative to the shell material. The first leg elastic may extend around 100% of the first leg opening and the second leg elastic may extend around 100% of the second leg opening. The first leg elastic and the second leg elastic may be cantilevered relative to the shell material.

In some embodiments of this aspect, the containment flaps may have an initial curved cut. In some embodiments, the containment flap defines a proximal portion and a distal portion having a distal edge. The proximal portion may be joined with the base sheet and the distal portion may include a flap elastic folded over the distal edge of the flap. In some embodiments, the flap elastic defines a first tension zone, a second tension zone, and a third tension zone along a length of the containment flap. The second tension zone is located between the first tension zone and the third tension zone. The flap elastic may have a greater tension in the second tension zone than in the first tension zone or the third tension zone.

In some embodiments of this aspect, the first transition is made of a first material, the second transition is made of the same first material, and the chassis is made of the same first material. The first material may be 75-98% cotton and 2-25% spandex. The base sheet may be a polyester fabric laminated with polyurethane and the containment flap may be a polyester fabric laminated with polyurethane.

In some embodiments of this aspect, the fluid-impervious pouch defines a pouch floor having a first end section, a second end section, and a central section extending between the first end section and the second end section. The first end section defines a maximum width, the second end section defines a maximum width equal to the maximum width of the first end section, and the central section defines a maximum width that is less than 70% the maximum width of the first and second end sections.

DETAILED DESCRIPTION OF THE DRAWINGS

The containment pant of the present invention provides a durable outer chassis and an inner pouch for containing a disposable absorbent insert. In some embodiments, the containment pant is provided in a permanently closed condition. As used herein, the term "permanently closed" refers to a pant that is provided in a condition that is adapted to be only pulled on or pull off like conventional underwear and is distinguished from pants that have refastenable fasteners and diapers that are provided in an open condition and include fasteners for securing the diapers around the body of the wearer.

Figure 1:
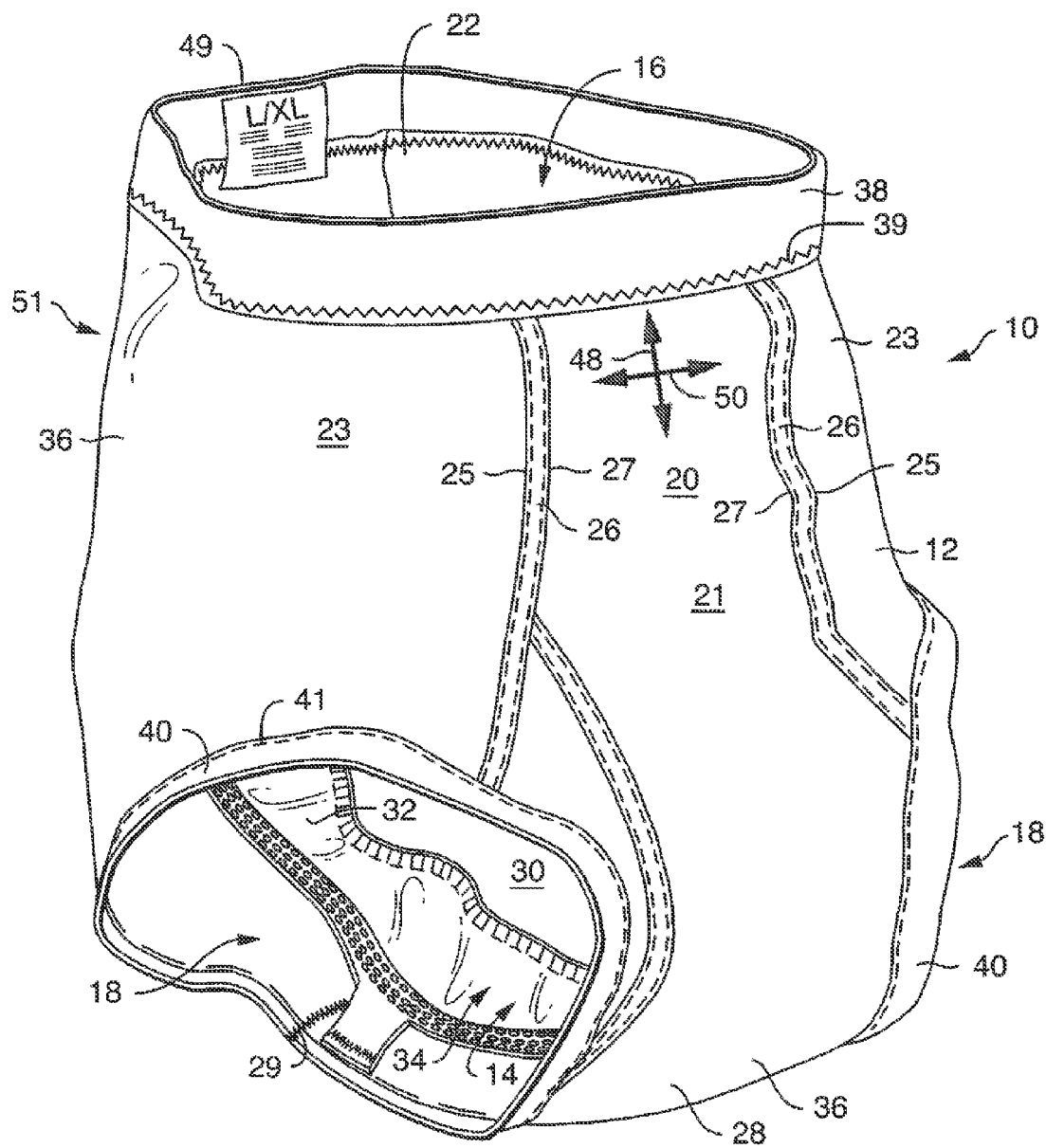
FIG. 1 representatively illustrates a front perspective view of an exemplary containment pant of the present invention.
Figure 2:
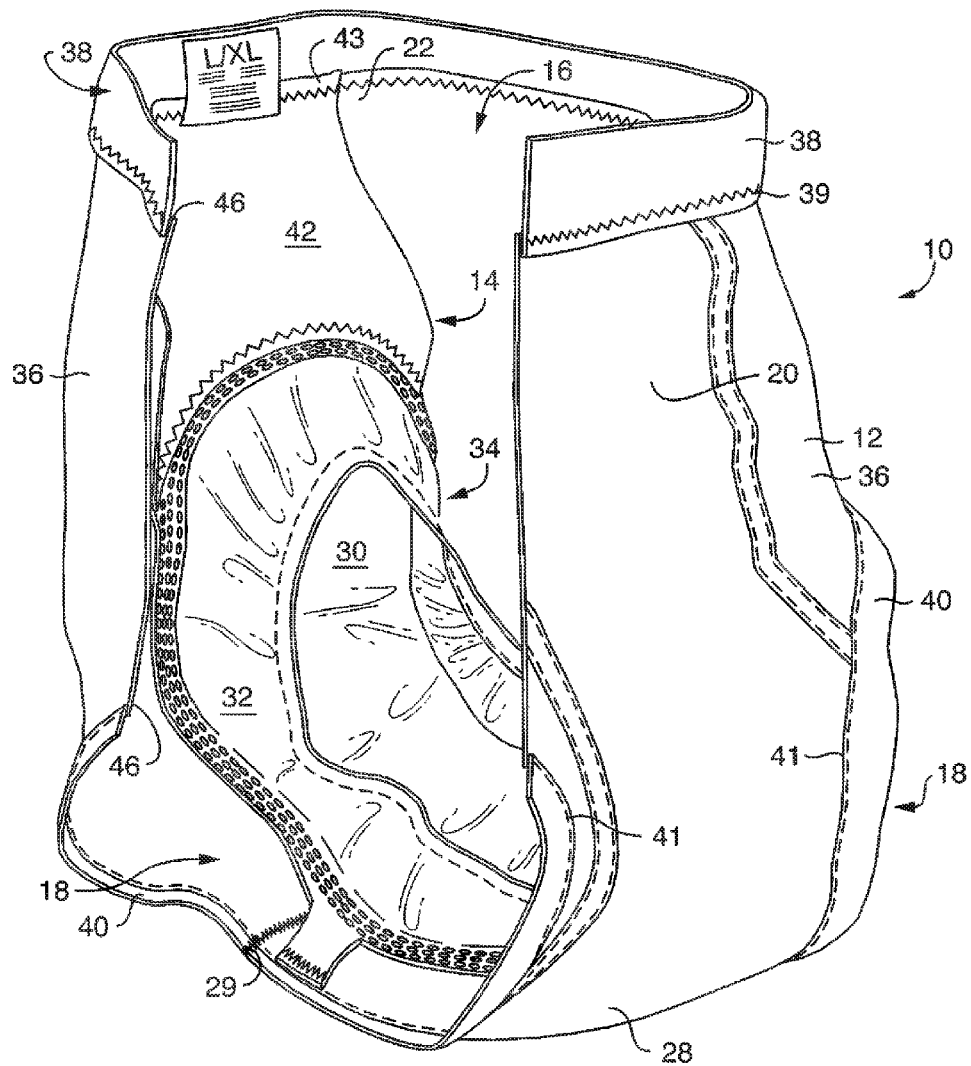
FIGS. 2 and 3 representatively illustrate a side perspective view of the containment pant of FIG. 1 with the chassis partially severed to illustrate internal structure.
Figure 3:
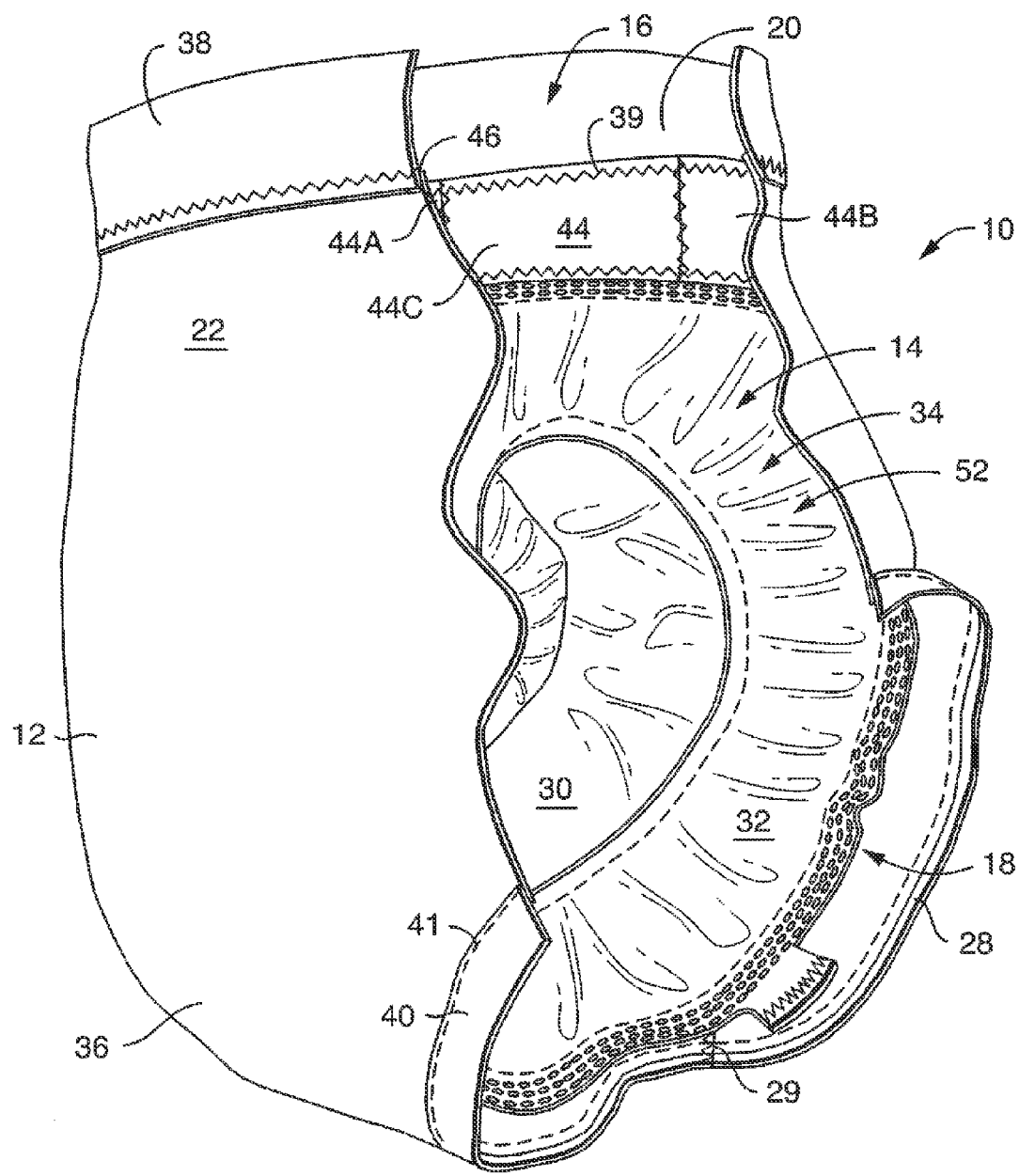

An exemplary containment pant of the present invention is representatively illustrated in FIGS. 1-3. Specifically, FIG. 1 shows a side perspective view of a containment pant 10 having a chassis 12 and a sling 14 attached within the chassis 12. The chassis 12 defines a waist opening 16 and a pair of leg openings 18. The chassis 12 also defines a front waist region 20, a back waist region 22, and a crotch region 28. The crotch region 28 is located between the front waist region 20 and the back waist region 22. The containment pant 10 of FIG. 1 is depicted in FIGS. 2 and 3 with the chassis 12 partially severed to better illustrate internal elements. FIG. 2 representatively illustrates a side perspective view with the chassis 12 partially severed to better illustrate the positioning and construction of the sling 14 in the back of the containment pant 10. FIG. 3 representatively illustrates a side perspective view with the chassis 12 partially severed to better illustrate the construction and positioning of the sling 14 in the front of the containment pant 10. The containment pant 10 defines a longitudinal direction 48 and a transverse direction 50 as illustrated in FIG. 1. The longitudinal direction 48 extends from the front waist region 20 through the crotch region 28 and into the back waist region 22. The transverse direction 50 is perpendicular to the longitudinal direction 48. The chassis 12 includes an outer shell 36 and may further include waist elastic, leg elastic, or both. Referring again to FIG. 1, the chassis 12 is illustrated with a waist elastic 38 attached to the outer shell 36 and encircling the waist opening 16 and leg elastics 40 attached to the outer shell 36 and encircling each of the leg openings 18.

Figure 6:
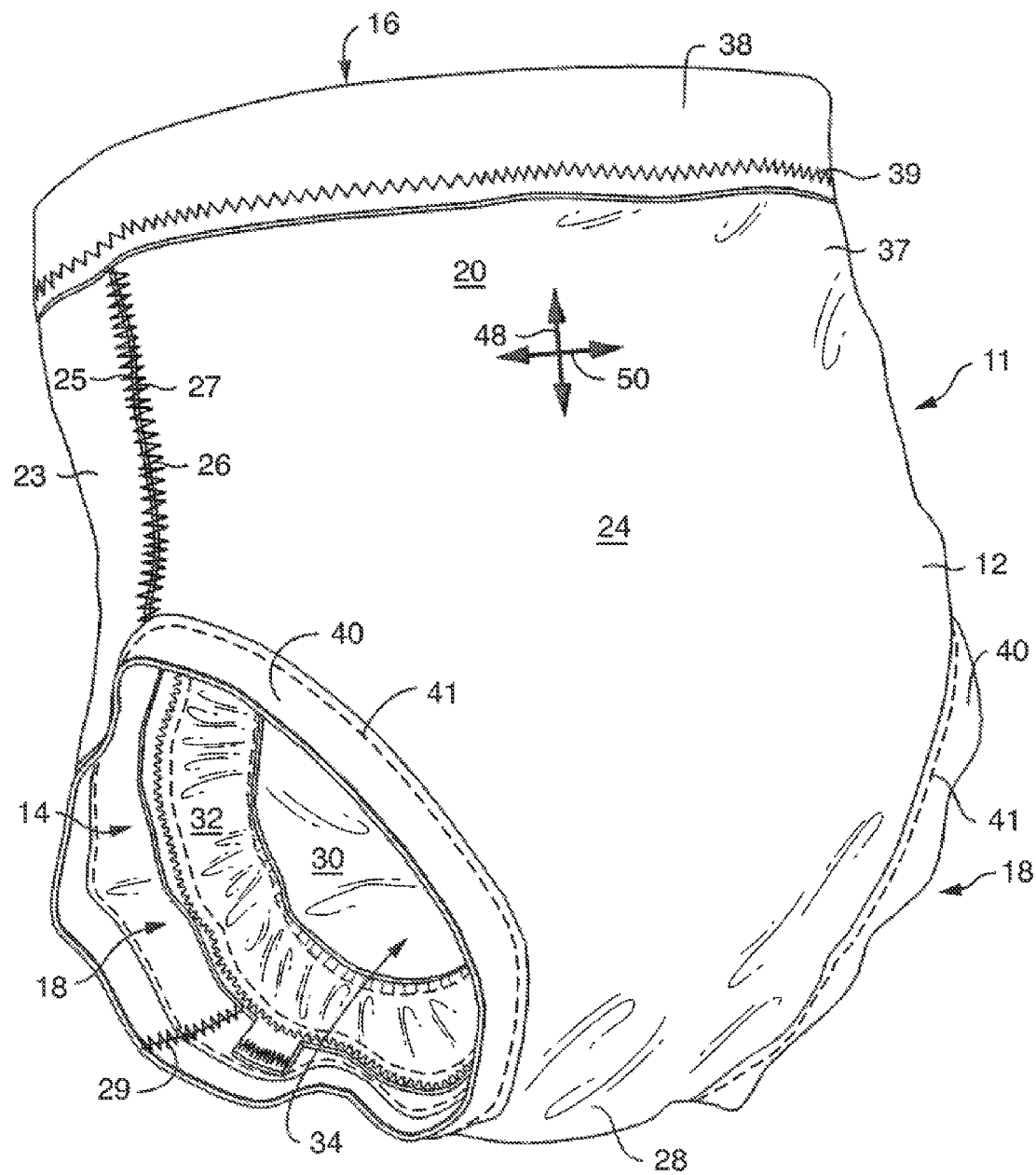
FIG. 6 representatively illustrates a front perspective view of another exemplary containment pant of the present invention.
Figure 7:
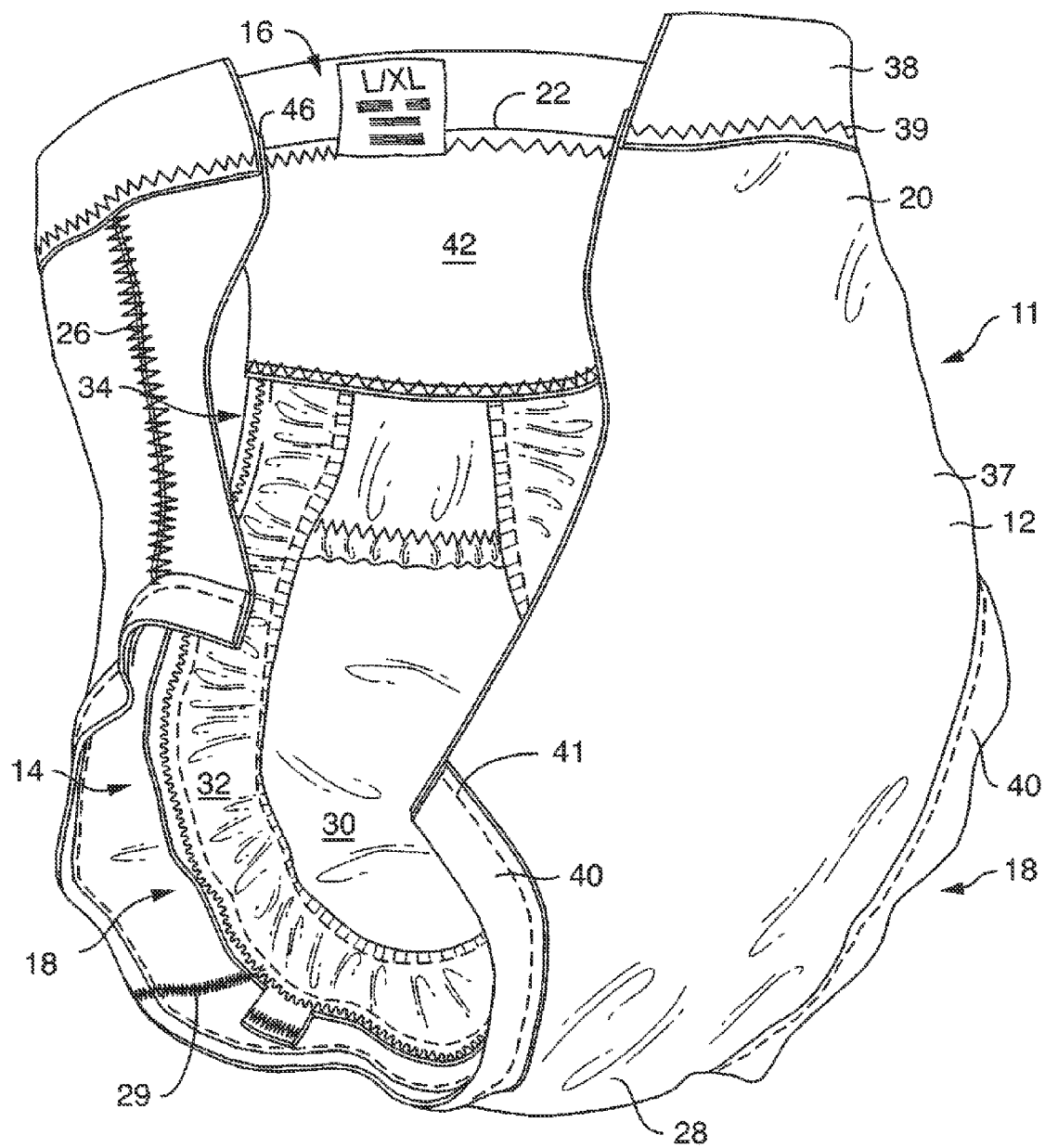
FIGS. 7 and 8 representatively illustrate a side perspective view of the containment pant of FIG. 6 with the chassis partially severed to illustrate internal structure.
Figure 8:
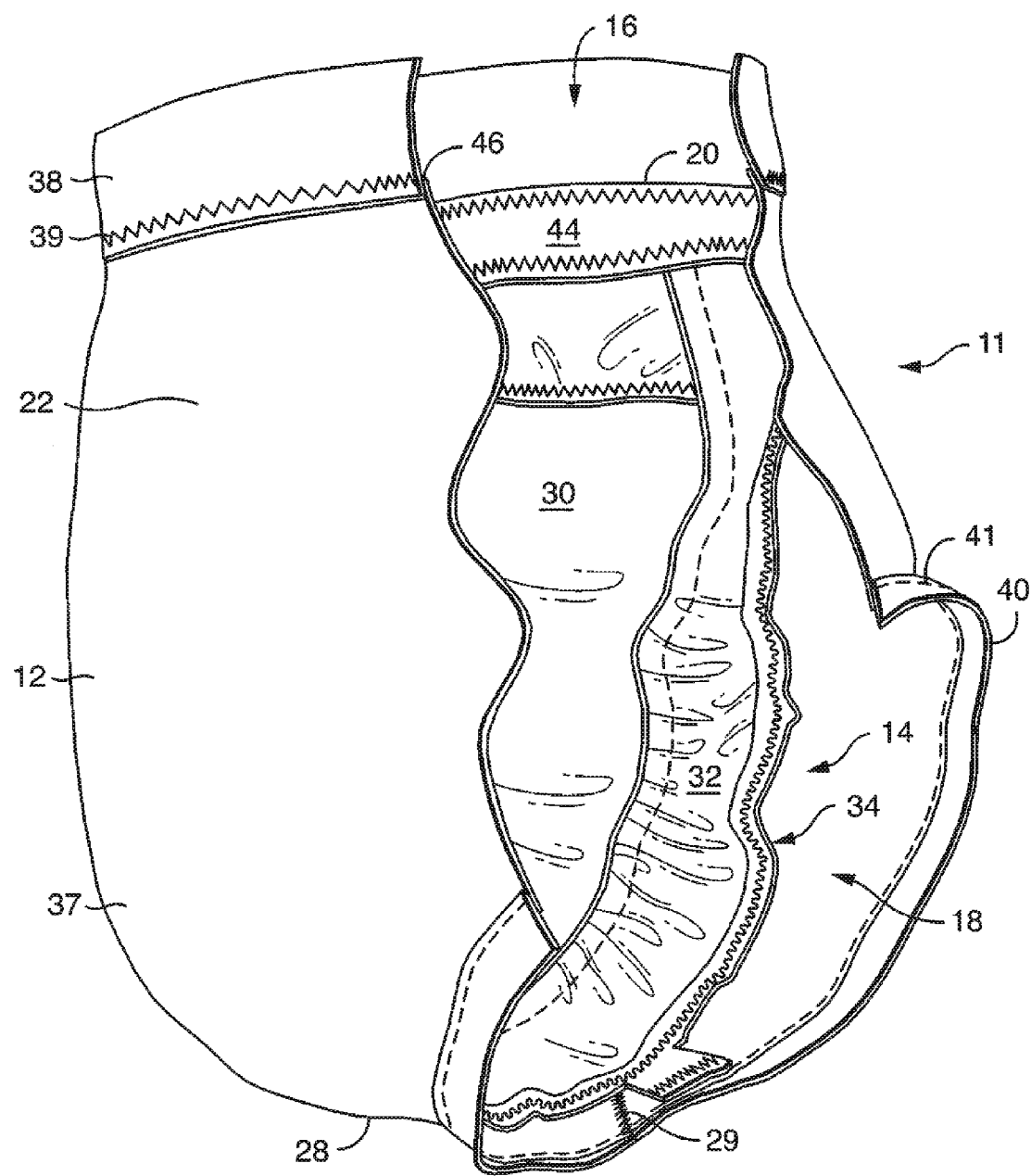

Another exemplary containment pant of the present invention is representatively illustrated in FIGS. 6-8. Specifically, FIG. 6 shows a side perspective view of a containment pant 11 having a chassis 12 and a sling 14 attached within the chassis 12. The chassis 12 defines a waist opening 16 and a pair of leg openings 18. The chassis 12 also defines a front waist region 20, a back waist region 22, and a crotch region 28. The crotch region 28 is located between the front waist region 20 and the back waist region 22. The containment pant 11 of FIG. 6 is depicted in FIGS. 7 and 8 with the chassis 12 partially severed to better illustrate internal elements. FIG. 7 representatively illustrates a side perspective view with the chassis 12 partially severed to better illustrate the positioning and construction of the sling 14 in the back of the containment pant 11. FIG. 8 representatively illustrates a side perspective view with the chassis 12 partially severed to better illustrate the construction and positioning of the sling 14 in the front of the containment pant 11. The containment pant 11 also defines a longitudinal direction 48 and a transverse direction 50 as illustrated in FIG. 6. The chassis 12 includes an outer shell 37 and may further include a waist elastic 38 or leg elastics 40, or both. Referring again to FIG. 6, the chassis 12 is illustrated with a waist elastic 38 attached to the outer shell 37 and encircling the waist opening 16 and leg elastics 40 attached to the outer shell 37 and encircling each of the leg openings 18.

Figure 4:
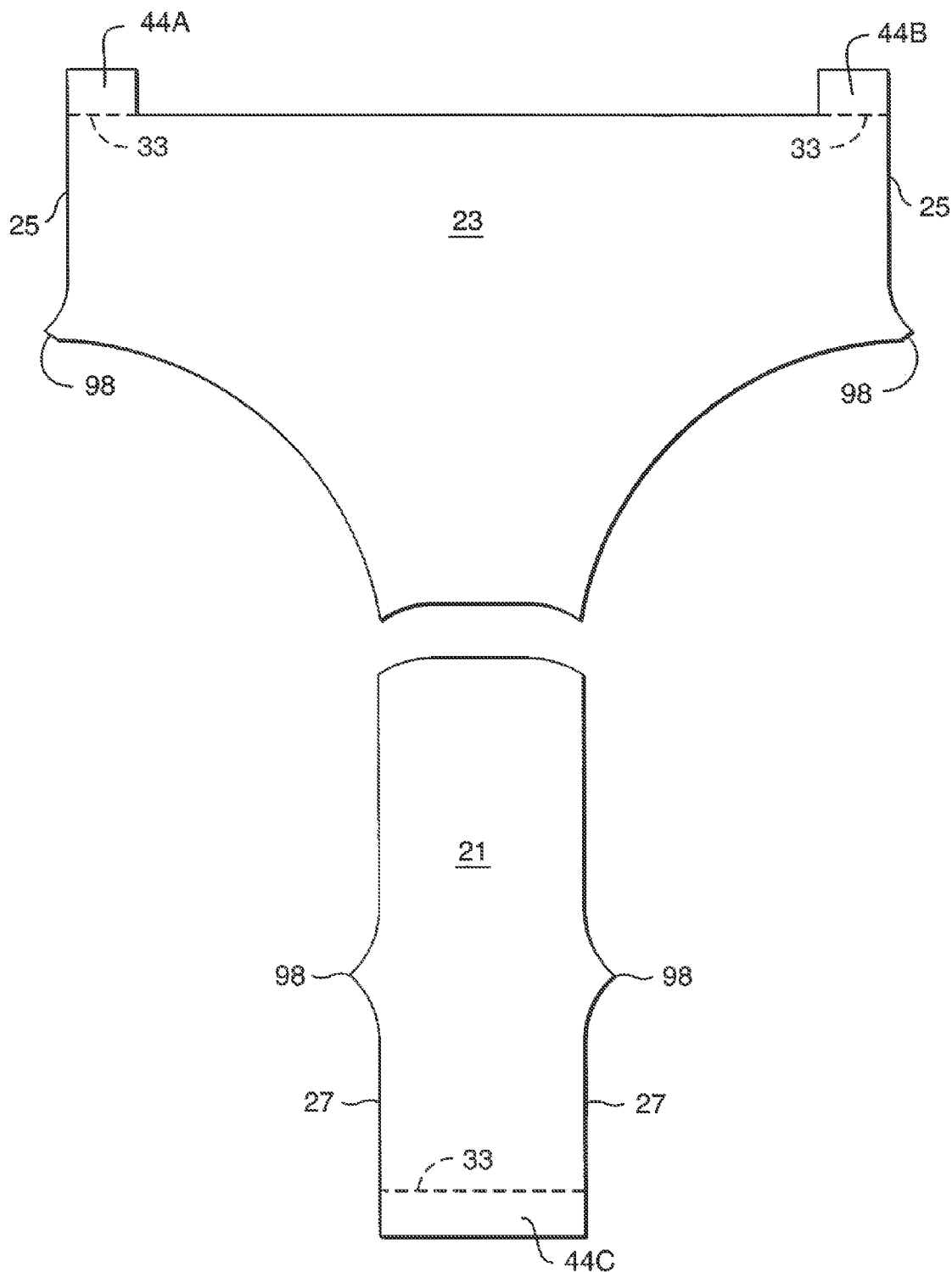
FIGS. 4 and 5 representatively illustrate a top plan view of the component pieces of the outer shell of the containment pant of FIG. 1.
Figure 9:
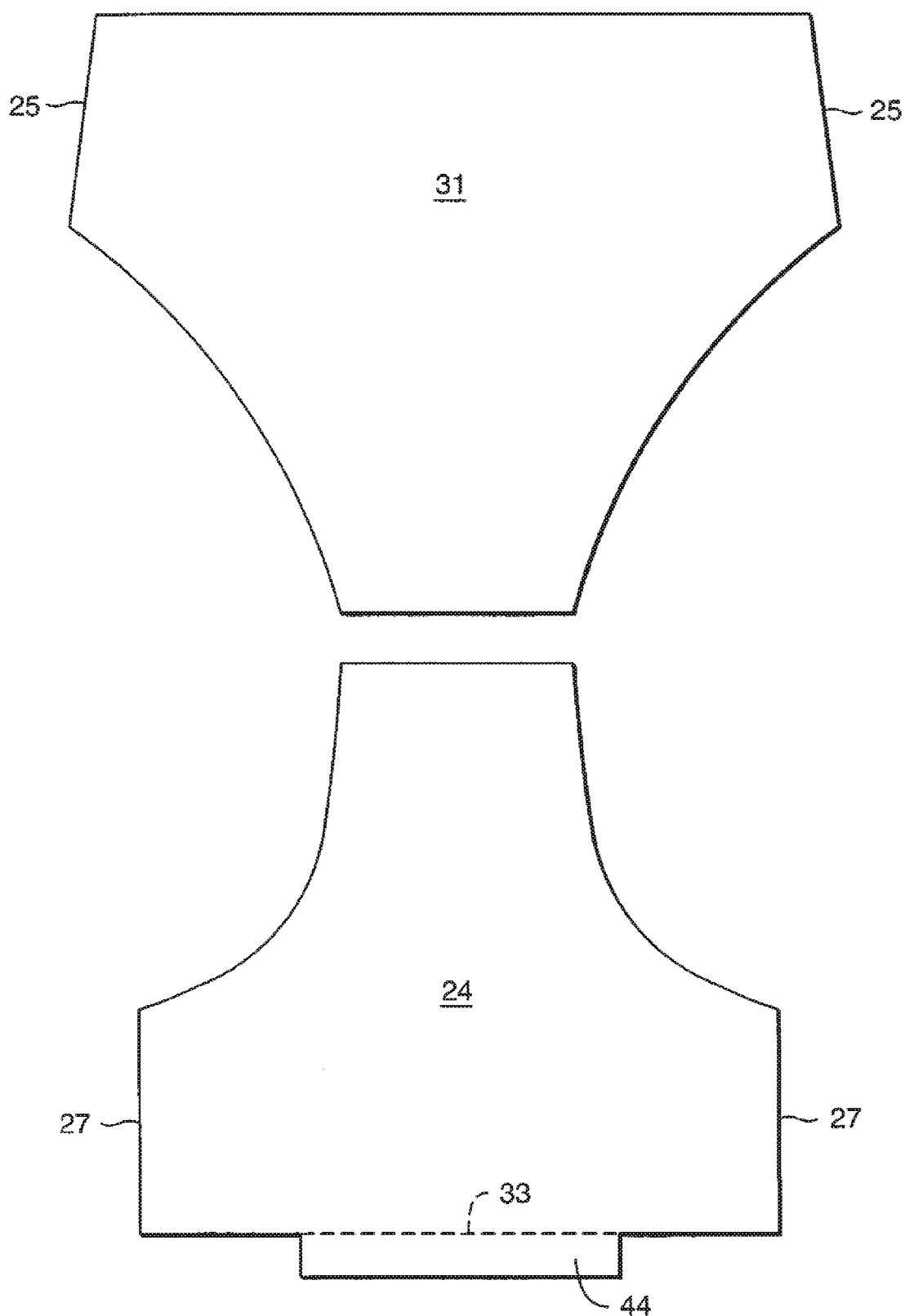
FIGS. 9 and 10 representatively illustrate a top plan view of the component pieces of the outer shell of the containment pant of FIG. 6.

In various embodiments, the outer shell may be made of a single piece of material or multiple pieces of material. In some embodiments, the outer shell may be made of two or more pieces of material. For example, FIG. 4 is a top plan view of the component pieces of the outer shell 36 of FIGS. 1-3. The component pieces include a front component 21 and a back component 23. In another example, FIG. 9 is a top plan view of the component pieces of the outer shell 37 of FIGS. 6-8. The component pieces include a front component 24 and a back component 31.

Figure 5:
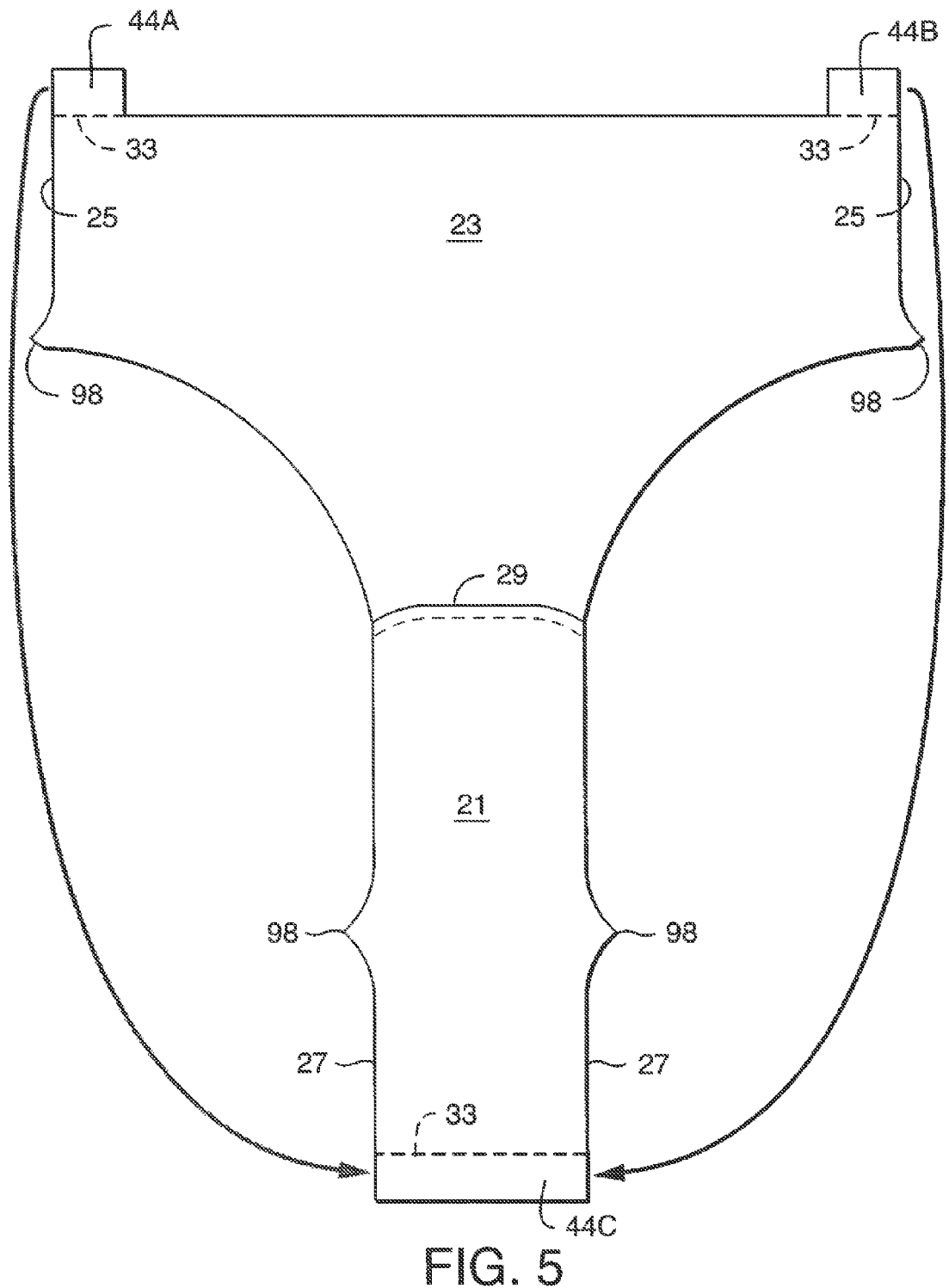
Figure 10:
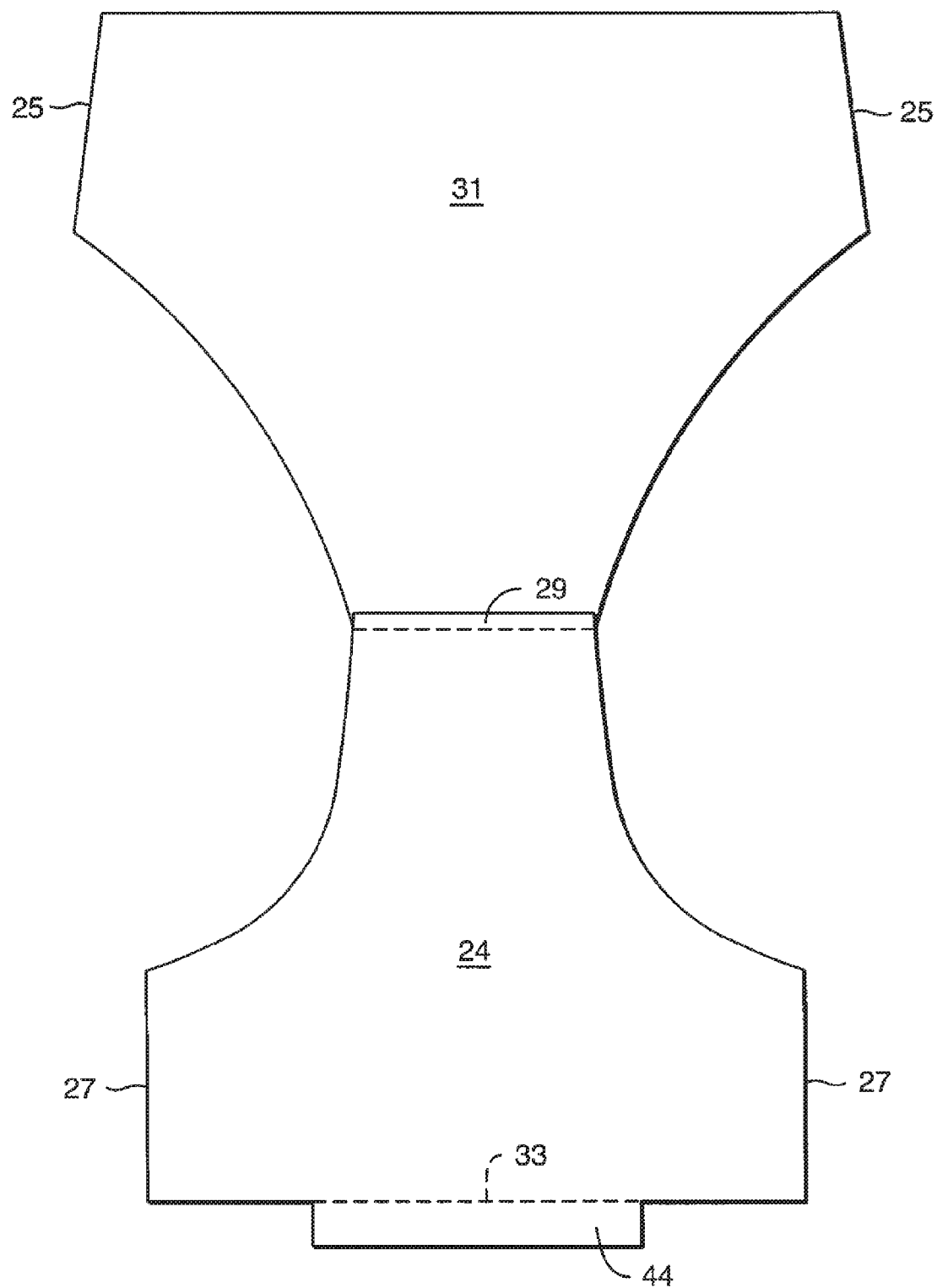

In various embodiments, the component pieces of the outer shell may be joined together in any suitable manner. For example, the front component 21 may be joined to the back component 23 at a crotch seam 29 as illustrated in FIG. 5. FIG. 5 is a top plan view of the component pieces of the outer shell 36 partially joined together. In another example, the front component 24 may be joined to the back component 31 at a crotch seam 29 as illustrated in FIG. 10. FIG. 10 is a top plan view of the component pieces of the outer shell 37 partially joined together. Additionally, one or both of the lateral side edges of the back component may be joined to one or both of the lateral side edges of the front component at one or more side seams to define a three-dimensional garment. Specifically, referring to FIG. 5, the lateral side edges 25 of the back component 23 may be joined with the lateral side edges 27 of the front component 21 at side seams 26 to define the leg openings 18 and the waist opening 16 of the containment pant 10 as illustrated in FIG. 1. Similarly, the lateral side edges 25 of the back component 31 of FIG. 10 may be joined with the lateral side edges 27 of the front component 24 at side seams 26 to define the leg openings 18 and the waist opening 16 of the containment pant 11 as illustrated in FIG. 6.

In various embodiments, the side seams and/or the crotch seams may be formed using any suitable means such as ultrasonic bonding, thermal bonding, adhesive bonding, pressure bonding, sewing, and the like and combinations thereof. In some embodiments, the side seams and/or the crotch seam may be formed by sewing the component pieces of the outer shell using thread and any suitable stitch pattern or combination of patterns. In some embodiments, the side seams and/or crotch seams may be formed using a flatlock stitch.

In some embodiments, the present invention provides a first outer shell having a first overall shape and a second outer shell having a second overall shape that is different than the first overall shape. In some embodiments, the first outer shell shape may be adapted to the anatomy of a male wearer. In some embodiments, the second outer shell shape may be adapted to the anatomy of a female wearer. Customizing the first outer shell and/or the second outer shell is believed to be beneficial to allow for differences between the genders in anatomy, body shape, and undergarment style preferences. For example, the outer shell 36 illustrated in FIG. 1 has a shape and style adapted for males. In comparison, the outer shell 37 illustrated in FIG. 6 has a shape and style adapted for females. In some embodiments, the front components 21 may include protrusions 98 for partially defining the leg openings as illustrated in FIGS. 4 and 5. Additionally, the back component 23 may also include protrusions 98 for partially defining the leg openings as illustrated in FIGS. 4 and 5. In various embodiments, the front component may have an area that is similar in size to the area of the back component as illustrated in FIGS. 9 and 10. In other embodiments, the front component may have an area that is significantly smaller than the area of the back component as illustrated in FIGS. 4 and 5.

In various embodiments, the waist elastic may encircle at least 50, 60, 70, 80, or 90 percent of the respective waist opening. In some embodiments, the waist elastic 38 may encircle 100% of the waist opening 16 as representatively illustrated in FIGS. 1 and 6. In various embodiments, the leg elastic may encircle at least 50, 60, 70, 80, or 90 percent of either or both leg openings. In some embodiments, the leg elastic 40 may encircle 100% of both leg openings 18 as representatively illustrated in FIGS. 1 and 6.

In various embodiments, the waist elastic and/or the leg elastic may be in complete facing relationship with the outer shell (Not shown). In some embodiments, the waist elastic and/or the leg elastic may be partially or completely encased within the outer shell (Not shown). In other embodiments, the waist elastic and/or the leg elastic may be cantilevered relative to the outer shell. As used herein, the term "cantilevered" refers to a waist elastic and/or leg elastic that has less than 100% facing relationship with the outer shell and extends beyond an outer edge of the outer shell. For example, referring again to FIGS. 2 and 7, the waist elastics 38 are cantilevered as they extend beyond the outer edge 46 of the respective outer shells 36 and 37. Likewise, the leg elastics 40 are also cantilevered as they extend beyond the outer edge 46 of the respective outer shells 36 and 37.

In various embodiments, the waist elastic and/or leg elastic may be joined with the outer shell using any suitable means such as ultrasonic bonding, thermal bonding, adhesive bonding, pressure bonding, sewing, and the like and combinations thereof. In some embodiments, the waist elastic and/or leg elastic may be sewed to the outer shell using thread and any suitable stitch pattern or combination of patterns. For example, FIGS. 1-3 and FIGS. 6-8 representatively illustrate the waist elastic 38 joined with the respective outer shells 36 and 37 at a sewn waist elastic seam 39 and the leg elastics 40 joined with the respective outer shells 36 and 37 at sewn leg elastic seams 41. In some embodiments, the waist elastic and/or leg elastic may be sewed to the outer shell using a cover stitch.

Inside the chassis 12 is the sling 14, which includes a fluid-impervious base sheet 30 and at least one containment flap 32 joined with the base sheet 30 to create a fluid-impervious pouch 34. The fluid-impervious pouch 34 is adapted to house a removable absorbent insert and contain fluid until it can be taken into the absorbent insert. The fluid-impervious pouch 34 is drapeable and is designed to conform and gasket against the body of the wearer.

In some embodiments, the sling 14 may further include a first transition, a second transition, or both. The first transition and the second transition are believed to be beneficial in that they allow the fluid-impervious pouch to be joined within the chassis without significantly reducing the extension and retraction properties of the outer shell and/or the waist elastic. Additionally, the first transition and the second transition are believed to be beneficial by allowing the fluid-impervious pouch to move from front to back within the chassis. This freedom of movement is believed to allow the fluid-impervious pouch to adjust after donning the containment pant and during wear.

Referring again to FIGS. 2 and 7, the sling 14 is illustrated with a second transition 42 joined with the back waist region 22 of the containment pant. Likewise, in FIGS. 3 and 8, the sling 14 is illustrated with a first transition 44 joined with the front waist region 20 of the containment pant. Alternatively, in any of the embodiments described herein, the second transition may be joined with the front waist region and the first transition may be joined with the back waist region. In various embodiments, the first transition, the second transition, or both, may be one or more discrete pieces of material joined between the pouch and the chassis. In other embodiments, the first transition, the second transition, or both, may be integral with the pouch or may be integral with the shell or any suitable portion of the chassis.

For example, FIG. 3 illustrates the first transition 44 as integral with the shell components and FIG. 2 illustrates the second transition 42 as a discrete piece of material. In this embodiment, the first transition 44 is constructed from multiple portions of the shell 36. As seen in FIGS. 4 and 5, the first transition 44 is constructed from a first part 44A, a second part 44B, and a third part 44C. The first part 44A and the second part 44B are integral with the back component 23 of the shell whereas the third part 44C is integral with the front component 21 of the shell. When the shell is constructed, the first part 44A and the second part 44B are joined with the third part 44C as illustrated by the arrows of FIG. 5. The fully constructed first transition 44 is then folded along the fold lines 33 of FIG. 5 to define the first transition 44 as illustrated in FIG. 3.

In another example, FIG. 8 also illustrates the first transition 44 as integral with the shell components and FIG. 7 illustrates the second transition 42 as a discrete piece of material. In this embodiment, the first transition 44 is constructed from a single portion of the shell 37. As seen in FIGS. 9 and 10, the first transition 44 is constructed from a portion of the front component 24 of the shell. When the shell is constructed, the first transition 44 is then folded along fold line 33 of FIG. 10 to define the first transition 44 as illustrated in FIG. 8.

Figure 11:
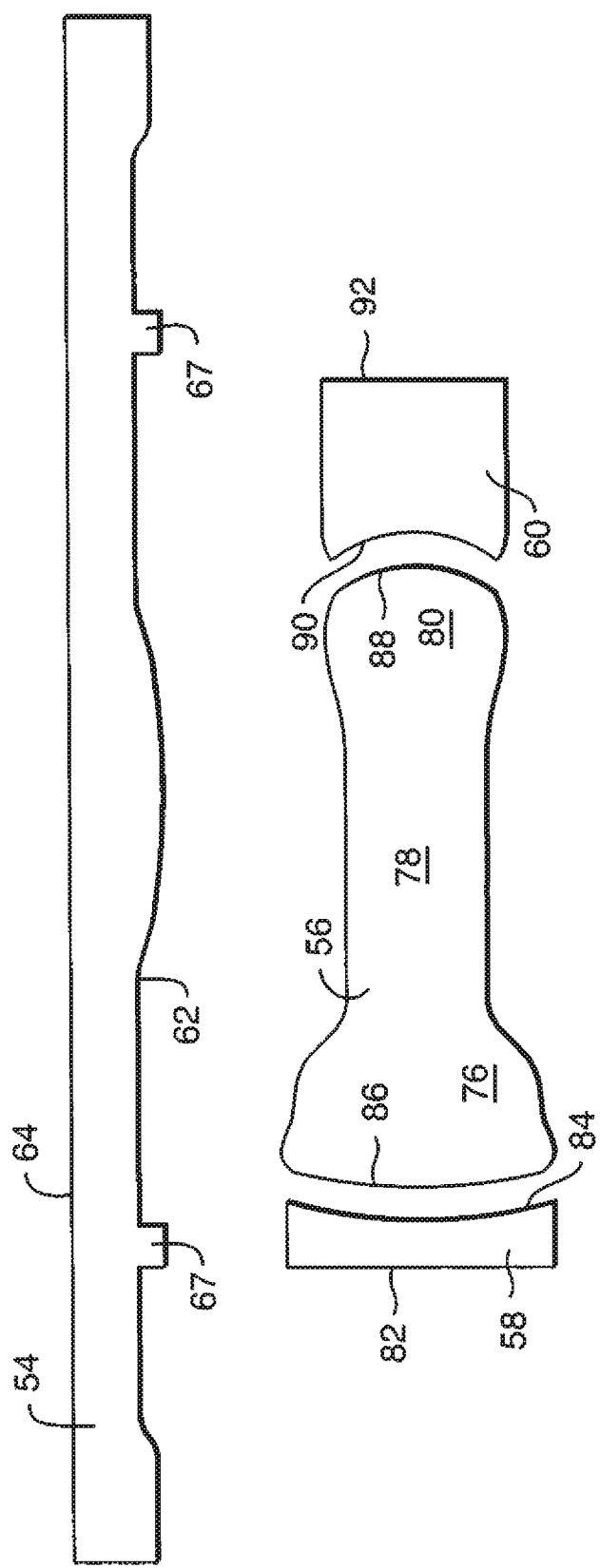
FIG. 11 representatively illustrates a top plan view of component parts of a first exemplary pouch and sling of the present invention.

In various embodiments, a sling and a fluid-impervious pouch may be constructed in any suitable manner. For example, an exemplary sling and fluid-impervious pouch may include a containment flap, a base sheet, a first transition, and a second transition. Referring now to FIG. 11, a top plan view of the component parts of an exemplary pouch and sling are representatively illustrated. A fully constructed pouch 68 made from the component parts of FIG. 11 is representatively illustrated in FIG. 12. A fully constructed sling made from the component parts of FIG. 11 is representatively illustrated in FIG. 13. A cross sectional view of the sling 52 of FIG. 13 taken along the line A-A is representatively illustrated in FIG. 14.

Figure 12:
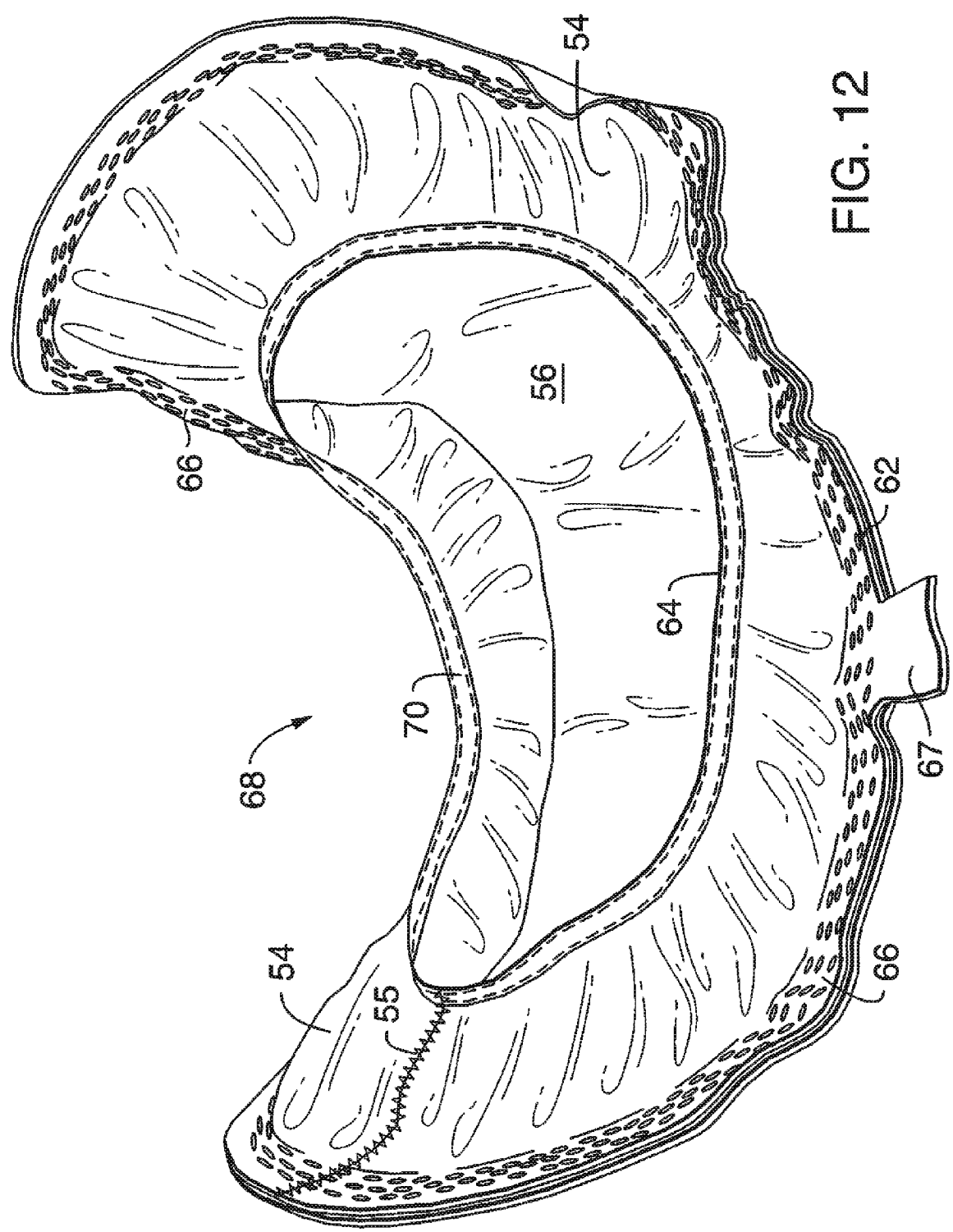
FIG. 12 representatively illustrates a fully constructed pouch made from the component parts of FIG. 11.
Figure 14:
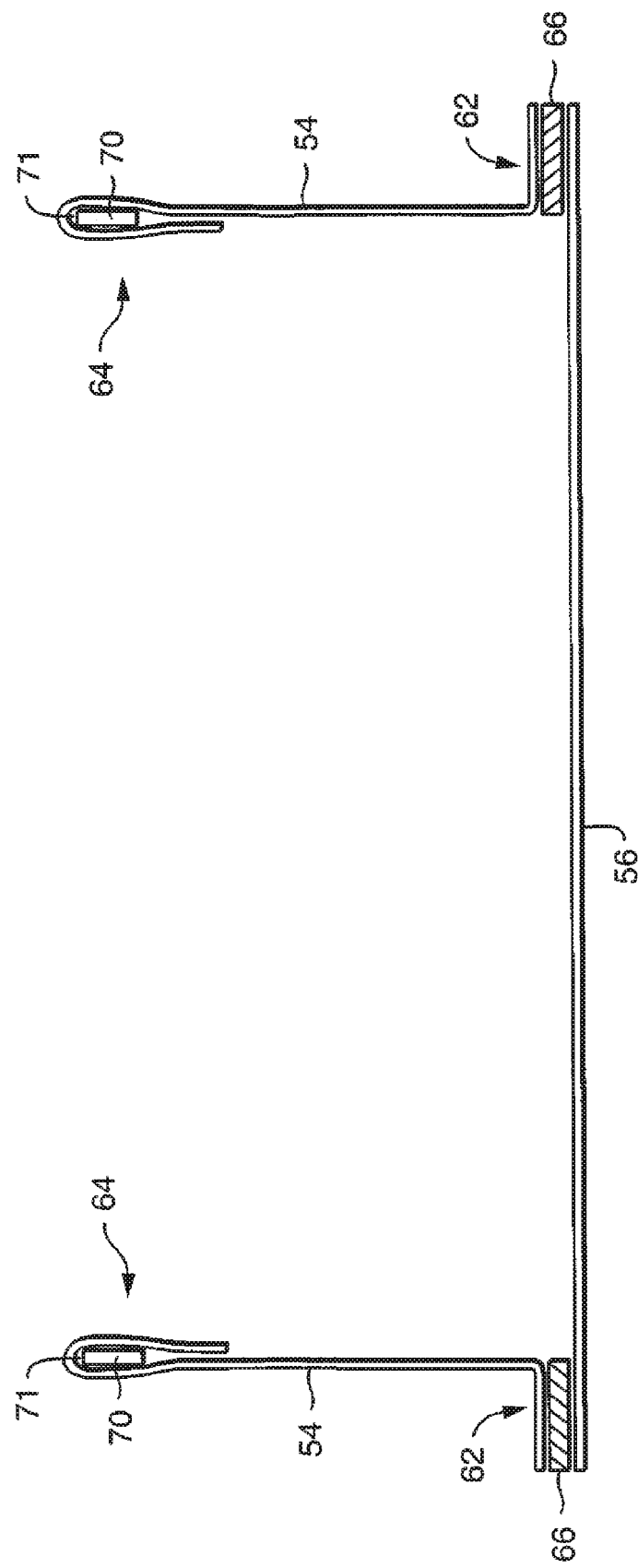
FIG. 14 representatively illustrates a cross-sectional view of the sling of FIG. 13 taken along the line A-A.

Referring now to FIG. 11, the component parts include a containment flap 54, a base sheet 56, a first transition 58, and a second transition 60. The containment flap 54 defines a proximal portion 62 and a distal portion 64. The proximal portion 62 of the containment flap 54 is joined with the base sheet 56 to create a containment flap seal 66 and define a fluid-impervious pouch 68 as illustrated in FIG. 12. In some embodiments, the containment flaps may further include one or more elastics. For example, as illustrated in FIG. 14, the distal portion 64 of the containment flap 54 further includes a containment flap elastic 70.

Figure 13:
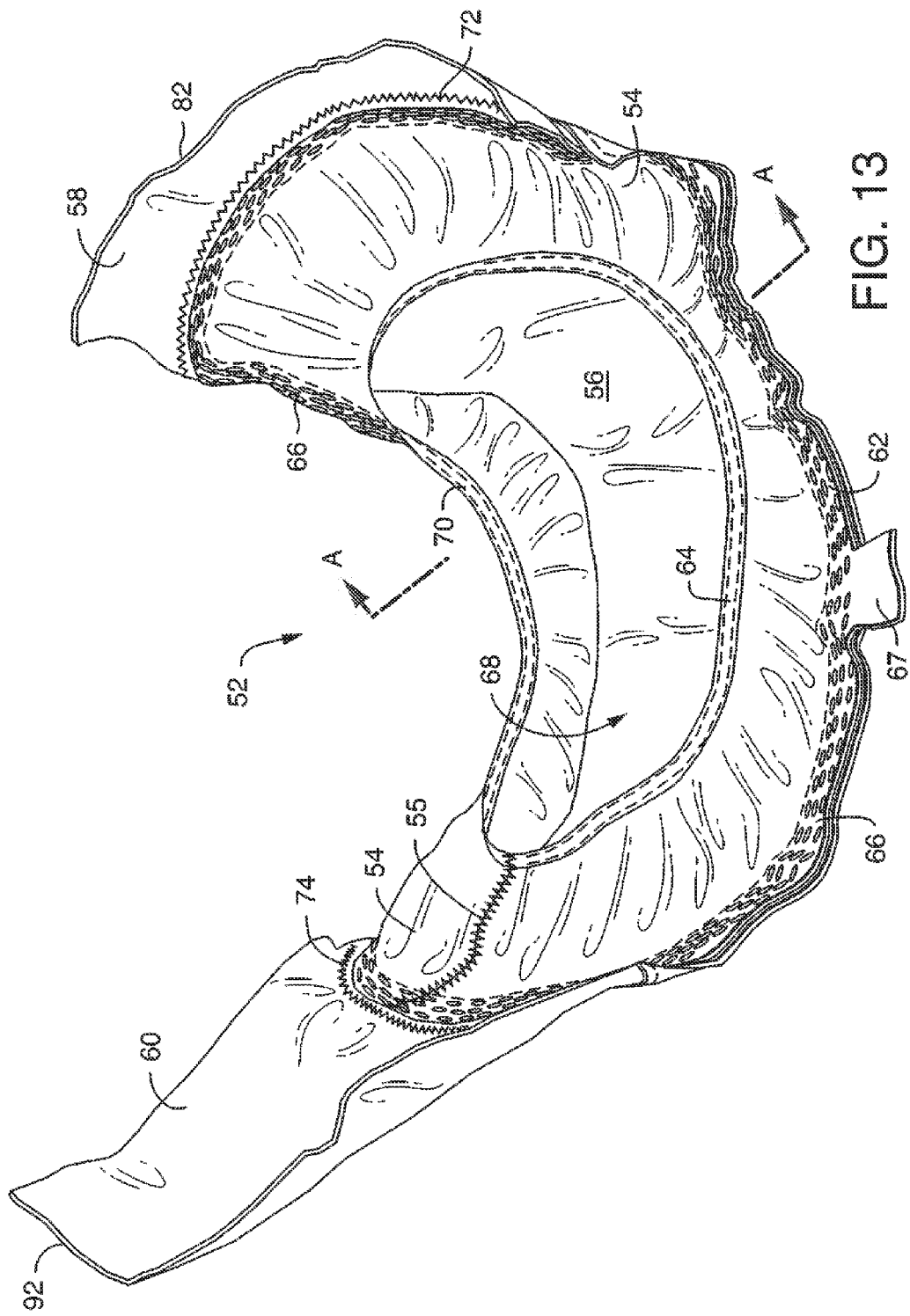
FIG. 13 representatively illustrates a fully constructed sling made from the component parts of FIG. 11.

In various embodiments, the fluid-impervious pouch 68 of FIG. 12 may be incorporated into any suitable sling and/or chassis using integrated transitions, discrete transitions, or combinations thereof. In various embodiments, the fluid-impervious pouch 68 of FIG. 12 may be incorporated into any suitable sling and/or chassis using only a transition joined with the front waist region, only a transition joined with the back waist region, or neither. In FIG. 13 the fluid-impervious pouch 68 of FIG. 12 is joined with the first transition 58 and the second transition 60 to define the sling 52. Referring now to FIGS. 11-13, the first transition 58 defines a first edge 82 and a second edge 84. Likewise, the second transition 60 defines a first edge 90 and a second edge 92. The base sheet 56 defines a first edge 86 and a second edge 88. The first edge 86 of the base sheet 56 is joined with the second edge 84 of the first transition 58 to define a first junction 72. Likewise, the second edge 88 of the base sheet 56 is joined with the first edge 90 of the second transition 60 to define a second junction 74.

Figure 15:
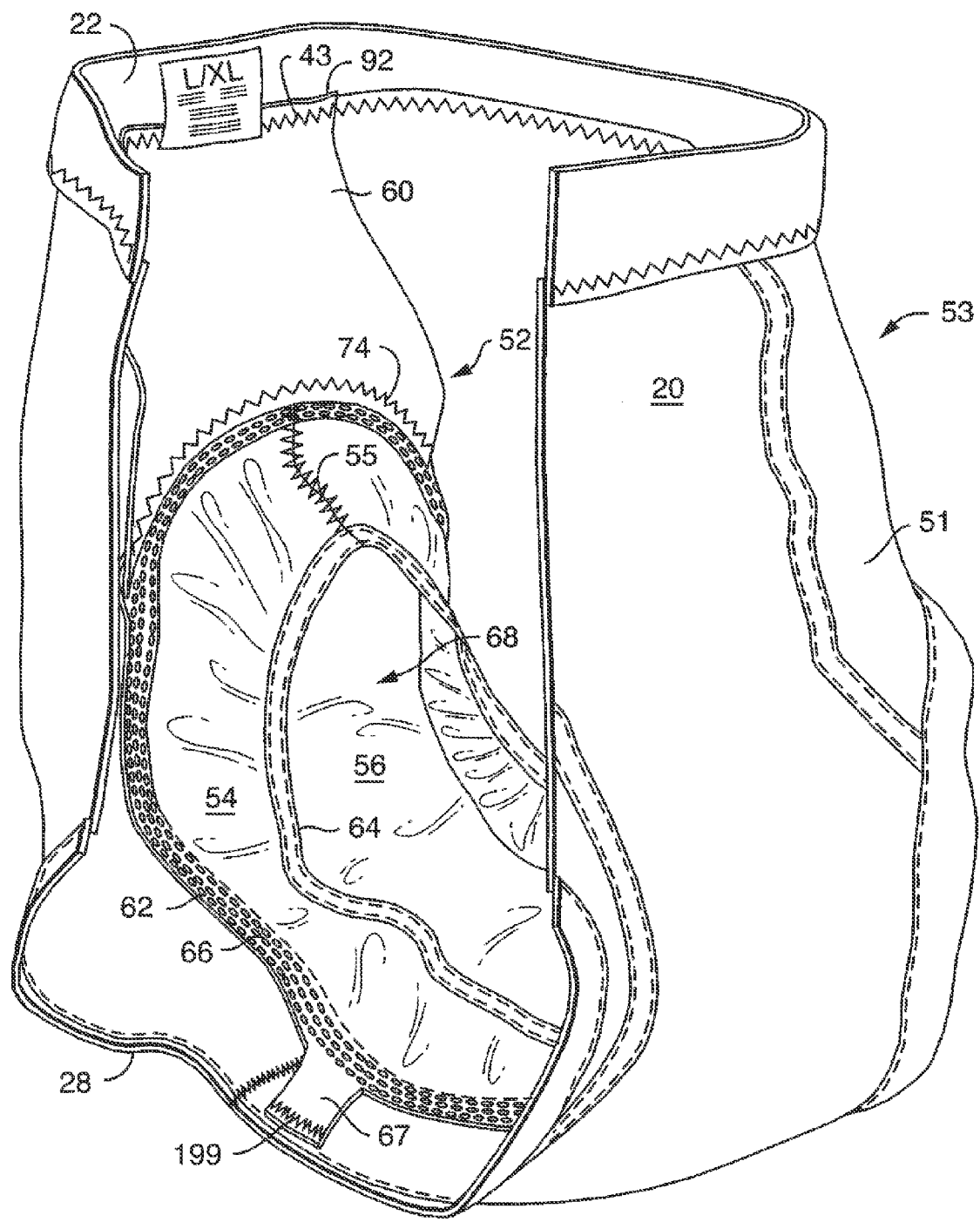
FIGS. 15 and 16 representatively illustrate side perspective views of the fully constructed sling of FIG. 13 incorporated in a chassis that is partially severed to illustrate internal structure.
Figure 16:
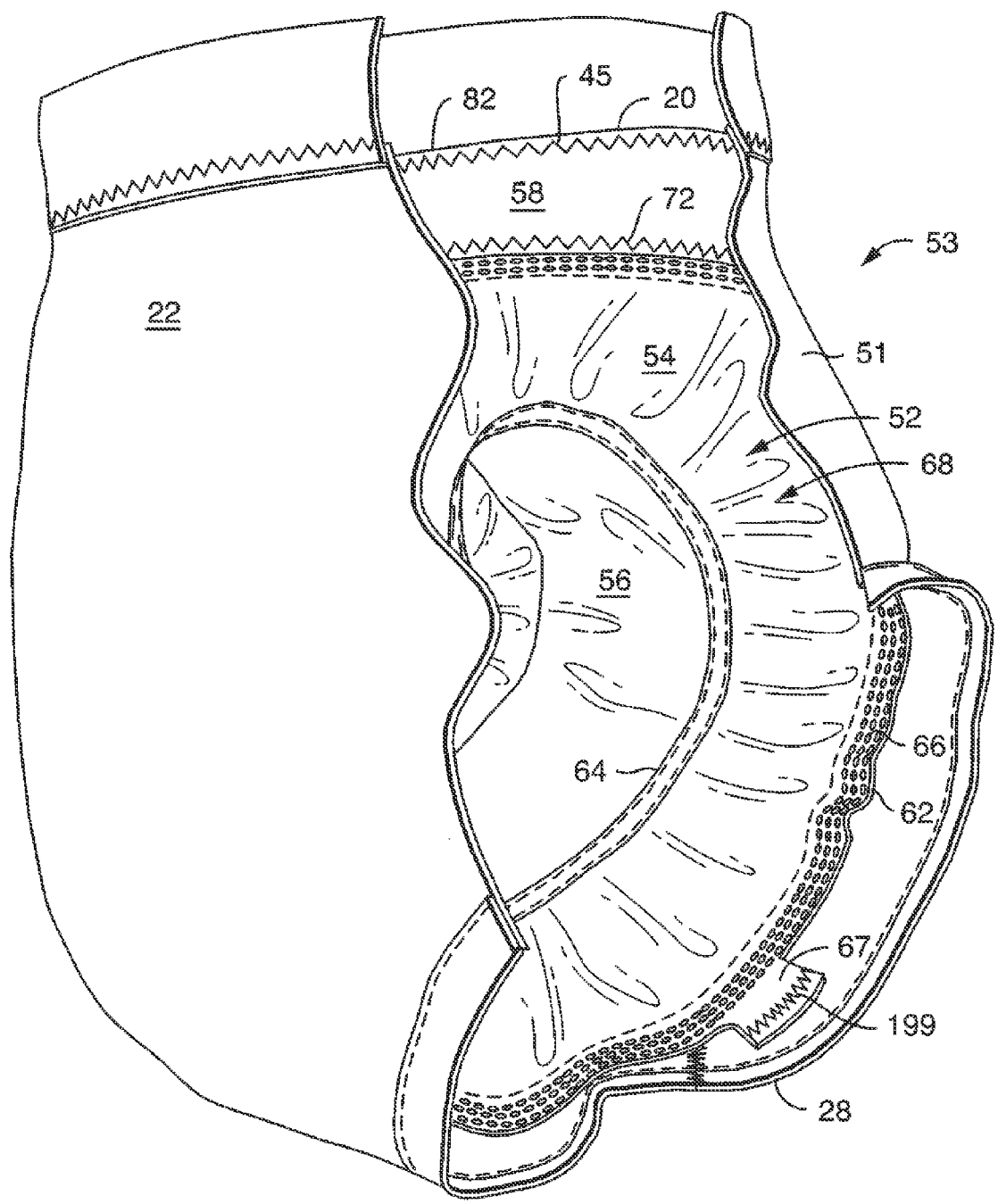

In various embodiments, the sling 52 of FIG. 13 can be joined with any suitable chassis to form a containment pant. In various embodiments, the sling 52 may be joined with a chassis such that the first transition is located in either the front waist region or the back waist region of the chassis and the second transition is located in the opposite region of the chassis. For example, referring now to FIGS. 15 and 16, an exemplary containment pant 53 having a chassis 51 and the sling 52 of FIG. 13 is representatively illustrated. FIG. 15 is a side perspective view of the containment pant 53 with the chassis 51 partially severed to illustrate the attachment of the sling 52 in the back waist region 22. Specifically, the second transition 60 is joined with the back waist region 22 of the chassis 51 at a back sling seam 43. FIG. 16 is a side perspective view of the containment pant 53 with the chassis 51 partially severed to illustrate the attachment of the sling 52 in the front waist region 20. Specifically, the first transition 58 is joined with the front waist region 20 of the chassis 51 at a front sling seam 45.

Figure 17:
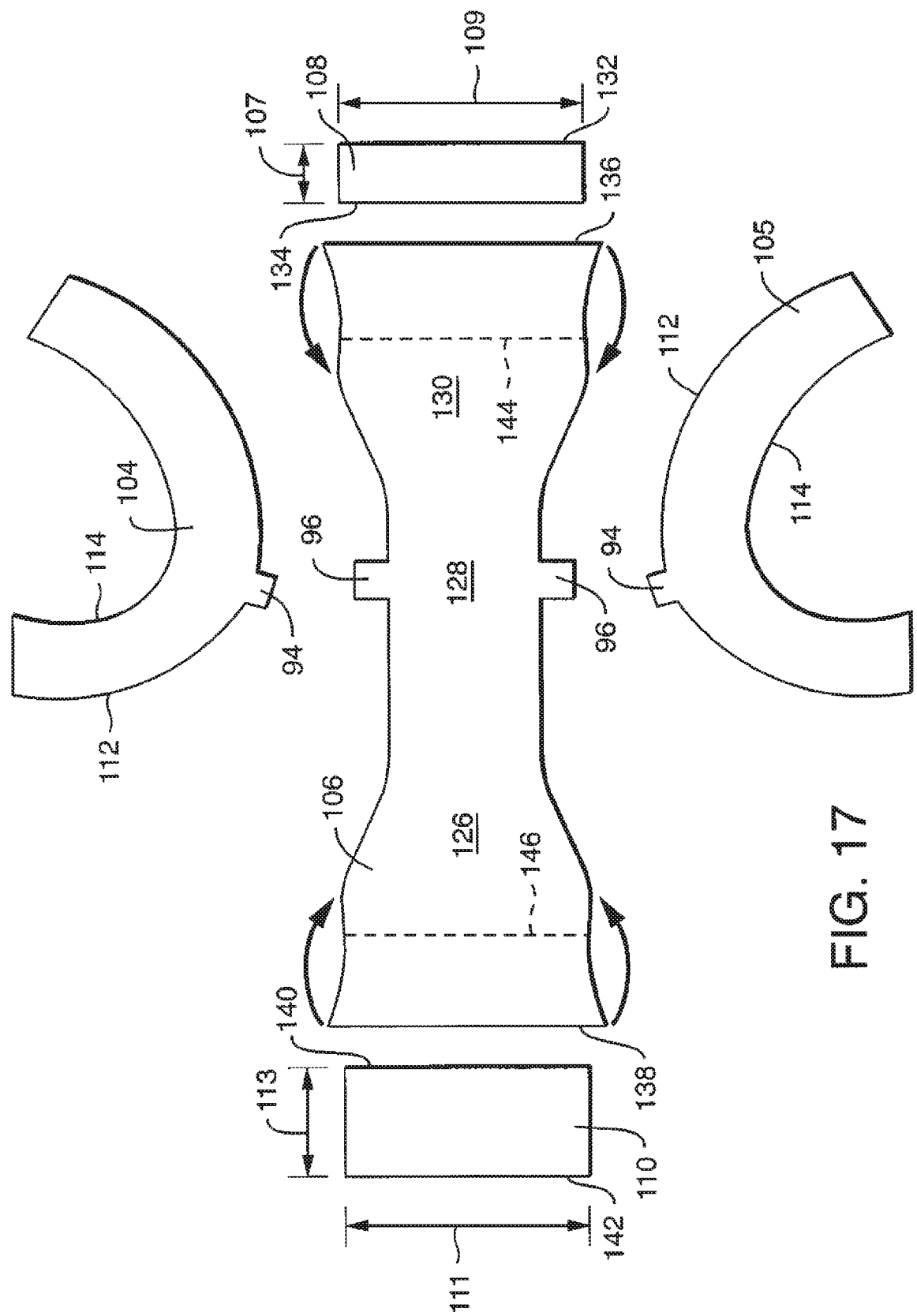
FIG. 17 representatively illustrates a top plan view of component parts of a second exemplary pouch and sling of the present invention.

In some embodiments, a sling and a fluid-impervious pouch may be constructed with a first containment flap, a second containment flap, a base sheet, a first transition, and a second transition. For example, referring now to FIG. 17, a top plan view of the component parts of another exemplary pouch and sling are representatively illustrated. A fully constructed pouch 118 made from some of the component parts of FIG. 17 is representatively illustrated in FIG. 18. A fully constructed sling 102 made from the component parts of FIG. 17 is representatively illustrated in FIG. 19. A cross sectional view of the sling 102 of FIG. 19 taken along the line B-B is representatively illustrated in FIG. 20.

Figure 18:
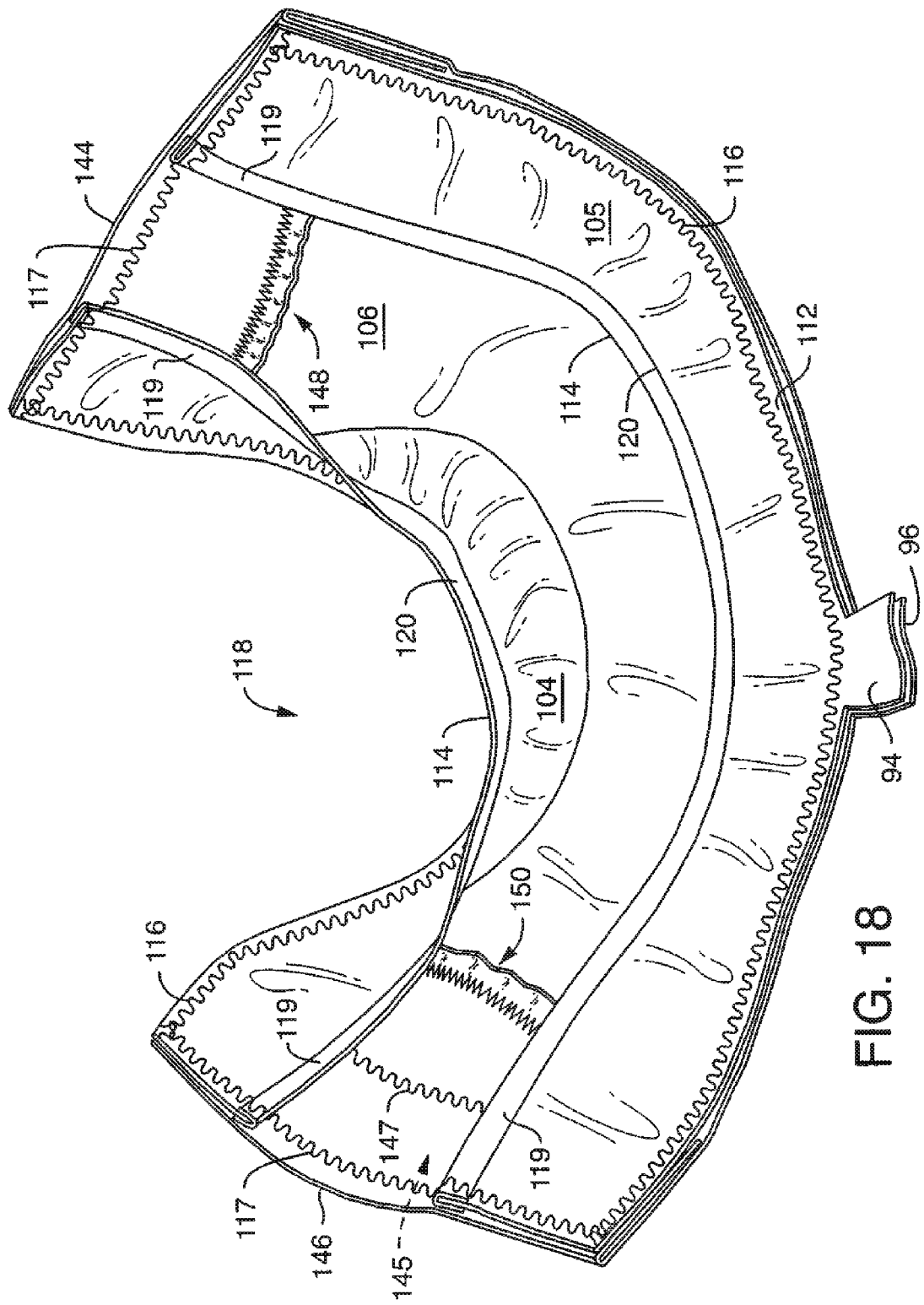
FIG. 18 representatively illustrates a fully constructed pouch made from the component parts of FIG. 17.
Figure 19:
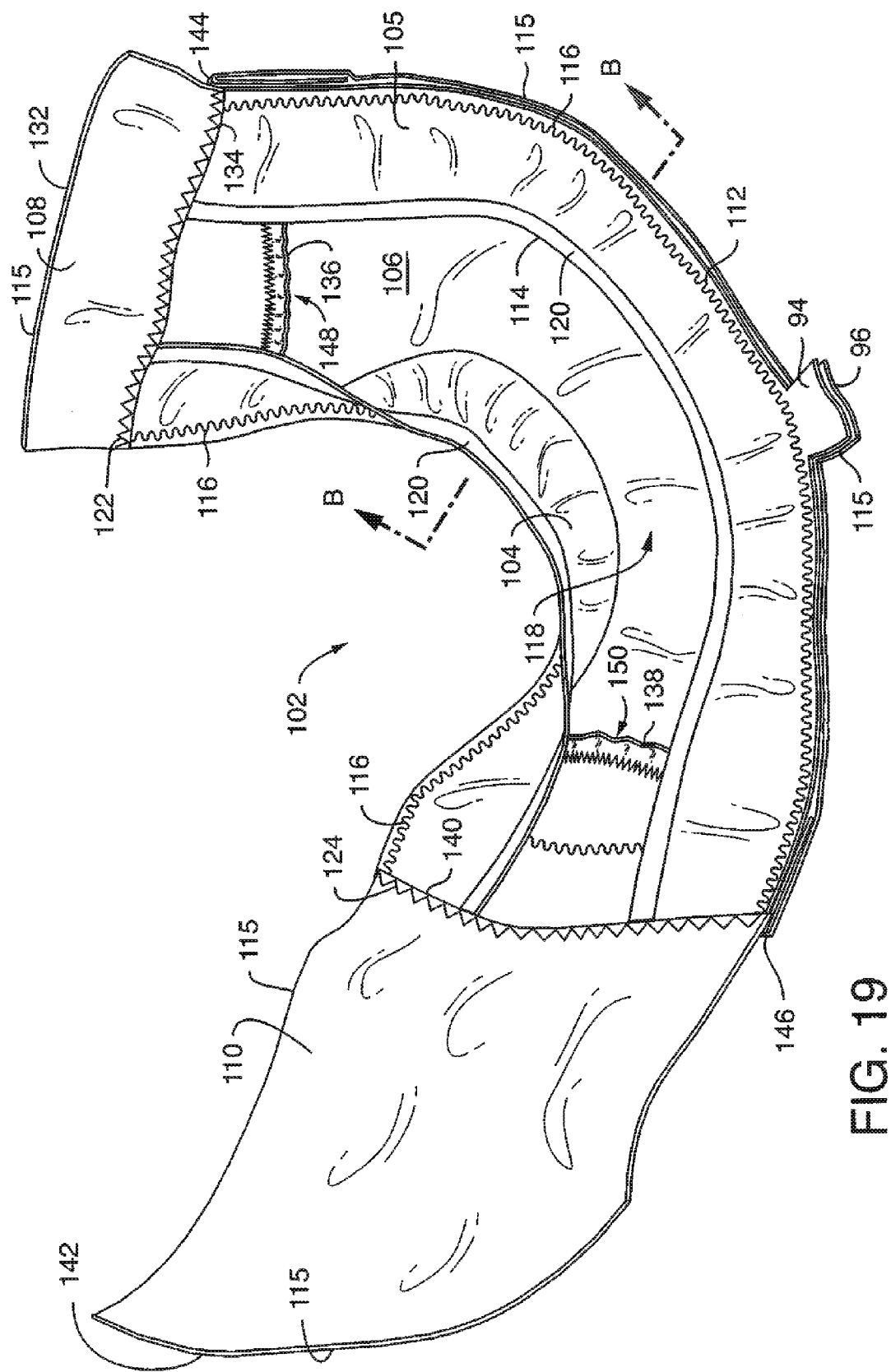
FIG. 19 representatively illustrates a fully constructed sling made from the component parts of FIG. 17.

The component parts include a first side containment flap 104, a second side containment flap 105, a base sheet 106, a first transition 108, and a second transition 110. The first side containment flap 104 and the second side containment flap 105 each define a proximal portion 112 and a distal portion 114. The first transition 108 defines a first edge 132 and a second edge 134. Likewise, the second transition 110 defines a first edge 140 and a second edge 142. The base sheet 106 defines a first edge 136 and a second edge 138. The first edge 136 of the base sheet 106 is folded along a first fold line 144 to define a first end containment flap 148 as illustrated in FIG. 18. Likewise, the second edge 138 of the base sheet 106 is folded along a second fold line 146 to define a second end containment flap 150 as illustrated in FIG. 18. The portion of the base sheet 106 proximate the first fold line 144 is joined with the second edge 134 of the first transition 108 to define a first junction 122 as illustrated in FIG. 19. Likewise, the portion of the base sheet 106 proximate the second fold line 146 is joined with the first edge 140 of the second transition 110 to define a second junction 124 as illustrated in FIG. 19.

In various embodiments, the side containment flaps may have a curve cut or a straight cut. For example, the first side containment flap 104 and the second side containment flap 105 of FIG. 17 are illustrated as having a curve cut. Similarly, the first side containment flap 330 and the second side containment flap 332 of FIG. 28 also illustrate a curve cut. In contrast, the containment flap 54 in FIG. 11 is exemplary of a straight cut flap. While not wishing to be bound by theory, it is believed that the curve cut containment flaps facilitate closer alignment with the natural curvature of the wearer's body. As such, it is believed that a more comfortable and better fit can be achieved.

The proximal portions 112 of each of the side containment flaps 104 and 105 are joined with the base sheet 106 and/or the first end containment flap 148 and/or the second end containment flap 150 to form containment flap seals 116 and to partially define a fluid-impervious pouch 118 as illustrated in FIG. 18. In various embodiments, one or both end flaps may be positioned between one or both of the containment flaps and the base sheet. In other embodiments, one or both of the containment flaps may be positioned between one or both of the end flaps and the base sheet. For example, in some embodiments, both end flaps may be positioned between both containment flaps and the base sheet as illustrated in FIG. 18. In other embodiments (not illustrated), both containment flaps may be positioned between both end flaps and the base sheet.

In various embodiments, the end flap may also include an end flap seal 117. The end flap seal 117 may join the first side containment flap 104 and/or the second side containment flap 105 to the first end containment flap 148 and/or the second end containment flap 150 and/or the base sheet 106 to define the fluid impervious pouch 118 in conjunction with the containment flap seals 116. In various embodiments, the overlap region 119 between the side containment flaps 104 and 105 and the end containment flaps 148 and 150 may be joined via any suitable manner to define a completely fluid impervious pouch 118. For example, in some embodiments, the side containment flaps 104 and 105 may be joined with the end containment flaps 148 and 150 in the overlap regions 119 by adhesive bonding, stitching, ultrasonic bonding, thermal bonding, pressure bonding, and the like, and combinations thereof. For example, the distal portions 114 of the first side containment flap 104 and the second side containment flap 105 may be completely joined with the end containment flaps 148 and 150 in the overlap regions 119 to ensure that the pouch 118 is completely fluid-impervious.

Figure 20:
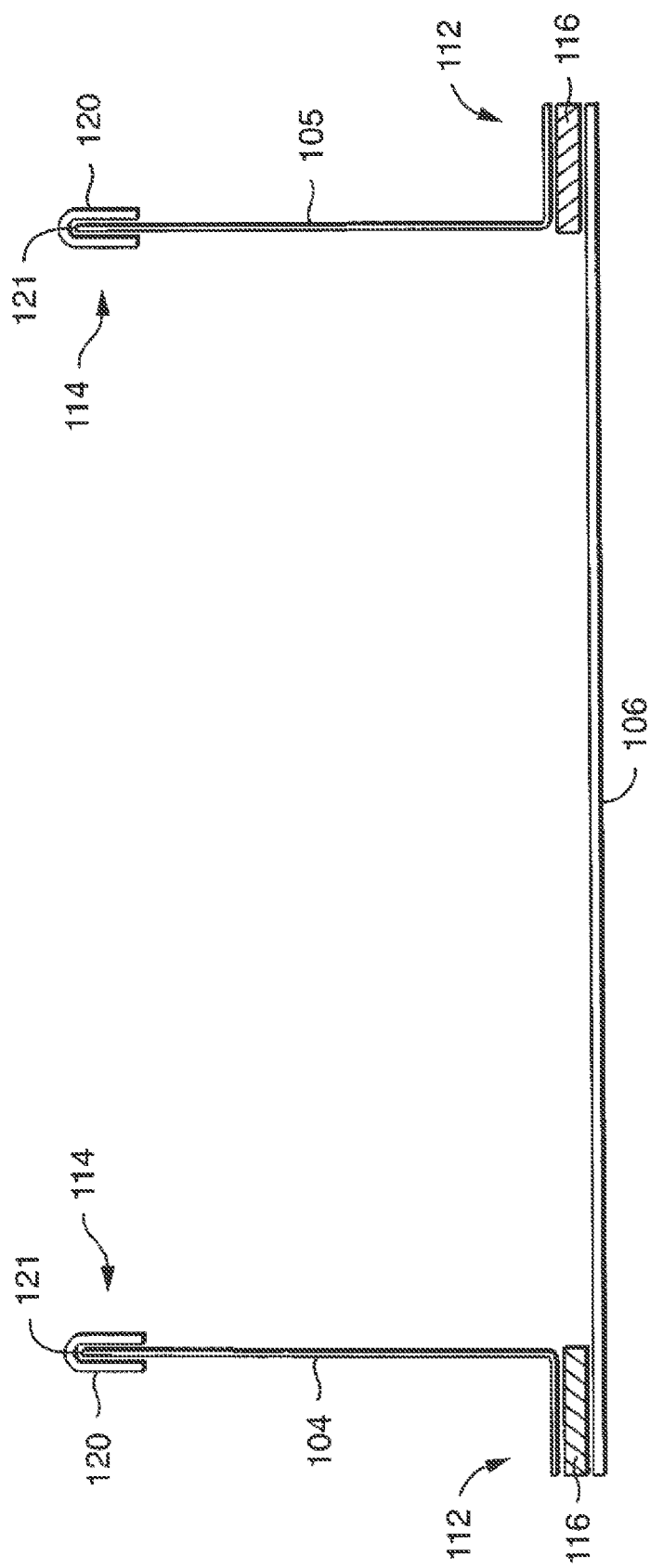
FIG. 20 representatively illustrates a cross-sectional view of the sling of FIG. 19 taken along the line B-B.

In various embodiments, any or all of the side containment flaps and/or the end containment flaps may further include one or more elastics. For example, the distal portions 114 of the side containment flaps 104 and 105 may further include containment flap elastic 120 as illustrated in FIG. 20.

In some embodiments, the first end containment flap and/or the second end containment flap may further include an insert stop that limits the depth to which an absorbent insert can be inserted. For example, the second end containment flap 150 of FIG. 18 is illustrated with an insert stop 147. In this embodiment, the insert stop 147 is illustrated as an ultrasonic bond between the second end containment flap 150 and the base sheet 106. In various embodiments, the insert stops may be any suitable length or width and may be positioned at any suitable depth within the first end containment pocket and/or the second end containment pocket. In some embodiments, the insert stop may extend from one containment flap seal to the other containment flap seal (not illustrated). In other embodiments, the insert stop 147 may terminate short of one or both containment flap seals 116 and thereby allow fluid within the second end containment pocket 150 to flow around the insert stop 147 and into a reservoir 145. In effect, this configuration provides greater volume for containing insults while still providing a suitably sized pocket for retention of the absorbent insert.

In various embodiments, the fluid-impervious pouch 118 of FIG. 18 may be incorporated into any suitable sling and/or chassis using integrated transitions, discrete transitions, or combinations thereof. In various embodiments, the fluid-impervious pouch 118 of FIG. 18 may be incorporated into any suitable sling and/or chassis using only a transition joined with the front waist region, only a transition joined with the back waist region, or neither. In the illustrated embodiment, the fluid-impervious pouch 118 of FIG. 18 is joined with the first transition 108 and the second transition 110 to define the sling 102 of FIG. 19.

Figure 21:
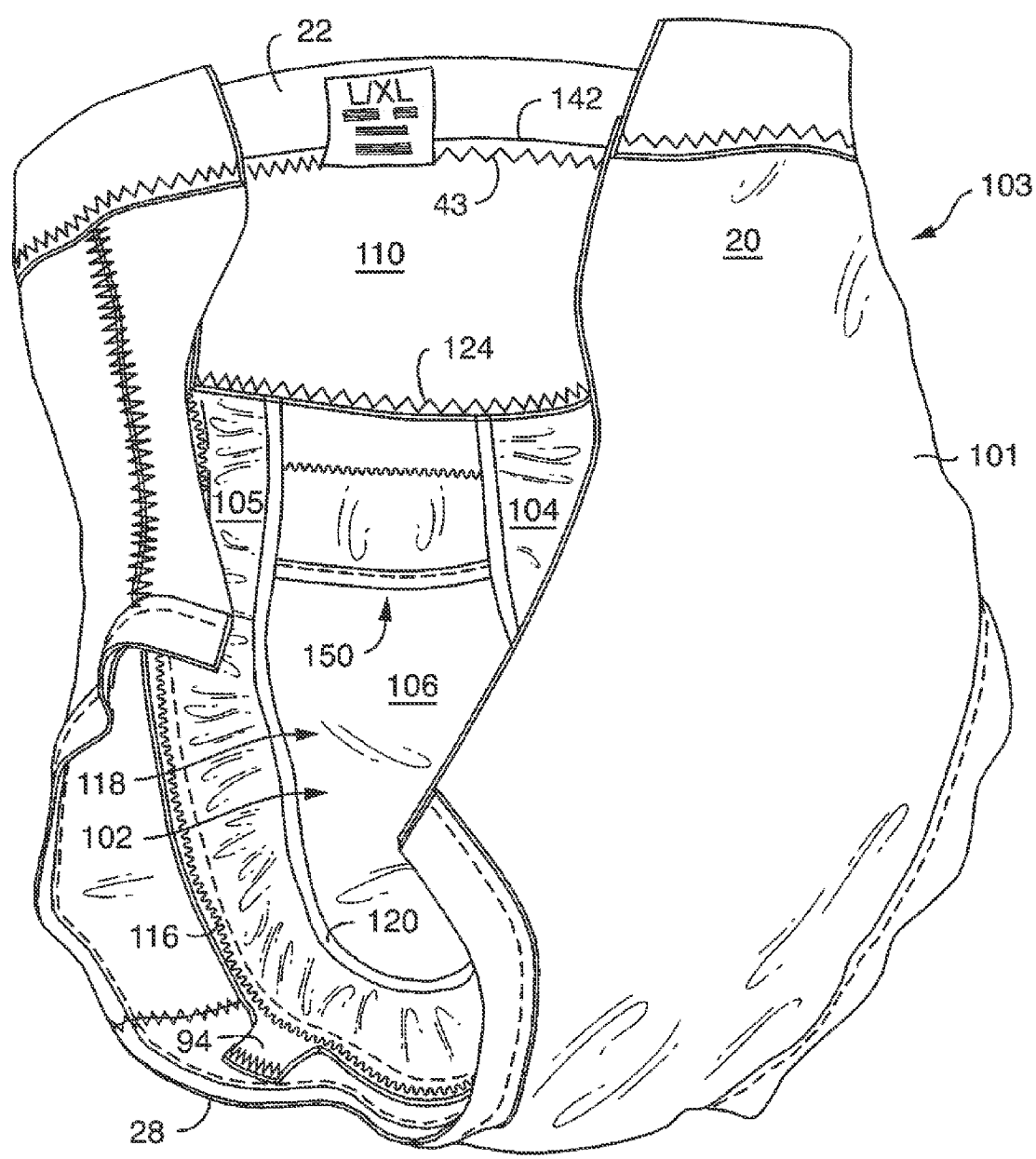
FIGS. 21 and 22 representatively illustrate side perspective views of the fully constructed sling of FIG. 19 incorporated in a chassis that is partially severed to illustrate internal structure.
Figure 22:
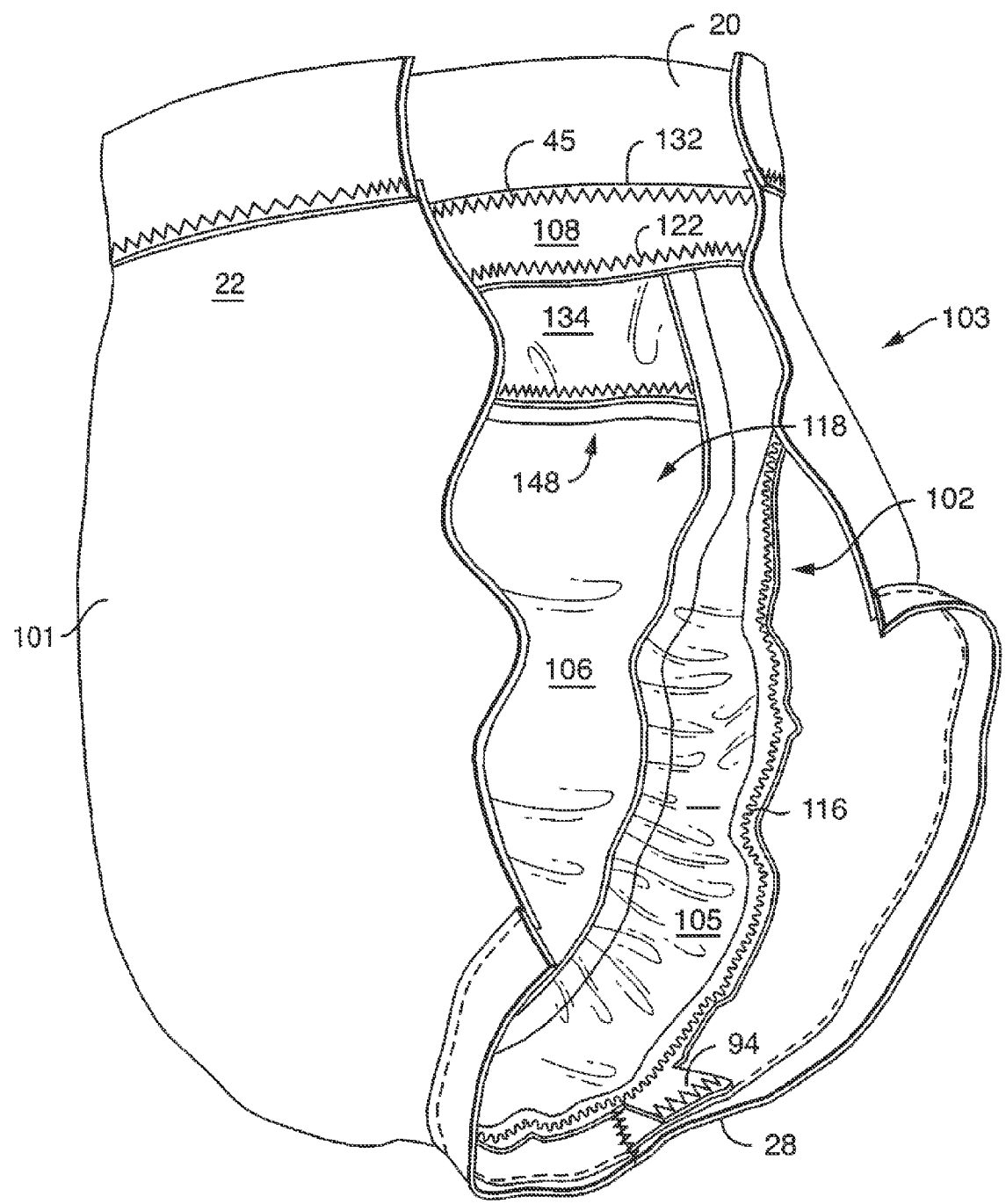

In various embodiments, the sling 102 of FIG. 19 can be joined with any suitable chassis to form a containment pant. In various embodiments, the sling 102 may be joined with a chassis such that the first transition is located in either the front waist region or the back waist region of the chassis and the second transition is located in the opposite region of the chassis. For example, referring now to FIGS. 21 and 22, an exemplary containment pant 103 having a chassis 101 and the sling 102 is representatively illustrated. FIG. 21 is a side perspective view of the containment pant 103 with the chassis 101 partially severed to illustrate the attachment of the sling 102 in the back waist region 22. Specifically, the second transition 110 is joined with the back waist region 22 of the chassis 101 at a back sling seam 43. FIG. 22 is a side perspective view of the containment pant 103 with the chassis 101 partially severed to illustrate the attachment of the sling 102 in the front waist region 20. Specifically, the first transition 108 is joined with the front waist region 20 of the chassis 101 at a front sling seam 45.

Figure 23:
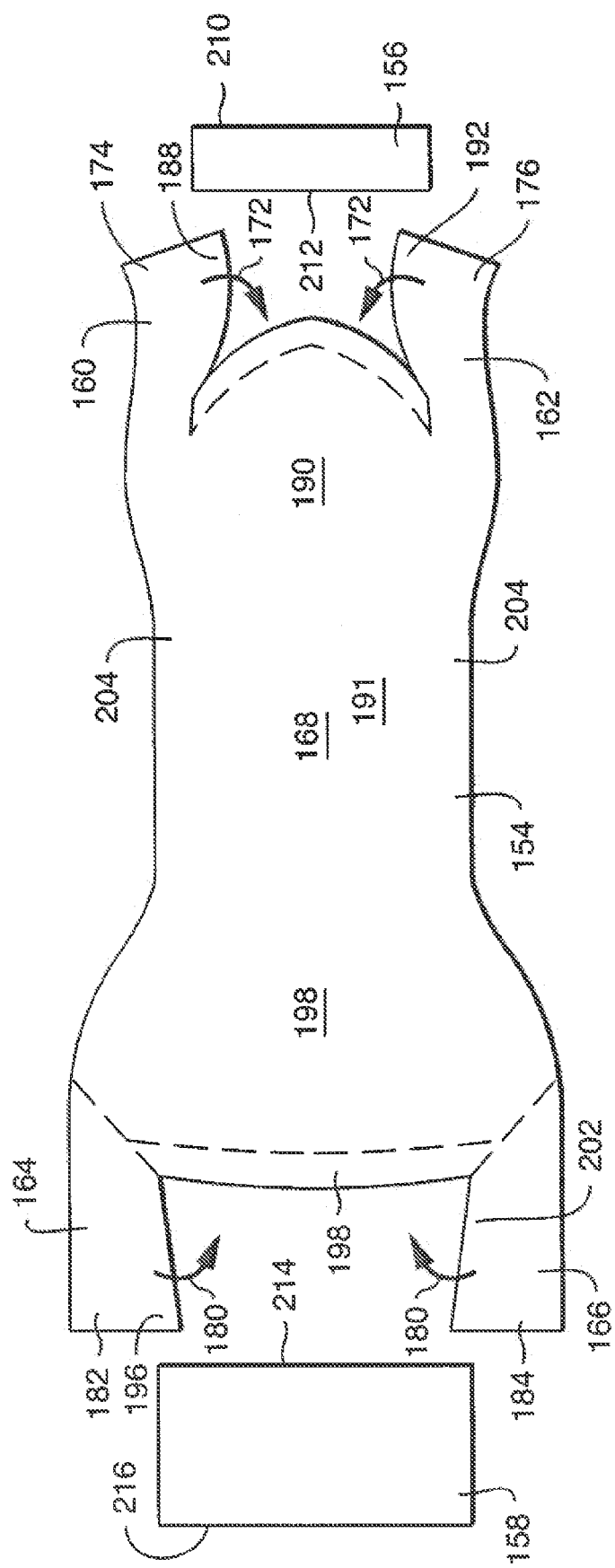
FIG. 23 representatively illustrates a top plan view of component parts of a third exemplary pouch and sling of the present invention.

In another embodiment, a sling and a fluid-impervious pouch may be constructed with a base sheet, a first transition, and a second transition. For example, referring now to FIG. 23, a top plan view of the component parts of another exemplary pouch and sling are representatively illustrated. A fully constructed pouch 206 made from some of the component parts of FIG. 23 is representatively illustrated in FIG. 24. A fully constructed sling 152 made from the component parts of FIG. 23 is representatively illustrated in FIG. 25. The component parts include a base sheet 154, a first transition 156, and a second transition 158. The base sheet 154 includes a first arm 160, a second arm 162, a third arm 164, and a fourth arm 166. The base sheet 154 defines an absorbent facing surface 168 and a chassis facing surface 170.

Figure 24:
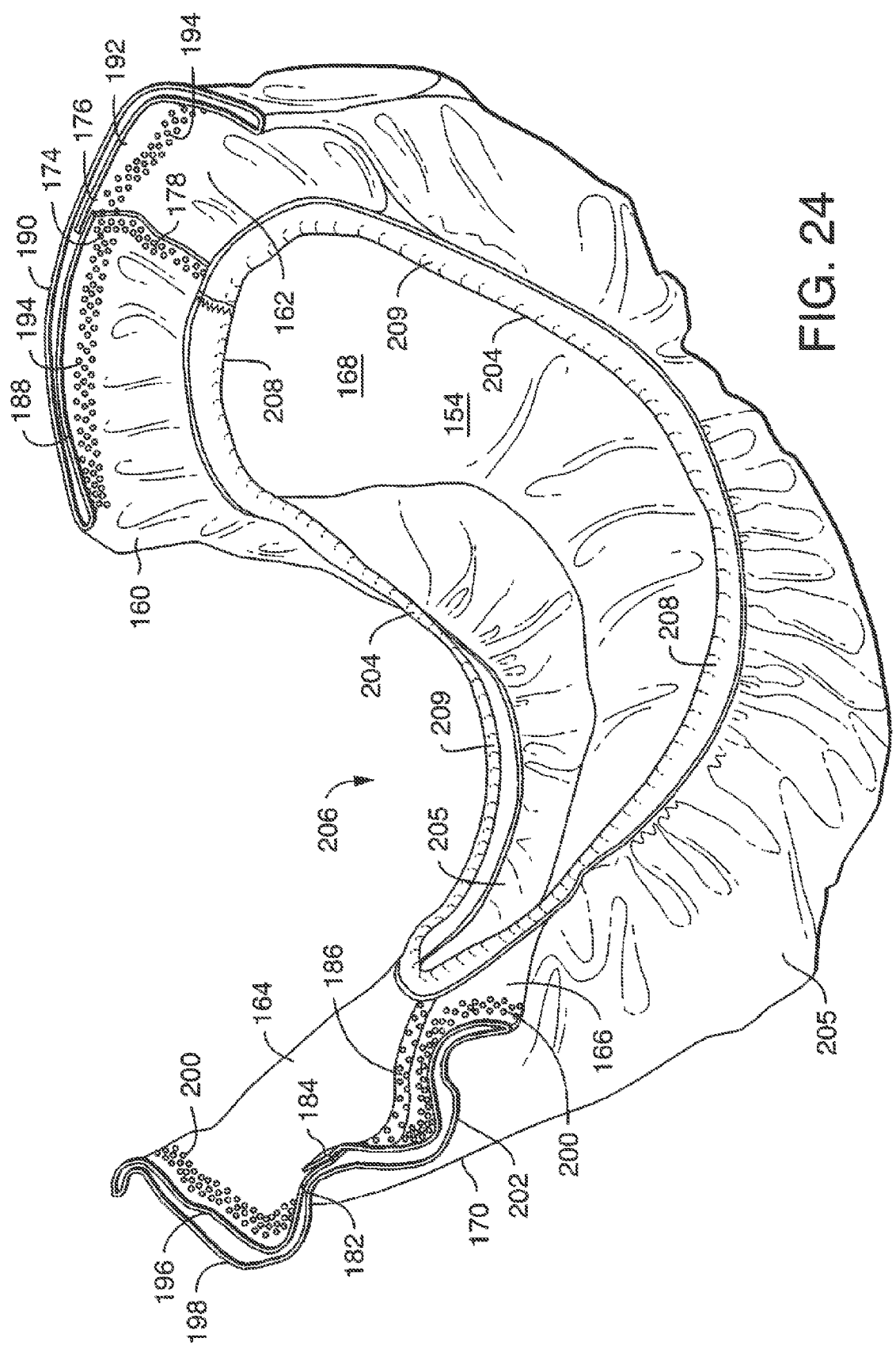
FIG. 24 representatively illustrates a fully constructed pouch made from the component parts of FIG. 23.

Referring now to FIGS. 23 and 24, the first arm 160 and the second arm 162 are folded towards the absorbent facing surface 168 of the base sheet 154 in the direction indicated by arrows 172. A distal portion 174 of the first arm 160 is joined with a distal portion 176 of the second arm 162 to define a first bridging seam 178. Likewise, the third arm 164 and the fourth arm 166 are folded towards the absorbent facing surface 168 of the base sheet 154 in the direction indicated by arrows 180. A distal portion 182 of the third arm 164 is joined with a distal portion 184 of the fourth arm 166 to define a second bridging seam 186. An inner portion 188 of the first arm 160 is joined with a first portion 190 of the base sheet 154 to define a portion of a first containment seam 194. Likewise, an inner portion 192 of the second arm 162 is joined with the first portion 190 of the base sheet 154 to define the remainder of the first containment seam 194. An inner portion 196 of the third arm 164 is joined with a second portion 198 of the base sheet 154 to define a portion of a second containment seam 200. Likewise, an inner portion 202 of the fourth arm 166 is joined with the second portion 198 of the base sheet 154 to define the remainder of the second containment seam 200.

By folding the first arm 160 and the second arm 162 in the direction indicated by arrows 172, the lateral side edges 204 of the base sheet 154 tend to bend towards the absorbent facing surface 168 of the base sheet 154. Similarly, by folding the third arm 164 and the fourth arm 166 in the direction indicated by arrows 180, the lateral side edges 204 of the base sheet 154 tend to bend in the same manner to define containment flap 205. As such, the base sheet 154 is cupped to define a fluid-impervious pouch 206 having containment flap 205 as illustrated in FIG. 24.

Figure 25:
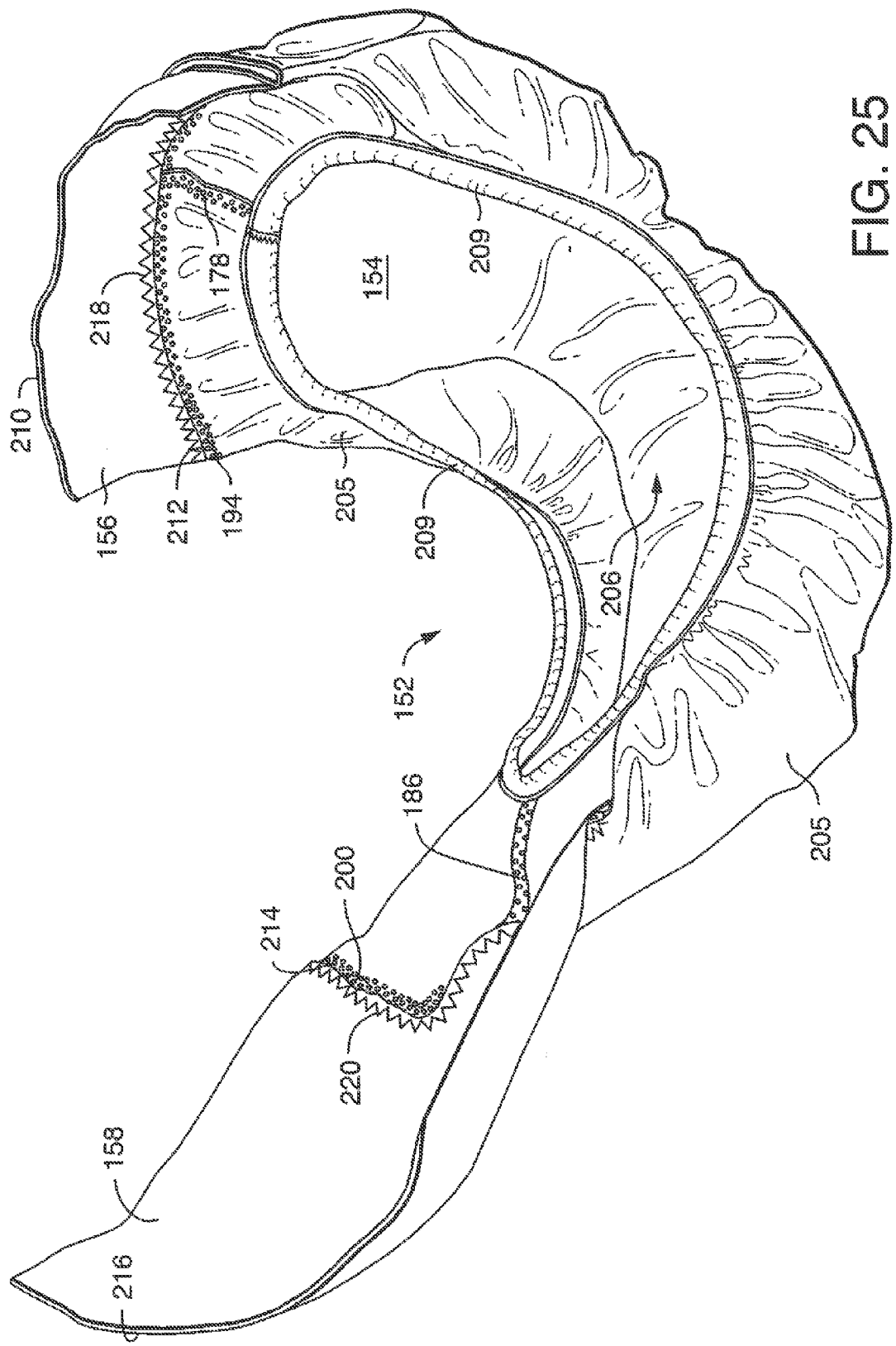
FIG. 25 representatively illustrates a fully constructed sling made from the component parts of FIG. 23.

In various embodiments, the fluid-impervious pouch 206 of FIG. 24 may be incorporated into any suitable sling and/or chassis using integrated transitions, discrete transitions, or combinations thereof. In various embodiments, the fluid-impervious pouch 206 of FIG. 24 may be incorporated into any suitable sling and/or chassis using only a transition joined with the front waist region, only a transition joined with the back waist region, or neither. In the illustrated embodiment, the fluid-impervious pouch 206 is joined with the first transition 156 and the second transition 158 to define the sling 152 as illustrated in FIG. 25. In this embodiment, the first transition 156 defines a first edge 210 and a second edge 212 and the second transition 158 defines a first edge 214 and a second edge 216. The first portion 190 of the base sheet 154 is joined with the second edge 212 of the first transition 156 to define a first junction 218. Likewise, the second portion 198 of the base sheet 154 is joined with the first edge 214 of the second transition 158 to define a second junction 220. In some embodiments, the fluid-impervious pouch 206 may define a distal edge and may include one or more elastics. For example, as illustrated in FIG. 24, the distal edge 208 of the pouch 206 further includes a pouch elastic 209.

Figure 26:
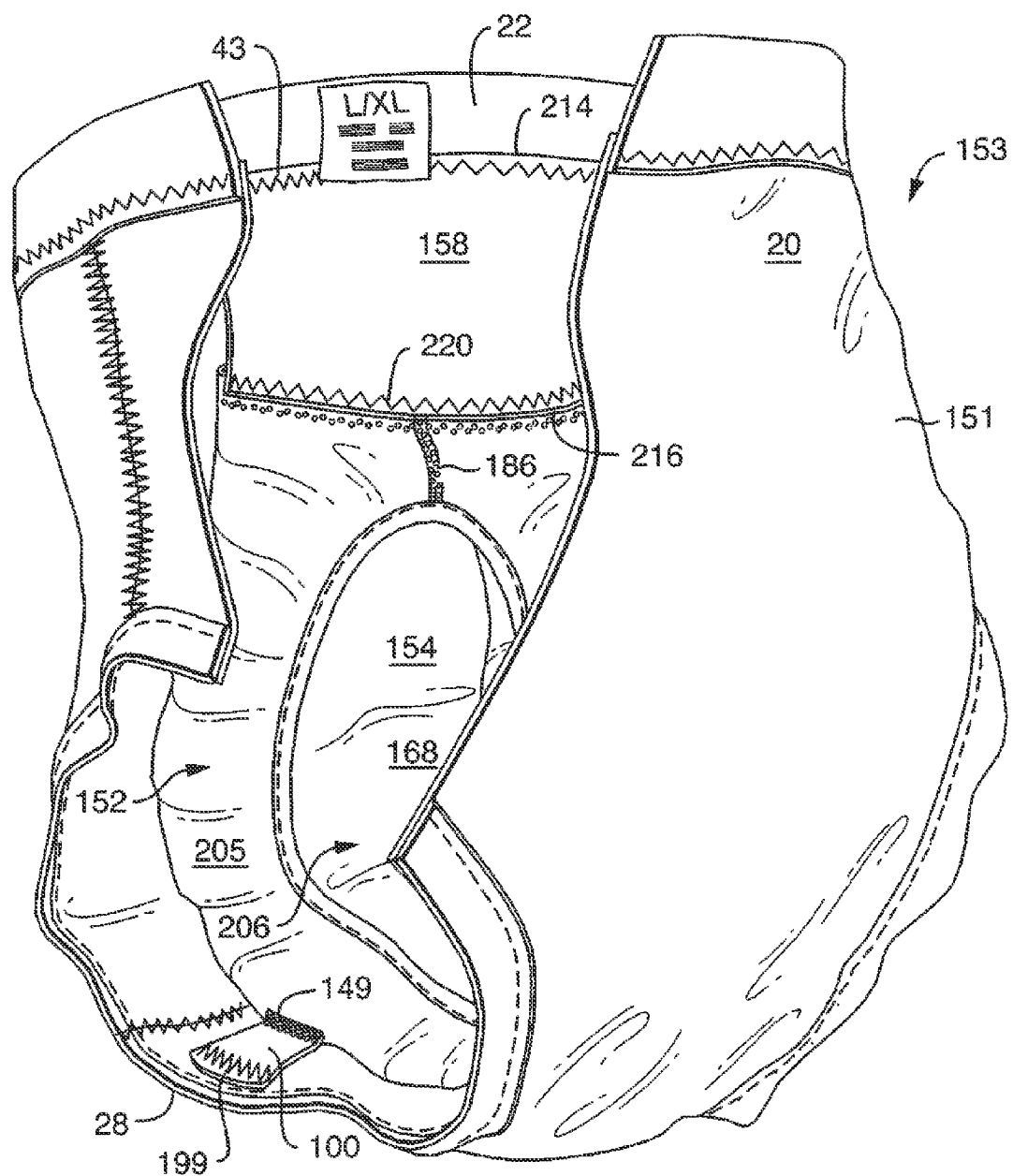
FIGS. 26 and 27 representatively illustrate side perspective views of the fully constructed sling of FIG. 25 incorporated in a chassis that is partially severed to illustrate internal structure.
Figure 27:
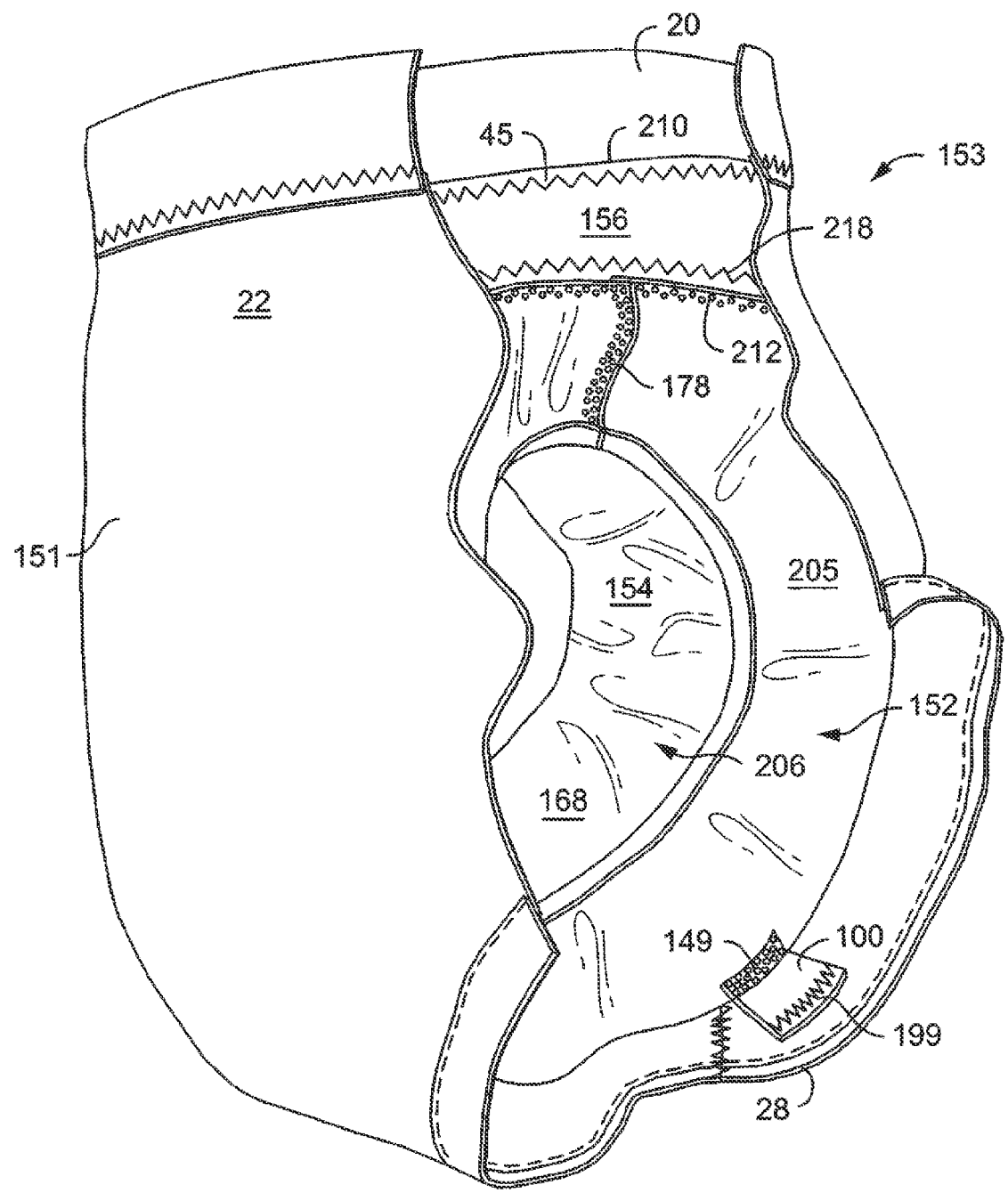

In various embodiments, the sling 152 of FIG. 25 can be joined with any suitable chassis to form a containment pant. In various embodiments, the sling 152 may be joined with a chassis such that the first transition is located in either the front waist region or the back waist region of the chassis and the second transition is located in the opposite region of the chassis. For example, referring now to FIGS. 26 and 27, an exemplary containment pant 153 having a chassis 151 and the sling 152 is representatively illustrated. FIG. 26 is a side perspective view of the containment pant 153 with the chassis 151 partially severed to illustrate the attachment of the sling 152 in the back waist region 22. Specifically, the second transition 158 is joined with the back waist region 22 of the chassis 151 at a back sling seam 43. FIG. 27 is a side perspective view of the containment pant 153 with the chassis 151 partially severed to illustrate the attachment of the sling 152 in the front waist region 20. Specifically, the first transition 156 is joined with the front waist region 20 of the chassis 151 at a front sling seam 45.

Figure 28:
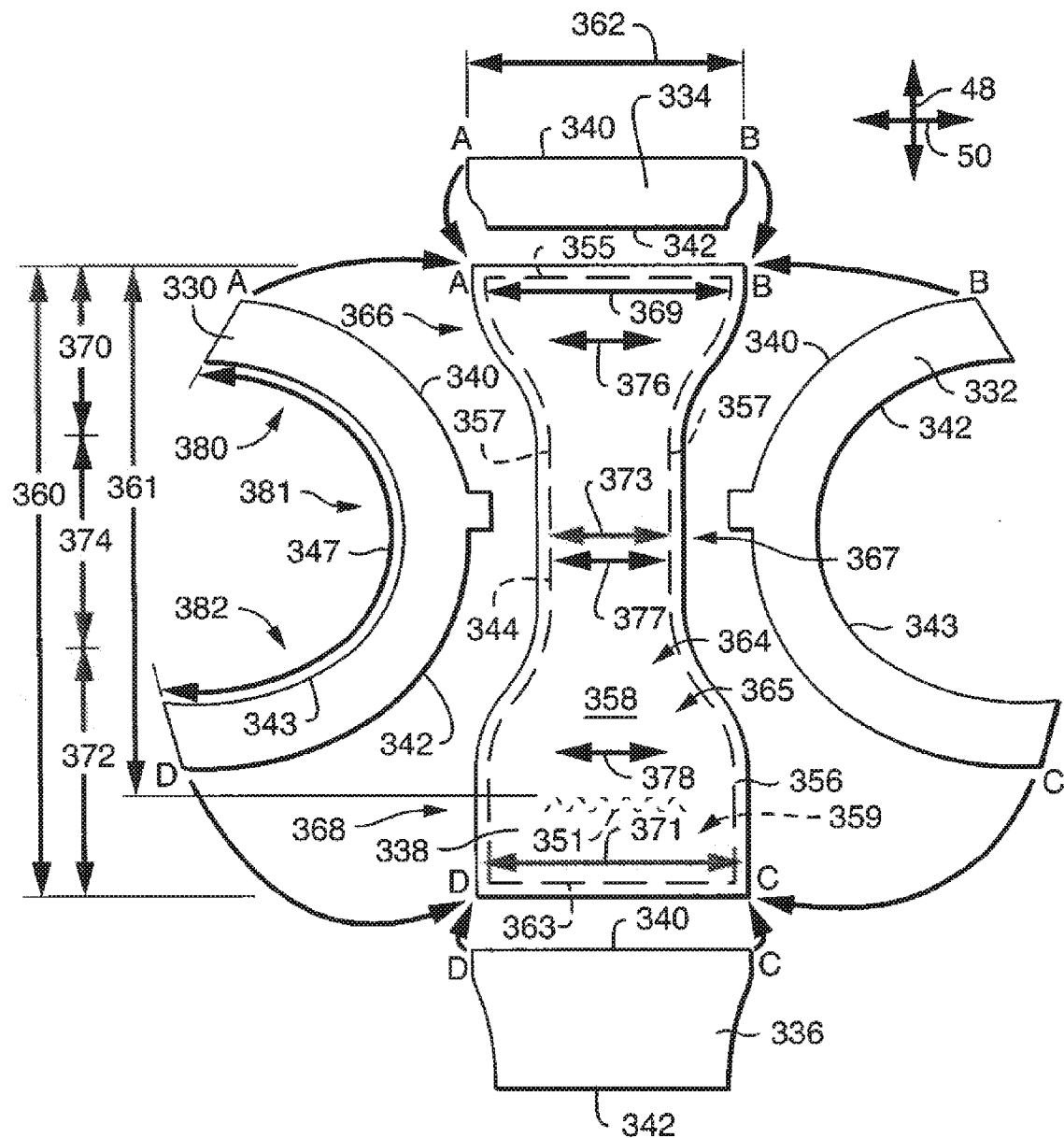
FIG. 28 representatively illustrates a top plan view of component parts of another exemplary pouch and sling of the present invention.

In another embodiment, a fluid-impervious pouch may be constructed with a first containment flap, a second containment flap, a third containment flap, a fourth containment flap, and a base sheet. For example, referring now to FIG. 28, a top plan view of the component parts of another exemplary pouch are representatively illustrated. A fully constructed pouch 346 made from the component parts of FIG. 28 is representatively illustrated in FIG. 29.

The component parts include a first side containment flap 330, a second side containment flap 332, a first end containment flap 334, a second end containment flap 336, and a base sheet 338. The containment flaps 330, 332, 334, and 336 each define a proximal portion 340 and a distal portion 342.

Figure 29:
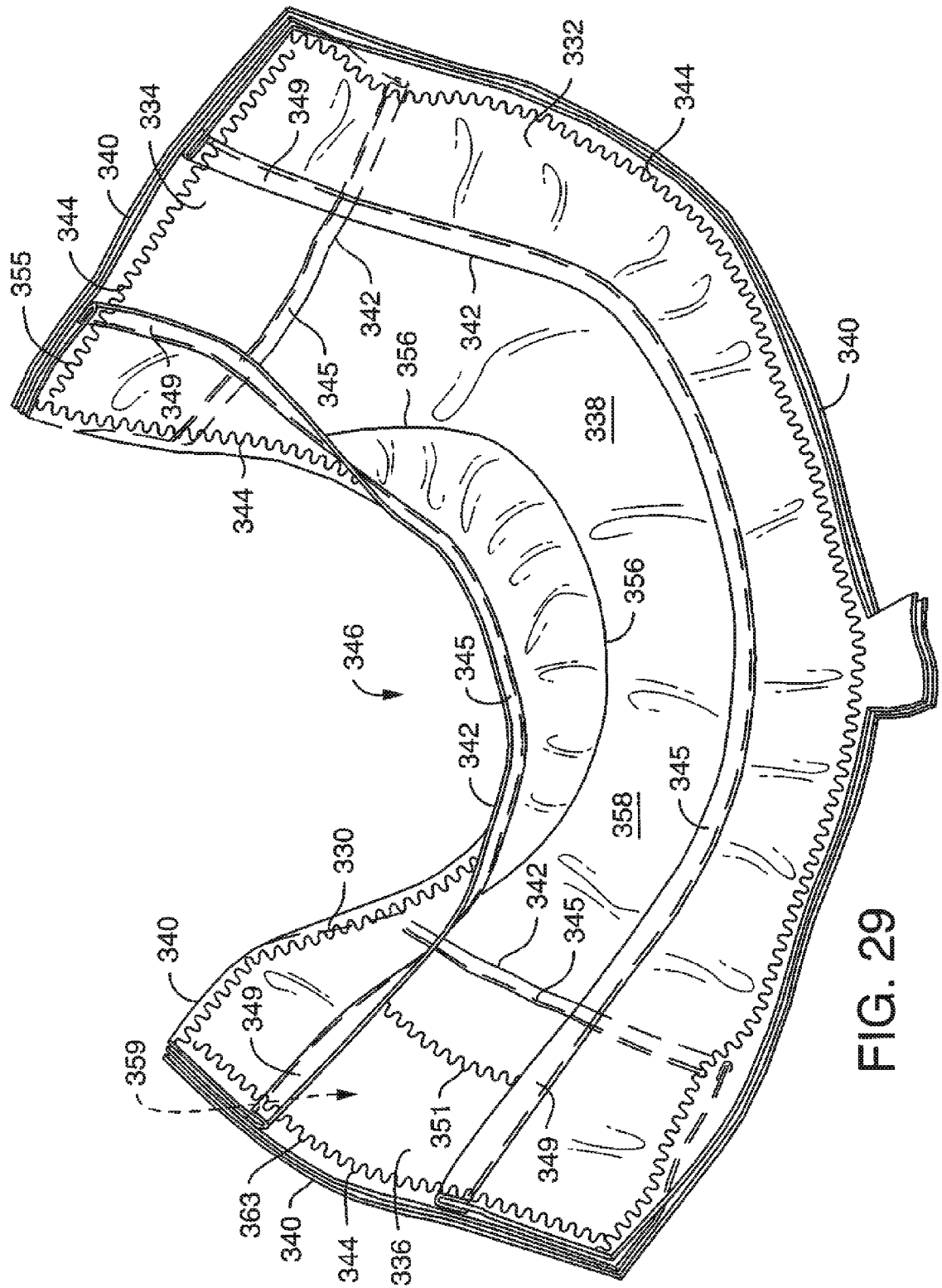
FIG. 29 representatively illustrates a fully constructed pouch made from the component parts of FIG. 28.

The proximal portions 340 of each of the containment flaps 330, 332, 334, and 336 are joined with the base sheet 338 to form containment flap seals 344 and to define a fluid-impervious pouch 346 as illustrated in FIG. 29. In various embodiments, one or both end flaps may be positioned between one or both of the containment flaps and the base sheet. In other embodiments, one or both of the containment flaps may be positioned between one or both of the end flaps and the base sheet. For example, in some embodiments, both end flaps may be positioned between both containment flaps and the base sheet as illustrated in FIG. 29. In other embodiments (not illustrated), both containment flaps may be positioned between both end flaps and the base sheet.

In various embodiments, the overlap region 349 between the side containment flaps 330 and 332 and the end containment flaps 334 and 336 may be joined together via any suitable manner to at least partially define the completely fluid impervious pouch 346. For example, in some embodiments, the side containment flaps 330 and 332 may be joined with the end containment flaps 334 and 336 in the overlap regions 349 by adhesive bonding, stitching, ultrasonic bonding, thermal bonding, pressure bonding, and the like, and combinations thereof. For example, the distal portions 342 of the first side containment flap 330 and the second side containment flap 332 may be completely joined with the end containment flaps 334 and 336 in the overlap regions 349 to ensure that the pouch 346 is completely fluid-impervious. In other embodiments, the distal portions of the first end containment flap and the second end containment flap may be completely joined with the side containment flaps in the overlap region to ensure the pouch is completely fluid-impervious (not shown).

In various embodiments, one or more of the containment flaps may further include one or more elastics. For example, the distal portions 342 of the containment flaps 330, 332, 334, and 336 may further include containment flap elastic 345. In various embodiments, the fluid-impervious pouch 346 of FIG. 29 may be incorporated into any suitable sling and/or chassis using integrated transitions, discrete transitions, or combinations thereof. In various embodiments, the fluid-impervious pouch 346 of FIG. 29 may be incorporated into any suitable sling and/or chassis using only a transition joined with the front waist region, only a transition joined with the back waist region, or neither.

Figure 30:
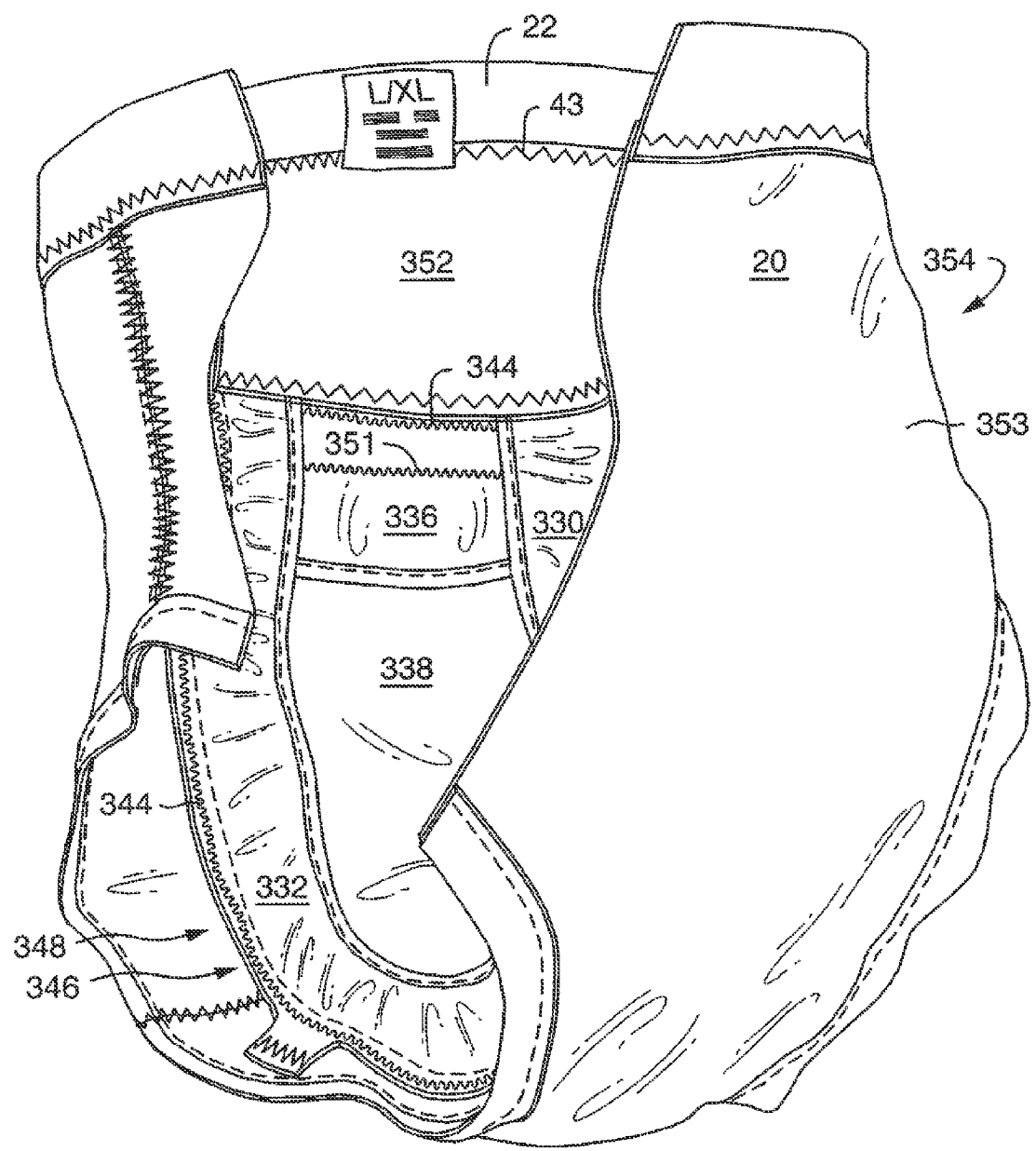
FIGS. 30 and 31 representatively illustrate side perspective views of the fully constructed pouch of FIG. 29 incorporated in a chassis that is partially severed to illustrate internal structure.
Figure 31:
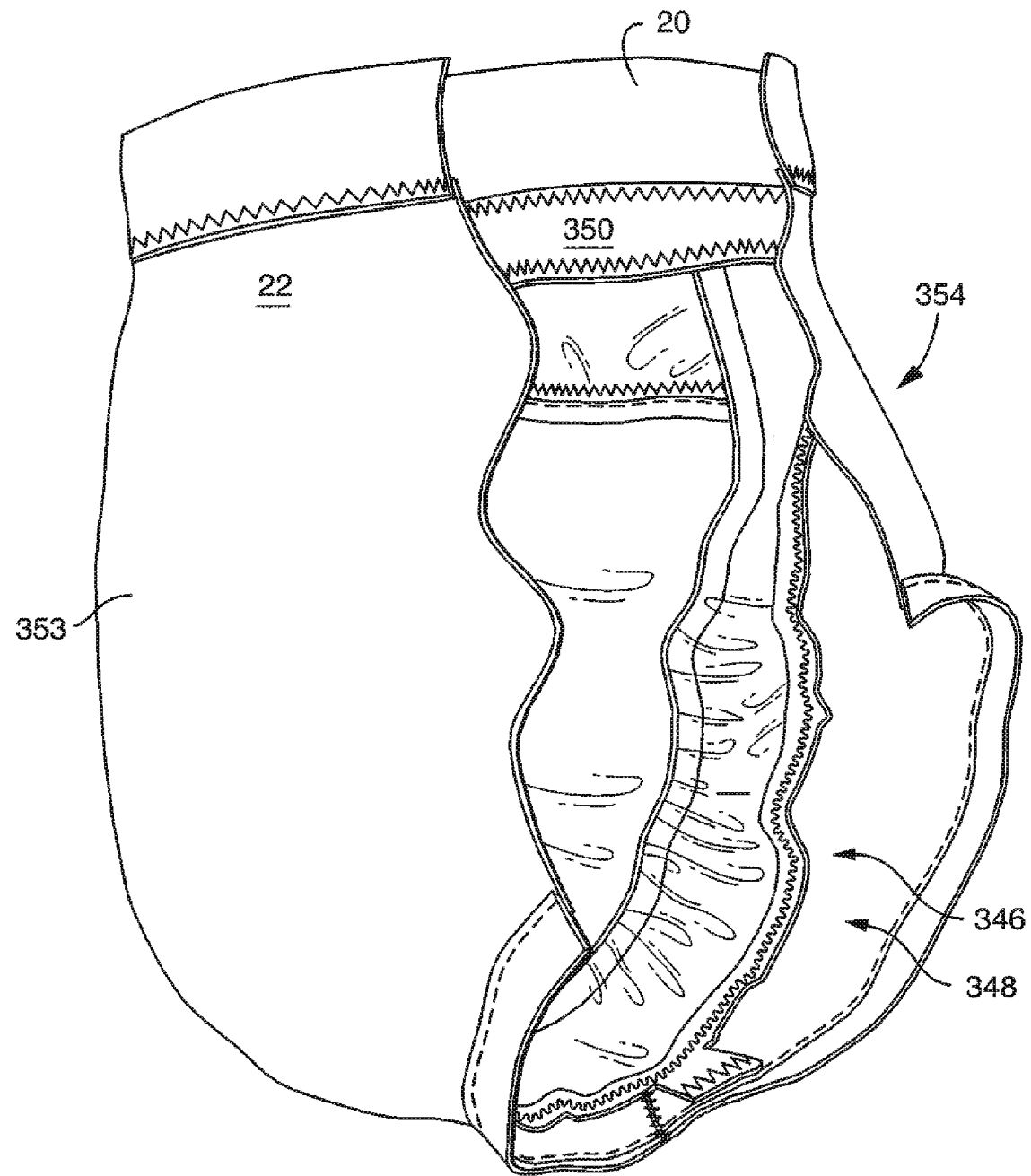

Referring now to FIGS. 30 and 31, the fluid-impervious pouch 346 of FIG. 29 is joined with a first transition 350 and a second transition 352 to define a sling 348 suspended within an exemplary containment pant 354. In various embodiments, the pouch 346 can be joined within any suitable chassis to form a containment pant. In various embodiments, the pouch 346 may be joined with a chassis via a first transition that is located in either the front waist region or the back waist region of the chassis and via a second transition that is located in the opposite region of the chassis. FIG. 30 is a side perspective view of the containment pant 354 with the chassis 353 partially severed to illustrate the attachment of the pouch 346 in the back waist region 22 via the second transition 352. The second transition 352 is joined with the back waist region 22 of the chassis 353 at a back sling seam 43. FIG. 31 is a side perspective view of the containment pant 354 with the chassis 353 partially severed to illustrate the attachment of the pouch 346 in the front waist region 20 via the first transition 350. In the illustrated embodiment, the first transition 350 is a discrete piece of material joined with the front waist region 20 of the chassis 353 while the second transition 352 is a discrete piece of material joined with the back waist region 22 of the chassis 353.

Figure 32:
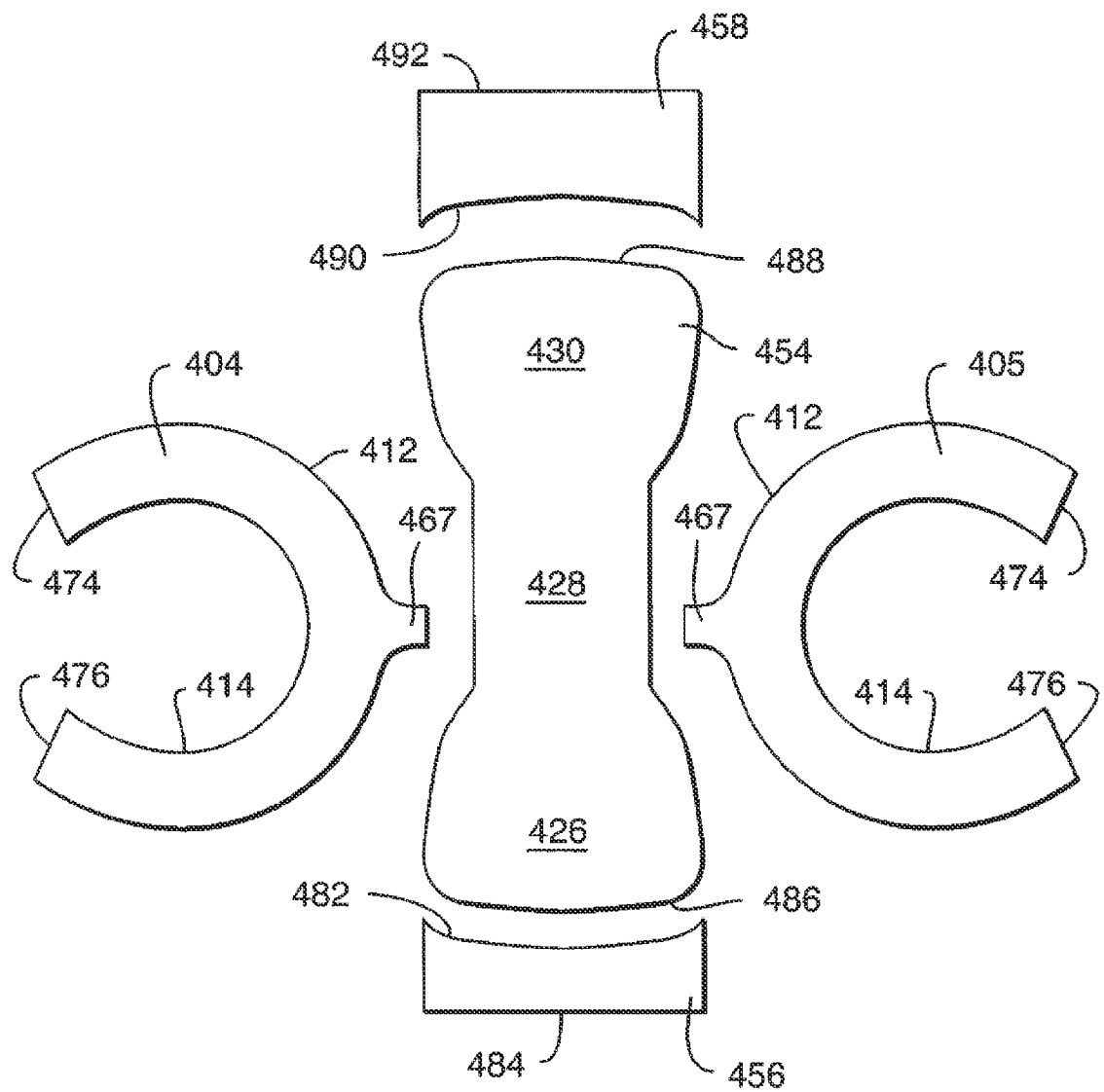
FIG. 32 representatively illustrates a top plan view of component parts of another exemplary pouch and sling of the present invention.

In another desirable embodiment, a sling and a fluid-impervious pouch may be constructed with a first containment flap, a second containment flap, a base sheet, a first transition, and a second transition. For example, referring now to FIG. 32, a top plan view of the component parts of another exemplary pouch and sling are representatively illustrated. A fully constructed sling 452 made from the component parts of FIG. 32 is representatively illustrated in FIG. 33. The component parts include a first side containment flap 404, a second side containment flap 405, a base sheet 454, a first transition 456, and a second transition 458. The base sheet 454 may have a curvilinear shape wherein the base sheet defines a first portion 426, a second portion 428, and a third portion 430. In the illustrated embodiment, the first portion 426 has curvilinear side edges and a maximum width that is greater than the maximum width of the second portion 428. Additionally, the third portion 430 has curvilinear side edges and a maximum width that is greater than the maximum width of the second portion 428. The second portion 428 has relatively straight and parallel side edges. The base sheet 454 defines an absorbent facing surface and a chassis facing surface.

In various embodiments, the side containment flaps ideally have a curved cut. For example, the first side containment flap 404 and the second side containment flap 405 of FIG. 32 are illustrated as having a curved cut. While not wishing to be bound by theory, it is believed that the curved cut containment flaps facilitate closer alignment with the natural curvature of the wearer's body. As such, it is believed that a more comfortable and better fit can be achieved to reduce leakage during use.

The first side and second containment flaps 404 and 405 each define a proximal portion 412 and a distal portion 414. A first end 474 of the first containment flap 404 is joined with a first end 474 of the second containment flap 405 to define a first bridging seam 478. Likewise, the second end 476 of the first containment flap 404 and the second end 476 of the second containment flap 405 are joined to define a second bridging seam 186.

Figure 33:
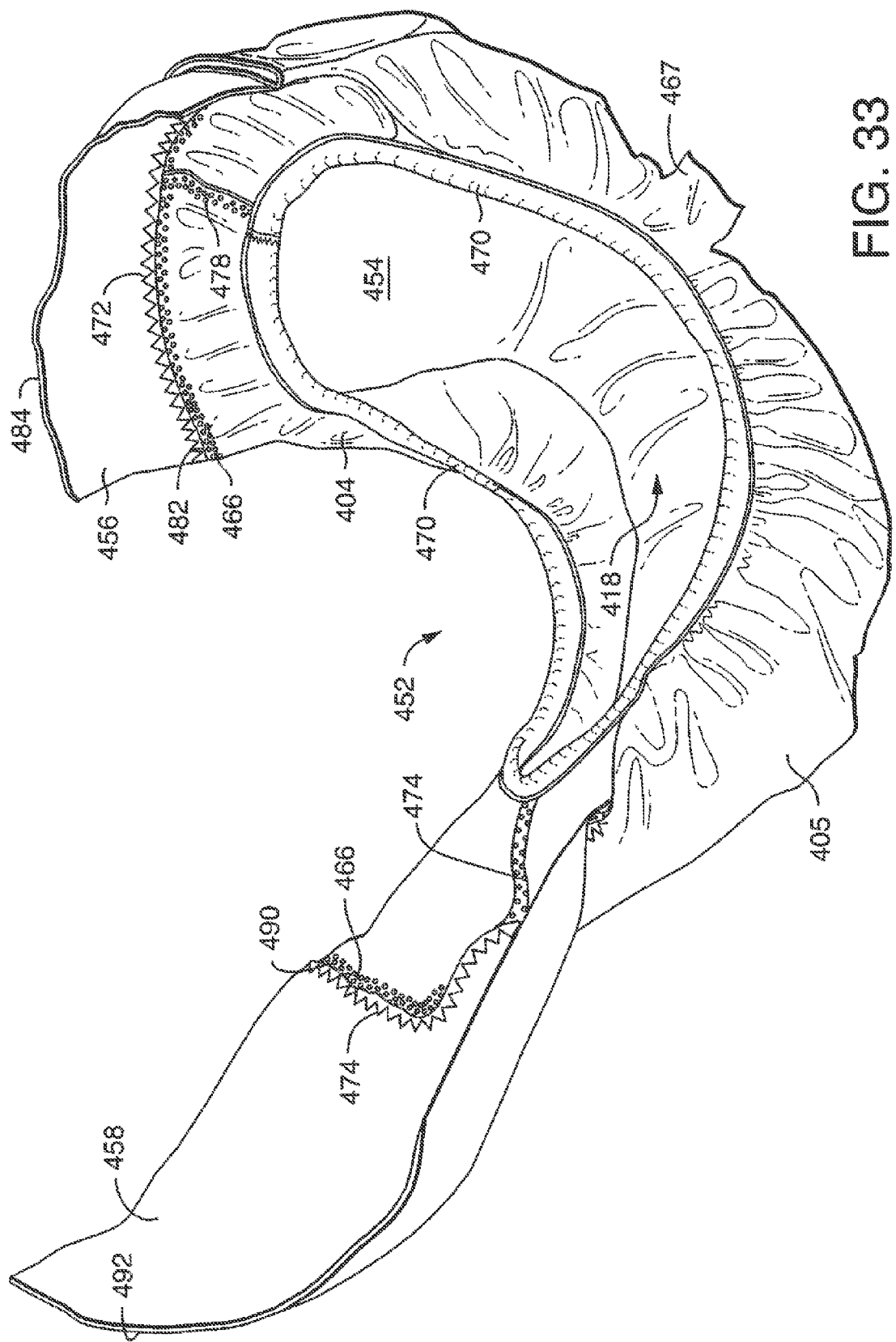
FIG. 33 representatively illustrates a fully constructed sling made from the component parts of FIG. 32.

The proximal portions 412 of each containment flap 404 and 405 is joined with the base sheet 454 to create a containment flap seal 466 and define a fluid-impervious pouch 418 as illustrated in FIG. 33. In some embodiments, the containment flaps may further include one or more elastics. For example, as illustrated in FIG. 14, the distal portion 414 of each of the containment flaps 404 and 405 further includes a containment flap elastic 470.

In various embodiments, the fluid-impervious pouch 418 may be incorporated into any suitable sling and/or chassis using integrated transitions, discrete transitions, or combinations thereof. In various embodiments, the fluid-impervious pouch 418 may be incorporated into any suitable sling and/or chassis using only a transition joined with the front waist region, only a transition joined with the back waist region, or neither. In FIG. 33 the fluid-impervious pouch 418 is joined with the first transition 456 and the second transition 458 to define the sling 452. The first transition 456 defines a first edge 482 and a second edge 484. Likewise, the second transition 458 defines a first edge 490 and a second edge 492. The base sheet 454 defines a first edge 486 and a second edge 488. Desirably, the first edge 486 and the second edge 488 of the base sheet 454 define curved convex shapes. The first edge 486 of the base sheet 454 is joined with the first edge 482 of the first transition 456 to define a first junction 472. The second edge 484 of the first transition 456 defines a curved shape to match the first edge of the base sheet 454. Likewise, the second edge 488 of the base sheet 454 is joined with the first edge 490 of the second transition 458 to define a second junction 474. The first edge 490 of the second transition 458 defines a curved shape to match the second edge 488 of the base sheet 454. The first and second junction 472 and 474 may include adhesive bonding, thermal bonding, ultrasonic bonding, pressure bonding, and the like, and combinations thereof.

In this embodiment, the side containment flaps 404 and 405 both include an integral attachment tab 467. The sling 452 may be joined with a chassis in the crotch region 428 using, in part, the attachment tabs 467.

Figure 34:
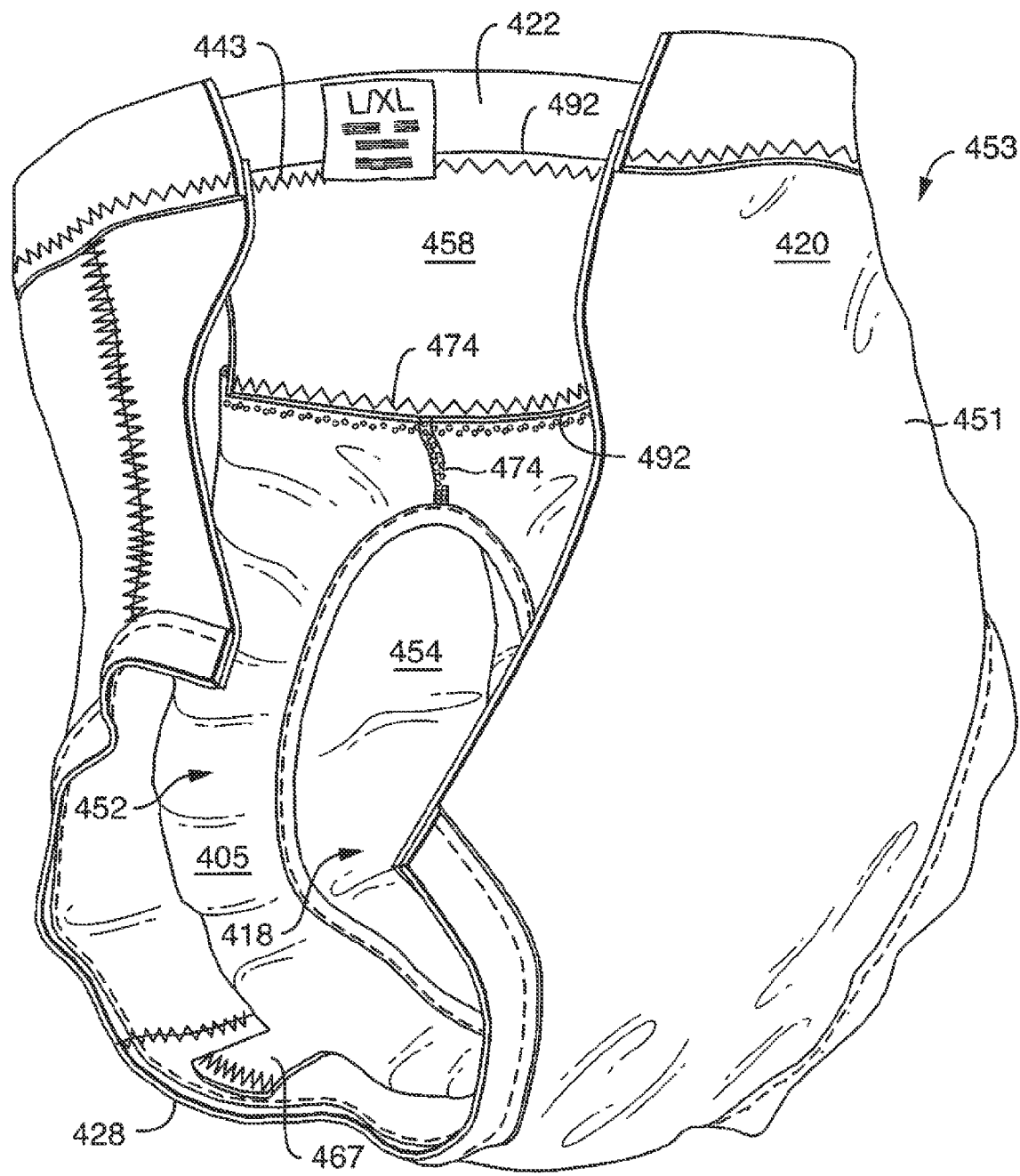
FIGS. 34 and 35 representatively illustrate side perspective views of the fully constructed pouch of FIG. 32 incorporated in a chassis that is partially severed to illustrate internal structure.
Figure 35:
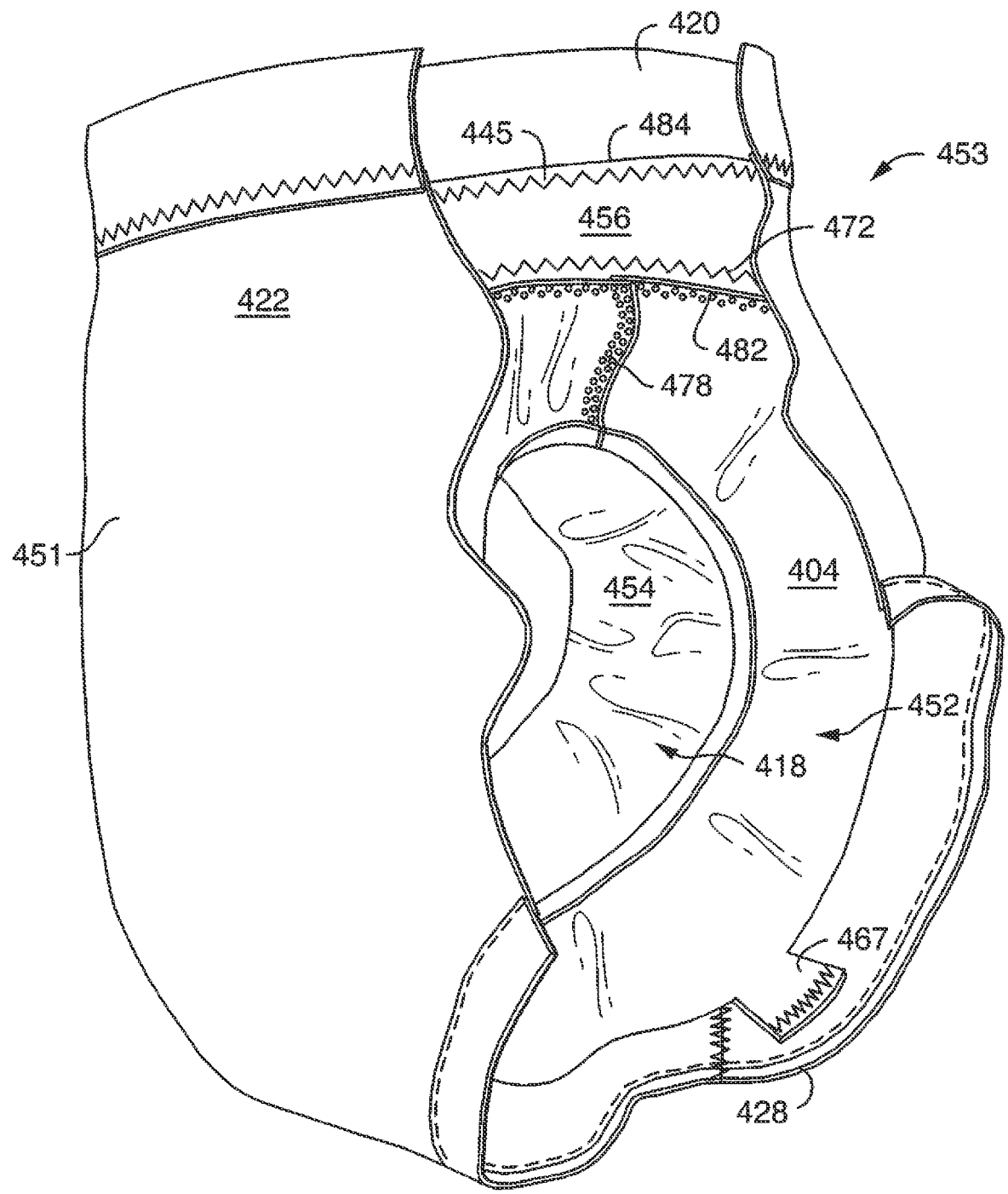

In various embodiments, the sling 452 of FIG. 33 can be joined with any suitable chassis to form a containment pant. In various embodiments, the sling 452 may be joined with a chassis such that the first transition is located in either the front waist region or the back waist region of the chassis and the second transition is located in the opposite region of the chassis. For example, referring now to FIGS. 34 and 35, an exemplary containment pant 453 having a chassis 451 and the sling 452 is representatively illustrated. FIG. 34 is a side perspective view of the containment pant 453 with the chassis 451 partially severed to illustrate the attachment of the sling 452 in the back waist region 422. Specifically, the second transition 458 is joined with the back waist region 422 of the chassis 451 at a back sling seam 443. FIG. 35 is a side perspective view of the containment pant 453 with the chassis 451 partially severed to illustrate the attachment of the sling 452 in the front waist region 420. Specifically, the first transition 456 is joined with the front waist region 420 of the chassis 451 at a front sling seam 445.

In general, any of the containment flaps described herein, may further include one or more containment flap elastics. The containment flap elastics may be joined with the containment flaps in any suitable configuration using any suitable attachment means. For example, in some embodiments, the containment flap elastics may be joined with the containment flaps using mechanical encasement, adhesive bonding, thermal bonding, ultrasonic bonding, pressure bonding, sewing, or the like, or combinations thereof.

In some embodiments, the containment flap elastic may be encased, at least partially, within a channel formed by folding a portion of the containment flap. For example, FIG. 14 representatively illustrates a cross sectional view of the sling 52 of FIG. 13 taken along the line A-A. In this embodiment, the proximal portion 62 of the containment flap 54 is bonded to the base sheet 56 to form containment flap seals 66. The distal portion 64 of the containment flap 54 is folded over upon itself and bonded to itself to form a channel 71. The containment flap elastic 70 is encased within the channel 71 and may be partially attached to the containment flap 54. In other embodiments, the containment flap elastic may be disposed within the channel but not attached to the containment flap.

In some embodiments, the containment flap elastic may be folded over the distal edge of the containment flap. For example, FIG. 20 representatively illustrates a cross sectional view of the sling 102 of FIG. 19 taken along the line B-B. In this embodiment the proximal portion 112 of the containment flaps 104 and 105 are bonded to the base sheet 106 to form containment seals 116. The containment flap elastic 120 is folded over the distal edge 121 of the first side containment flap 104 and the second side containment flap 105. The containment flap elastics 120 may be joined with the side containment flaps 104 and 105 by any suitable method, such as sewing.

In various embodiments, the attachment of the containment flap elastic to the containment flap can be adjusted to vary the tension in the containment flap. For example, in some embodiments, the containment flap elastic may be applied at a uniform tension and select portions can be deadened to provide a containment flap elastic having variable tension along the length of the containment flap. In some embodiments, the containment flap elastic may be applied at variable tension to provide a containment flap elastic having variable tension along the length of the containment flap.

In various embodiments, the containment flaps may be integral with the base sheet. For example, the containment flap 205 illustrated in FIG. 24 is integral with the base sheet 154. In other embodiments, the containment flaps may be discrete pieces of material that are joined with the base sheet using any suitable method to at least partially define the pouch. For example, the containment flap 54 illustrated in FIG. 12 is discrete from and joined with the base sheet 56 at the containment flap seal 66. In some embodiments, one or more containment flaps may be integral with the base sheet and one or more of containment flaps may be discrete pieces. For example, FIG. 18 illustrates the first end containment flap 148 and the second end containment flap 150 being integral with the base sheet 106 while the first side containment flap 104 and second side containment flap 105 are discrete from and joined with the base sheet 106 at the containment flap seals 116.

In various embodiments, the discrete containment flaps may be joined with the base sheet in any suitable manner. For example, the containment flaps may be sewed to the base sheet, heat bonded, adhesively bonded, ultrasonically bonded, seam taped, or the like, or combinations thereof. In embodiments wherein the pouch is fluid-impervious, the discrete containment flaps are joined to the base sheet to provide a fluid-impervious seal. The fluid-impervious seal is believed to prevent leakage from the pouch until the absorbent insert is able to intake the fluid.

In some embodiments, the fluid-impervious seal is created, at least in part, using ultrasonic bonding. Ultrasonic bonding fuses the base sheet material to the containment flap material. The ultrasonic bonding may utilize any suitable bonding pattern to regulate the bond strength of the seal. For example, the ultrasonic bond pattern may be one or more rows of "dash" bonds. For example, in some embodiments, the bond pattern may include three rows of offset dash bonds like illustrated in FIG. 13. In other embodiments, the ultrasonic bond pattern may include one or more continuous "wave" bond patterns. For example, in some embodiments, the bond pattern may include a single continuous wave bond pattern as illustrated in FIG. 18. In other embodiments, the ultrasonic bond pattern may include one or more rows of "dot" bonds. For example, in some embodiments, the bond pattern may include two rows of offset dot bonds as illustrated in FIG. 24. The ultrasonic bonding may be accomplished using a standard ultrasonic horn and anvil. In some embodiments, the ultrasonic bonds may be created using a sonic sewing machine. A suitable machine is available from Sonobond and has model number LM920.

The use of ultrasonic bonding is believed to be beneficial in some embodiments over sewing because no holes are created in the containment flap and thus the integrity of the pouch is preserved. Likewise, the use of ultrasonic bonding is believed to be beneficial in some embodiments over seam tape because the base sheet and/or containment flaps could melt at the application temperature of typical seam tape. In some embodiments, the base sheet is made of a polyurethane and polyester laminate and the containment flaps are made of a polyurethane and polyester laminate. In these embodiments, the base sheet and the containment flap can be constructed with ultrasonic bonding to create a strong seal without burning through either the base sheet or the containment flap.

The flap seals collectively define a flap seal perimeter. The portion of the base sheet circumscribed by the flap seal perimeter constitutes the pouch floor. For example, referring now to FIG. 29, the containment flaps 330, 332, 334, and 336 are joined to the base sheet 338 at the flap seals 344 and define a flap seal perimeter 356. The location on the base sheet 338 where the flap seal perimeter 356 will be formed is shown with a dashed line on FIG. 28 for purposes of illustration. In general, the portion of the base sheet 338 circumscribed by the flap seal perimeter 356 constitutes the pouch floor 358. The pouch floor 358 defines a pouch floor length 360, a pouch floor width 362, and a pouch floor area 364.

In any of the embodiments disclosed herein, one or more of the containment flaps may further include an absorbent insert stop. The absorbent insert stop may be any suitable physical barrier that limits the depth of insertion of the absorbent insert into one or more of the containment flaps. In various embodiments the absorbent insert stop may be a mechanical bond between the containment flap and the base sheet. The mechanical bond may be an ultrasonic bond, a thermal bond, a stitched bond, a pressure bond, an adhesive bond, or the like, or a combination thereof. For example, referring now to FIG. 29, the second end containment flap 336 is illustrated with an absorbent insert stop 351. In this embodiment, the absorbent insert stop 351 is illustrated as an ultrasonic bond that limits the depth of insertion of the absorbent insert into the second end containment flap 336. In another example, the second end containment flap 150 of FIG. 18 is illustrated with an insert stop 147 that is an ultrasonic bond between the second end containment flap 150 and the base sheet 106.

In embodiments having one or more absorbent insert stops, the pouch floor length and the pouch floor area are defined in part by the containment flap seal and in part by the absorbent insert stop. For example, referring again to FIG. 28, the location on the base sheet 338 where the absorbent insert stop 351 will be formed is shown with a dashed line for purposes of illustration. In embodiments with the absorbent insert stop 351, the pouch floor 358 defines a pouch floor length 361 and a pouch floor area 365. In these embodiments, the pouch floor length 361 is defined by the end portion 355 of the containment flap seal 344 and the absorbent insert stop 351. Likewise, the pouch floor area 365 is defined by the absorbent insert stop 351 and the side portions 357 of the containment flap seal 344 up to the points where the absorbent insert stop 351, if extended, would intersect the containment flap seal 344.

In embodiments that include one or more absorbent insert stops, the pouch floor may also define a reservoir portion that extends between the absorbent insert stop and the containment flap seal under a containment flap. For example, referring again to FIGS. 28 and 29, the pouch floor 358 defines a reservoir portion 359 that extends from the absorbent insert stop 351 to the end portion 363 of the containment flap seal 344. In another example, referring now to FIG. 18, the pouch 118 includes a reservoir portion 145 that extends from the absorbent insert stop 147 to the end flap seal 117. As discussed previously, the insert stops may be any suitable length or width and may be positioned at any suitable depth within the first end containment pocket and/or the second end containment pocket. In some embodiments, the absorbent insert stops may terminate short of one or both containment flap seals and thereby allow fluid within the containment pocket to flow around the absorbent insert stop and into the reservoir portion. In various embodiments, the reservoir portion may have a length of about 50 to 70 mm or about 60 mm.

The pouch floor 358 also defines a first end section 366, a second end section 367, and a central section 368 in the longitudinal direction 48. The central section 368 extends between the first end section 366 and the second end section 367. The first end section 366 defines a first end section width 369 and a first end section length 370. The second end section 367 defines a second end section width 371 and a second end section length 372. The central section 368 defines a central section width 373 and a central section length 374. The first end section length 370 plus the second end section length 372 plus the central section length 374 equals the pouch floor length. The widths of the various sections are measured in the transverse direction 50 and the lengths of the various sections are measured in the longitudinal direction 48. The pouch floor dimensions are measured on an assembled pouch by tracing around the inner edge of the flap seal perimeter with a pen, cutting the containment flaps and elastic from the pouch, and laying the pouch floor flat. If no flap seal is present, the pouch floor is defined relative to the distal edge of the containment flap. Specifically, in these embodiments, the pouch floor is defined by the position 30 mm from the distal edge of the containment flap.

In an embodiment adapted for children weighing 60 to 120 pounds, which may be characterized as size large and/or extra large, the pouch floor length may be 380 to 500 mm, or 410 to 470 mm, or about 440 mm. In an embodiment adapted for children weighing 38 to 65 pounds, which may be characterized as small and/or medium, the pouch floor length may be 350 to 450 mm, 375 to 425 mm, or about 400 mm. In some of these embodiments, the pouch floor may also include a reservoir having a length of 50 to 70 mm or about 60 mm.

In various embodiments, the first end section length may equal the central section length which may equal the second end section length. In other embodiments, the first end section length may equal the second end section length and the central section length may be different. For example, the first end section length may be about 35% the pouch floor length, the second end section length may be about 35% the pouch floor length, and the central section length may be about 30% the pouch floor length. In another example, the first end section length may be about 30% the pouch floor length, the second end section length may be about 30% the pouch floor length, and the central section length may be about 40% the pouch floor length.

In various embodiments, the pouch floor may have a width that varies at different points along the longitudinal direction. For example, as illustrated in FIG. 28, the pouch floor 358 has a variable width at different points along the longitudinal direction. In this embodiment, the first end section 366 and the second end section 368 have a maximum width that is greater than the maximum width of the central section 367. For example, the first end section and the second end section may have a maximum width of about 145 to 195 mm, about 160 to 180 mm or about 171 mm. In these embodiments, the central section may have a maximum width of about 60 to 100, about 70 to 90 mm, or about 82 mm.

In various embodiments, the first end section, the second end section, and/or the central section may have a variable width at different points along the longitudinal direction or may have a consistent width at different points along the longitudinal direction. In some embodiments, the first end section and the second end section may have variable width at different points along the longitudinal direction and the central section may have a consistent width at different points along the longitudinal direction as illustrated in FIG. 28. In some embodiments, the first end section and the second end section may have a width that varies from 171 mm at the maximum to 82 mm at the minimum. In these embodiments, the central section may have a consistent width of about 82 mm.

In some embodiments, the pouch floor defines a first reference width 376 measured at ⅛ the pouch floor length, a second reference width 377 measured at ½ the pouch floor length, and a third reference width 378 measured at ⅞ the pouch floor length. In some embodiments, the first reference width 376 may be equal to the third reference width 378 and the second reference width 377 may be less than the first and third reference widths 376 and 378. In some embodiments, the second reference width 377 may be less than 50%, 60%, 70%, or 80% the first reference width 376 and/or the third reference width 378. In some embodiments, the second reference width 377 may be about 48% the first reference width 376 and the third reference width 378.

In various embodiments, the pouch floor area may be any suitable value. For example, in embodiments adapted for children weighing 60 to 120 pounds, the pouch floor area may be about 55,000 $mm^2$. In embodiments adapted for children weighing 38 to 65 pounds, the pouch floor area may be about 47,700 $mm^2$.

In various embodiments, the pouch floor may define any suitable shape. For example, the pouch floor may have a symmetric shape about the transverse centerline or may have an asymmetric shape about the transverse centerline. In various embodiments, the pouch floor may have a dog-bone-shape, hourglass-shape, T-shape, rectangular shape, or the like.

In various embodiments, the pouches of the present invention may be joined with one or more transitions in any suitable manner. For example, the pouches may be joined with the transitions by sewing, ultrasonic bonding, thermal bonding, adhesive bonding, seam taping, and the like, and combinations thereof. In some embodiments, the transitions may be joined with the pouches by sewing, using any suitable stitch or combination of stitches. For example, in some embodiments, the transitions may be attached to the pouches using a single needle stitch followed by a top stitch.

In some embodiments, the pouches may be constructed such that extra material is available for attaching the transitions without breaching the fluid-impervious integrity of the pouch. For example, in some embodiments, the containment flap may be joined to the base sheet at the containment flap seal. The containment flap seal may be positioned such that a portion of the containment flap material and/or the base sheet material is available for attaching to the first and/or second transition while maintaining the integrity of the fluid-impervious pouch.

In some embodiments, the sling is minimally attached to the chassis to maximize the fit and natural movement of the chassis. In some embodiments, the sling is attached to the chassis via the first transition and/or the second transition. In various embodiments, the first transition may be joined with front waist region at the front sling seam and the second transition may be joined with the back waist region at the back sling seam. In other embodiments, the first transition may be joined with the back waist region at the back sling seam and the second transition may be joined with the front waist region at the front sling seam. The first transition and/or the second transition may be joined to any suitable portion of the front waist region and/or the back waist region. For example, the first transition and/or the second transition may be joined at the waist elastic seam in the front waist region and/or the back waist region. Additionally or alternatively, the first transition and/or the second transition may be joined to the outer shell in the front waist region and/or the second waist region. In some embodiments, the first transition and/or the second transition may be integral with the chassis. In these embodiments, the integral transition is joined with the pouch using any suitable method, including those described herein. In some embodiments, the first transition and/or the second transition may be integral with the shell of the chassis. For example, FIGS. 8 and 10 representatively illustrate a transition that is integral with the shell of the chassis. In these embodiments, the integral transition is part of the shell material and is a distinct projection of the shell material.

In some of the embodiments, the sling may be attached to the chassis in the front waist region, the back waist region, and the crotch region. The sling may be attached to the chassis in the crotch region by any suitable means. For example, the sling may be sewed, ultrasonic bonded, thermal bonded, adhesive bonded, pressure bonded, and the like, and combinations thereof. In some embodiments, the sling may be attached to the chassis in the crotch region via one or more tabs. The tabs may be discrete pieces of material that are joined with both the pouch of the sling and with the chassis using any suitable means. For example, in some embodiments, the tabs may be discrete pieces of material that are ultrasonically bonded to the pouch of the sling and sewn with thread to the chassis. In various embodiments, the tabs may be attached to the chassis using any suitable sewing stitch or combinations thereof. For example, in some embodiments, the tabs may be attached to the chassis using a zig zag stitch. Alternatively, the tab may be an integral part and distinct projection of the chassis and may be sewed to the pouch.

Referring now to FIGS. 26 and 27, the sling 152 is joined with the crotch region 28 of the chassis 151 via discrete tabs 100 (only one visible). Specifically, the tabs 100 are joined with the sling 152 via a first tab seam 149. Likewise, the tabs 100 are joined with the chassis 151 via a second tab seam 199. The first tab seam 149 is an ultrasonic bond to preserve the fluid-impervious pouch 206. The second tab seam 199 is a thread sewn bond.

In some embodiments, the tabs may be an integral part of the sling. For example, the tabs may be an integral part of one or more of the containment flaps. In these embodiments, the sling may be joined to the chassis by joining the tabs with the chassis using any suitable means. For example, in FIGS. 11-16, the containment flap 54 includes attachment tabs 67 extending from the proximal portion 62 of the containment flap 54. As illustrated in FIGS. 15 and 16, the sling 52 is joined with the crotch region 28 of the chassis 51 by the attachment tabs 67 (only one visible) and tab seams 199 (only one visible).

In another example, the tab may be an integral part of the base material. In these embodiments, the sling may be joined to the chassis by joining the tabs with the chassis using any suitable means. In other embodiments, the tabs may be an integral part of both the base material and the containment flaps. For example, in FIGS. 17-22, the side containment flaps 104 and 105 both include an integral attachment tab 94. Likewise, the base sheet 106 includes a pair of integral attachment tabs 96. The sling 102 may be joined with a chassis using, in part, the attachment tabs 94 and/or 96. For example, FIGS. 21 and 22 representatively illustrate the sling 102 joined with the chassis 101 at the crotch region 28 utilizing the attachment tabs 94 and 96.

In some embodiments, the slings of the present invention define a perimeter and are joined to the chassis about the perimeter. For example, referring again to FIG. 19, the sling 102 defines a perimeter 115 that includes portions of the first transition 108, the second transition 110, and the pouch 118. In various embodiments, the slings of the present invention may be joined to the chassis about any suitable percentage of the perimeter. For example, in some embodiments, the sling may be joined to the chassis at less than 30%, less than 25%, less than 20%, and less than 15% of the perimeter. In some embodiments, the sling may be attached to the chassis at about 22% of the perimeter. In some embodiments, the attachment tabs have a length in the longitudinal direction that is less than 75 mm, less than 50 mm, or less than 25 mm.

The outer shell may be made of any suitable material or combination of materials. In various embodiments, the outer shells of the present invention may be made of cotton, cotton blends, nylon, nylon blends, polyester, polyester blends, rayon, rayon blends, spandex, and the like and combinations thereof. In some embodiments, the outer shells may be a blend of nylon and spandex. For example, the outer shells may be 80% nylon and 20% spandex material. In some embodiments, the outer shell may be a cotton fabric blended with spandex. For example, the outer shell may be cotton fabric having 2% to 25%, 15% to 22%, or about 20% spandex. Thus, in some embodiments, the shell may be 80% cotton and 20% spandex. In other embodiments, the outer shell may be a polyester fabric blended with spandex. In these embodiments, the polyester fabric may have 2% to 16%, 10% to 15%, or about 14% spandex. Thus, in some embodiments, the shell may be 86% polyester and 14% spandex.

The chassis material is adapted to have an elongation and peak load in both the transverse and longitudinal direction to hold the pant securely against the body both at initial donning and after insult. The elongation and peak load of various materials can be determined by using the Strip Tensile Test described below. This test measures the load in grams and elongation in percent. In this test, two clamps, each having two jaws with each jaw having a facing in contact with the sample, hold the material in the same plane, usually vertically, separated by 3 inches and move apart at a specified rate of extension. Values for this test are obtained using a suitable sample width, a 7-inch sample length, a jaw facing size of 1 inch high by 3 inches wide, and a constant rate of extension of 300 mm/minute. The Sintech 2 tester, available from the Sintech Corporation, 1001 Sheldon Dr., Cary, N.C. 27513, is suitable for use with this test. The Instron Model™, available from the Instron Corporation, 2500 Washington St., Canton, Mass. 02021, or a Thwing-Albert Model INTELLECT II, available from the Thwing-Albert Instrument Co., 10960 Dutton Rd., Philadelphia, Pa. 19154, may also be used for this test.

An exemplary chassis material and pouch base sheet material was tested using this test method. To measure the transverse direction profile, the samples were cut to 3 inches in the longitudinal direction and 7 inches in the transverse direction. To measure the longitudinal direction profile, the samples were cut to 3 inches in the transverse direction and 7 inches in the longitudinal direction.

In some embodiments, the chassis material desirably has an elongation in both the transverse direction and the longitudinal direction from about 125% elongation at 2000 grams force to about 175% elongation at 2000 grams force. In addition, the peak load (per 3 inch width) in the transverse direction and in the longitudinal direction is between about 10,000 grams force and about 30,000 grams force. Table 1 illustrates the elongation and peak load values for a preferred chassis material.

TABLE 1

Chassis Material Elongation and Peak Load

| transverse elongation at 2000 gF | longitudinal elongation at 2000 gF | transverse peak load (gF) | longitudinal peak load (gF) |
|---|---|---|---|
| 139% | 145% | 20,009 | 20,018 |

In some embodiments, the pouch base sheet material desirably has an elongation in both the transverse direction and the longitudinal direction from about 10% elongation at 2000 grams force to about 40% elongation at 1400 grams force. In addition, the peak load (per 3 inch width) in the transverse direction and in the longitudinal direction is between about 10,000 grams force and about 30,000 grams force. Table 2 illustrates the elongation and peak load values for a preferred pouch base sheet material.

TABLE 2

Pouch Base Sheet Material Elongation and Peak Load

| transverse elongation at 1400 gF | longitudinal elongation at 1400 gF | transverse peak load (gF) | longitudinal peak load (gF) |
|---|---|---|---|
| 13% | 25% | 20,016 | 20,085 |

Products having the above ranges of elongation and peak load in the chassis and pouch base sheet materials have been found to provide the optimal fit for a user to securely fit the containment pant and prevent leakage after an insult.

In addition, to function properly for a wearer of the product, the chassis and sling materials should have proper breathability. Breathable chassis materials permit escape of water vapor from the absorbent garment, increasing the garment comfort and reducing skin rashes and other irritations that result when water vapor is trapped inside the garment and heated by the wearer's body. The chassis materials for use in the containment pant are highly breathable, for maximum wearer comfort.

Breathability of the chassis materials and pouch materials may be tested using the water vapor transmission rate described below. Desirably, the chassis materials for use in the containment pant herein have a breathability of between about 10,000 and about 35,000 grams/(m$^2$-24 hours). One exemplary material has a breathability of about 16,000 grams/(m$^2$-24 hours).

Desirably, the base sheet materials for use in the sling of the containment pant herein have a breathability of between about 500 and about 2500 grams/(m$^2$-24 hours). One exemplary material has a breathability of about 1230 grams/(m$^2$-24 hours).

The following procedure is described for testing of the water vapor transmission rate (WVTR) for breathable films and laminates. The WVTR is measured in a manner similar to ASTM Standard Test Method for Water Vapor Transmission of Materials, Designation E-96-80 as follows. For the purposes of the present invention, 3 inch diameter (76 mm) circular samples are cut from the test material and from a control material, CELGUARD®2500 (Hoechst Celanese Corporation). CELGUARD®2500 is a 0.0025 cm thick film composed of microporous polypropylene. Two or three samples are prepared for each material.

The cups used for testing are cast aluminum, flanged, 2 inches deep and come with a mechanical seal and neoprene gasket. The cups are distributed by Thwing-Albert Instrument Company, Philadelphia, Pa., under the designation Vapometer cup #681. One hundred millimeters of distilled water is poured into each Vapometer cup, and each of the individual samples of the test materials and control material are placed across the top area of an individual cup. Screw-on flanges are tightened to form a seal along the edges of the cups leaving the associated test material or control material exposed to the ambient atmosphere over a 62 millimeter diameter circular area (an open, exposed area of about 30 cm$^2$). The cups are then weighed, placed on a tray, and set in a forced air oven set at 100° F. (38° C.).

The oven is a constant temperature oven with external air through it to prevent water vapor accumulation inside. A suitable forced air oven is, for example, a Blue M Power-O-Matic 60 oven distributed by Blue M Electric Co. of Blue Island, Ill. After 24 hours, the cups are removed from the oven and weighed. The preliminary test WVTR value is calculated as follows:

Test WVTR=[(grams weight loss over 24 hours)×7571]÷24

The relative humidity within the oven is not specifically controlled. Under predetermined set conditions of 100° F. and ambient relative humidity, the WVTR for CELGUARD®2500 has been determined to be 5000 g/m$^2$*24 hours. Accordingly, CELGUARD®2500 is run as a control sample with each test and the resulting values are corrected in accord with the variation of the control relative to its known WVTR.

The waist elastic and/or leg elastic may be made of any suitable material or combination of materials. In some embodiments, the waist elastic and/or leg elastic may be made of nylon, spandex, polyester, cotton, rayon, and the like, and combinations thereof. In some embodiments, the waist elastic and/or leg elastic may be a blend of nylon, spandex, and polyester. For example, in some embodiments, the waist elastic and/or the leg elastic may be 46% nylon, 28% spandex, and 26% polyester. In various embodiments, any suitable thread may be used to secure the waist elastic to the shell material. For example, in some embodiments, the thread used to secure the waist elastic and/or leg elastic to the shell may be polyester thread.

The transition materials may be made of any suitable material or combination of materials. In various embodiments, the transition materials of the present invention may be made of cotton, cotton blends, nylon, nylon blends, polyester, polyester blends, rayon, rayon blends, spandex, and the like and combinations thereof. In some embodiments, the transition materials may be a blend of nylon and spandex. For example, the transition materials may be 80% nylon and 20% spandex material. In some embodiments, the transition materials may be a cotton fabric blended with spandex. For example, the transition materials may be cotton fabric having 12% to 25%, 15% to 22%, or about 20% spandex. Thus, in some embodiments, the transition materials may be 80% cotton and 20% spandex. In other embodiments, the transition materials may be a polyester fabric blended with spandex. In these embodiments, the polyester fabric may have 8% to 16%, 10% to 15%, or about 14% spandex. Thus, in some embodiments, the transition materials may be 86% polyester and 14% spandex.

In some embodiments, the first transition is made of a first material and the second transition is made of the same first material. In other embodiments, the first transition is made of a first material and the second transition is made of a second material that is different than the first material. In various embodiments, the first transition and/or the second transition may be elastically extensible in one or more directions. For example, in some embodiments, both the first transition and the second transition are elastically extensible in the longitudinal direction and the transverse direction. In some embodiments, the first material and second material are made from the same material as the chassis material. In other embodiments, the first material and second material are made from the same material as the pouch base sheet material.

In some embodiments, the first transition defines a first transition width as measured in the transverse direction and a first transition length as measured in the longitudinal direction. Likewise, the second transition defines a second transition width as measured in the transverse direction and a second transition length as measured in the longitudinal direction. For example, referring again to FIG. 17, the first transition 108 defines a first transition width 109 and a first transition length 107. Likewise, the second transition 110 defines a second transition width 111 and a second transition length 113. In various embodiments, the first transition width may be the same as the second transition width. In other embodiments, the first transition width may be less than the second transition width. In other embodiments, the first transition width may be greater than the second transition width. In some embodiments, the first transition width may be 100 to 125 mm and the second transition width may be 170 to 200 mm. In some embodiments, the first transition width may be about 114 mm and the second transition width may be about 185 mm.

In various embodiments, the slings of the present invention may include only a first transition or only a second transition. In various embodiments, the slings of the present invention may include both a first transition and a second transition. The first transition or second transition may be positioned in the front waist region or the back waist region in any of the embodiments described herein.

In some embodiments, the base sheet may be made of any suitable material or combination of materials. In some embodiments, the base sheet may be made of polyester, polyurethane, polypropylene, polyethylene, or the like, or combinations thereof. In some embodiments, the base sheet may be a woven polyester fabric laminated with polyurethane. In some embodiments, the base sheet may be 55% polyester and 45% polyurethane by weight. In some embodiments, the base sheet may be a woven polyester fabric laminated with a polyurethane layer. In various embodiments, the polyurethane layer may have any suitable thickness. For example, the polyurethane layer may have a 1 mm thickness. In various embodiments, the woven polyester fabric may be laminated with a polyurethane layer using any suitable joining means. For example, the polyurethane layer and the polyester fabric may be laminated together using adhesive, thermal bonding, mechanical bonding, and the like, and combinations thereof. In some embodiments, the base sheet may be a woven polyester fabric adhesively laminated to a polyurethane layer having a thickness of 1 mm.

In various embodiments, the base sheet may be elastically extensible in one or more directions. For example, in some embodiments, the base sheet may be elastically extensible in the longitudinal direction and/or the transverse direction. In other embodiments, the base sheet may be non-extensible in one or more directions.

In various embodiments, the base sheet may have any suitable shape. In some embodiments the base sheet may be rectangular or non-rectangular. For example, as illustrated in FIG. 11, the base sheet 56 may have a curvilinear shape wherein the base sheet defines a first portion 76, a second portion 78, and a third portion 80. In the illustrated embodiment, the first portion 76 has curvilinear side edges and a maximum width that is greater than the maximum width of the second portion 78. Additionally, the third portion 80 has curvilinear side edges and a maximum width that is greater than the maximum width of the second portion 78. The second portion 78 has relatively straight and parallel side edges.

In another example, illustrated in FIG. 17, the base sheet 106 may have a curvilinear shape wherein the base sheet defines a first portion 126, a second portion 128, and a third portion 130. In the illustrated embodiment, the first portion 126 has curvilinear side edges and a maximum width that is greater than the maximum width of the second portion 128. Additionally, the third portion 130 has curvilinear side edges and a maximum width that is greater than the maximum width of the second portion 128. The second portion 128 has relatively straight and parallel side edges except for the tab 96 which is a distinct projection of the base sheet 106.

In another example, illustrated in FIG. 23, the base sheet 154 may have a curvilinear shape wherein the base sheet defines a first portion 190, a second portion 191, and a third portion 198. In the illustrated embodiment, the first portion 190 has curvilinear side edges and a maximum width that is greater than the maximum width of the second portion 191. Additionally, the third portion 198 has curvilinear side edges and a maximum width that is greater than the maximum width of the second portion 191. The second portion 191 has relatively straight and parallel side edges.

In another example, illustrated in FIG. 28, the base sheet 338 may have a curvilinear shape wherein the base sheet defines a first portion 366, a second portion 367, and a third portion 368. In the illustrated embodiment, the first portion 366 has curvilinear side edges and a maximum width that is greater than the maximum width of the second portion 367. Additionally, the third portion 368 has curvilinear side edges and a maximum width that is greater than the maximum width of the second portion 367. The second portion 367 has relatively straight and parallel side edges.

In some embodiments, the containment flap material may be made of any suitable material or combination of materials. In some embodiments, the containment flap material may be made of polyester, polyurethane, polypropylene, polyethylene, or the like, or combinations thereof. In some embodiments, the containment flap material may be a woven polyester fabric laminated with polyurethane. In some embodiments, the containment flap material may be 55% polyester and 45% polyurethane by weight. In some embodiments, the containment flap material may be a woven polyester fabric laminated with a polyurethane layer. In various embodiments, the polyurethane layer may have any suitable thickness. For example, the polyurethane layer may have a 1 mm thickness. In various embodiments, the woven polyester fabric may be laminated with a polyurethane layer using any suitable joining means. For example, the polyurethane layer and the polyester fabric may be laminated together using adhesive, thermal bonding, mechanical bonding, and the like, and combinations thereof. In some embodiments, the containment flap material may be a woven polyester fabric adhesively laminated to a polyurethane layer having a thickness of 1 mm.

In various embodiments, the containment flap material may be elastically extensible in one or more directions. For example, in some embodiments, the containment flap material may be elastically extensible in the longitudinal direction and/or the transverse direction. In other embodiments, the containment flap material may be non-extensible in one or more directions.

The flap elastic can be formed of any suitable elastic material. As is well known to those skilled in the art, suitable elastic materials include sheets, strands or ribbons of natural rubber, synthetic rubber, or thermoplastic elastomeric polymers. The flap elastic can be stretched and adhered to the containment flap, adhered to a gathered containment flap, or adhered to a containment flap and then elasticized or shrunk such that elastic retractive forces are imparted to the containment flap. In some embodiments, the flap elastic may be made of nylon, spandex, polyester, cotton, rayon, and the like, and combinations thereof. In some embodiments, the flap elastic may be a blend of nylon and spandex. For example, in some embodiments, the flap elastic may be 91% nylon and 9% spandex.

In some embodiments, the flap elastic may be a low tension fold-over-elastic. This type of flap elastic is believed to reduce the amount of gathers and potential irritation points in the containment flaps. Additionally, this type of flap elastic has a flatter profile and is believed to be more comfortable and provide more surface contact with the wearer's skin for a better gasket against the body.

In some embodiments, the flap elastic may be joined with the containment flap to define a finished flap tension. In various embodiments, the finished flap tension may be generally uniform along the entire length of the containment flap. In other embodiments, the finished flap tension may be variable along the length of the containment flap. For example, in some embodiments, the finished flap tension may be higher near the crotch region of the containment pant and may be lower near the front waist region and/or the back waist region.

Referring again to FIG. 28, the first side containment flap 330 and the second side containment flap 332 define a distal edge 343 and a distal edge length 347. In various embodiments, the containment flap elastic 345 (not illustrated in FIG. 28) may be applied at variable tension along the length 347 of the flaps 330 and 332. In some embodiments, the containment flap elastic 345 may be applied to define a first tension zone 380, a second tension zone 381, and a third tension zone 382. In various embodiments, the elastic tension in the second tension zone 381 may be greater than the elastic tension in the first tension zone 380 and may be greater than the elastic tension in the third tension zone 382. In some embodiments, the elastic tension in the first tension zone 380 may be the same as the elastic tension in the third tension zone 382.

For example, in one embodiment, the containment flap relaxed length 347 may be 390 mm and the containment flap elastic 345 may have a relaxed length of 260 mm. The flap elastic 345 may be applied relaxed (i.e., no elongation) along the first 38 mm of the distal edge 343 to define the first tension zone 380. The elastic 345 may be applied at an elongation of 89% along the next 276 mm of the distal edge 343 to define the second tension zone 381. In other words, 146 mm of relaxed elastic 345 is stretched to 276 mm and then applied to the distal edge 343 in the second tension zone 381. Finally, the elastic 345 may be applied relaxed along the final 76 mm of the distal edge 343 to define the third tension zone 382.

In another embodiment, the containment flap relaxed length 347 may be 414 mm and the containment flap elastic 345 may have a relaxed length of 273 mm. The flap elastic 345 may be applied relaxed (i.e., no elongation) along the first 38 mm of the distal edge 343 to define the first tension zone 380. The elastic 345 may be applied at an elongation of 85% along the next 300 mm of the distal edge 343 to define the second tension zone 381. In other words, 162 mm of relaxed elastic 345 is stretched to 300 mm and then applied to the distal edge 343 in the second tension zone 381. Finally, the elastic 345 may be applied relaxed along the final 76 mm of the distal edge 343 to define the third tension zone 382.

In various embodiments, the containment flap elastic 345 may be applied in the second tension zone 381 at 0 to 200% elongation, 50 to 150% elongation, or about 70 to 90% elongation. In various embodiments, the containment flap elastic 345 may be applied in the first tension zone 380 and/or the third tension zone 382 at 0 to 150% elongation.

In various embodiments, at least one of the materials of the containment pant is treated to be more fluid impervious. For example, in any of the embodiments described herein, at least one of the shell, waist elastic, leg elastic, transitions, base sheet, containment flaps, containment flap elastic, and thread are treated to be more fluid impervious. In various embodiments, the treatment may include coating the materials in any suitable manner using a durable water resistant treatment. In some embodiments, the durable water resistant treatment may include a polymer coating. In some embodiments, the base sheet and/or the containment flaps may include a fabric laminated with polyurethane wherein the fabric side of the base sheet is treated with a durable water resistant treatment. In some embodiments, the base sheet and the containment flaps may be made from a woven polyester fabric treated with a durable water resistant treatment and laminated with a polyurethane sheet. In some embodiments, the thread used to join the containment flap elastic to the containment flaps may be treated with a durable water resistant treatment.

In some embodiments, the containment pants of the present invention may be adapted to fit a wide range of sizes. In some embodiments, an exemplary containment pant may be adapted to fit children weighing between 38 and 65 pounds. In some embodiments, an exemplary containment pant may be adapted to fit children weighing between 60 and 120 pounds. To facilitate such a wide range of weight and maintain proper fit, the containment pants of the present invention may be adapted in the waist, hip, and/or legs to extend up to about 100% while still providing sufficient retractive force to hold the pants securely against the body at donning, during use, and after insult.

The various containment pants of the present invention are adapted to receive and support a discrete absorbent insert. As used herein, the term "discrete absorbent insert" refers to a self-contained absorbent structure that is adapted for insertion and removal from a pant without tearing, breaking, or otherwise damaging the self-contained absorbent structure or the pant. In some embodiments, the absorbent insert has a relatively high capacity adapted for enuretic children and/or for use overnight. In various embodiments, the pants of the present invention may be devoid of an integrated absorbent core. As used herein, the term "integrated absorbent core" refers to a mass of fibers, particulate, foam, or the like, or combinations thereof having an absorbent capacity of at least 5 g/g and being contained within a pant and not being adapted for removal from the pant without tearing, breaking, or otherwise damaging the pant and/or the absorbent core. Suitable absorbent inserts are also described in patent application U.S. Ser. No. 13/548,000, entitled "Absorbent Insert", filed on Jul.

12, 2012, and having attorney docket number 64816460US 02, the entirety of which is incorporated herein by reference.

Figure 36:
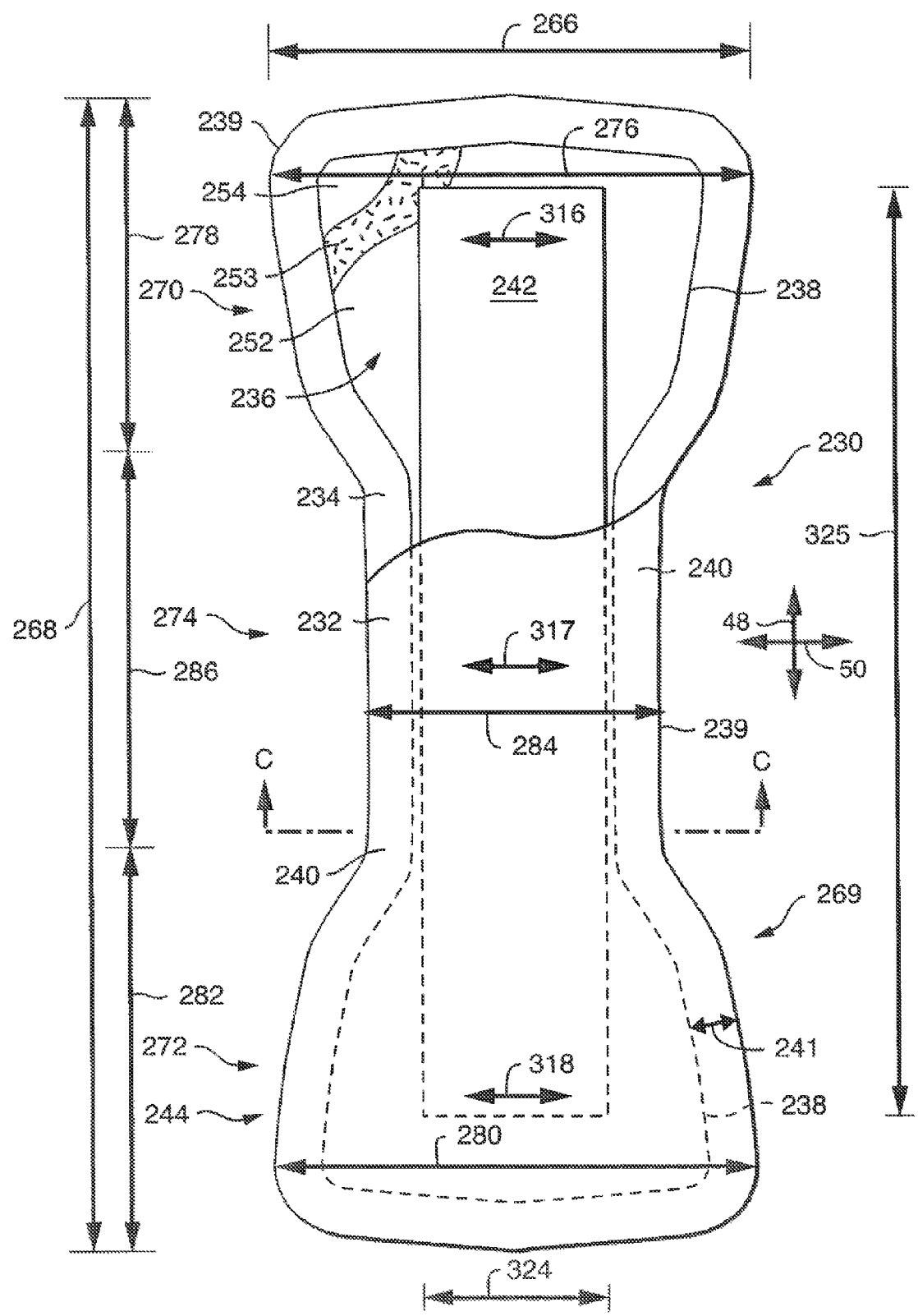
FIG. 36 representatively illustrates a top plan view of an exemplary absorbent insert of the present invention with portions cut away to illustrate underlying structure.
Figure 37:
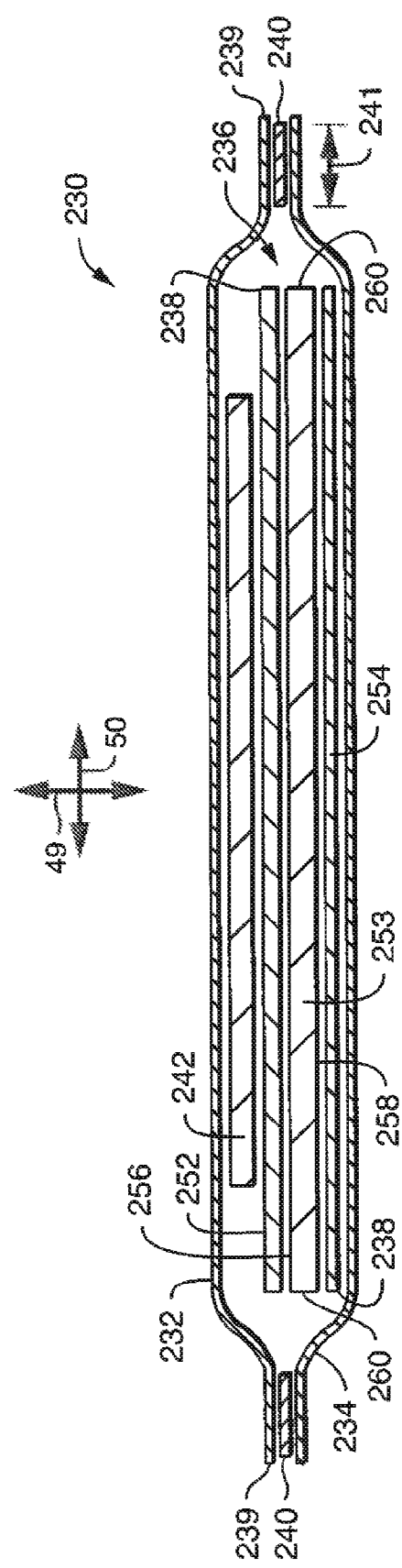
FIG. 37 representatively illustrates a cross sectional view of the absorbent insert of FIG. 36 taken along the line C-C.

Referring now to FIGS. 36 and 37, a first exemplary absorbent insert 230 is representatively illustrated. FIG. 36 is a top plan view of the absorbent insert 230 with portions cut away to better illustrate underlying structure. FIG. 37 is an expanded cross-sectional view of the absorbent insert of FIG. 36 taken along the line C-C. The absorbent insert 230 defines a longitudinal-direction 48, a relatively shorter, transverse direction 50, and a thickness direction 49. The transverse direction extends generally perpendicular to the longitudinal direction, and the thickness or z-direction extends generally perpendicular to both the longitudinal-direction and transverse direction.

Figure 38:
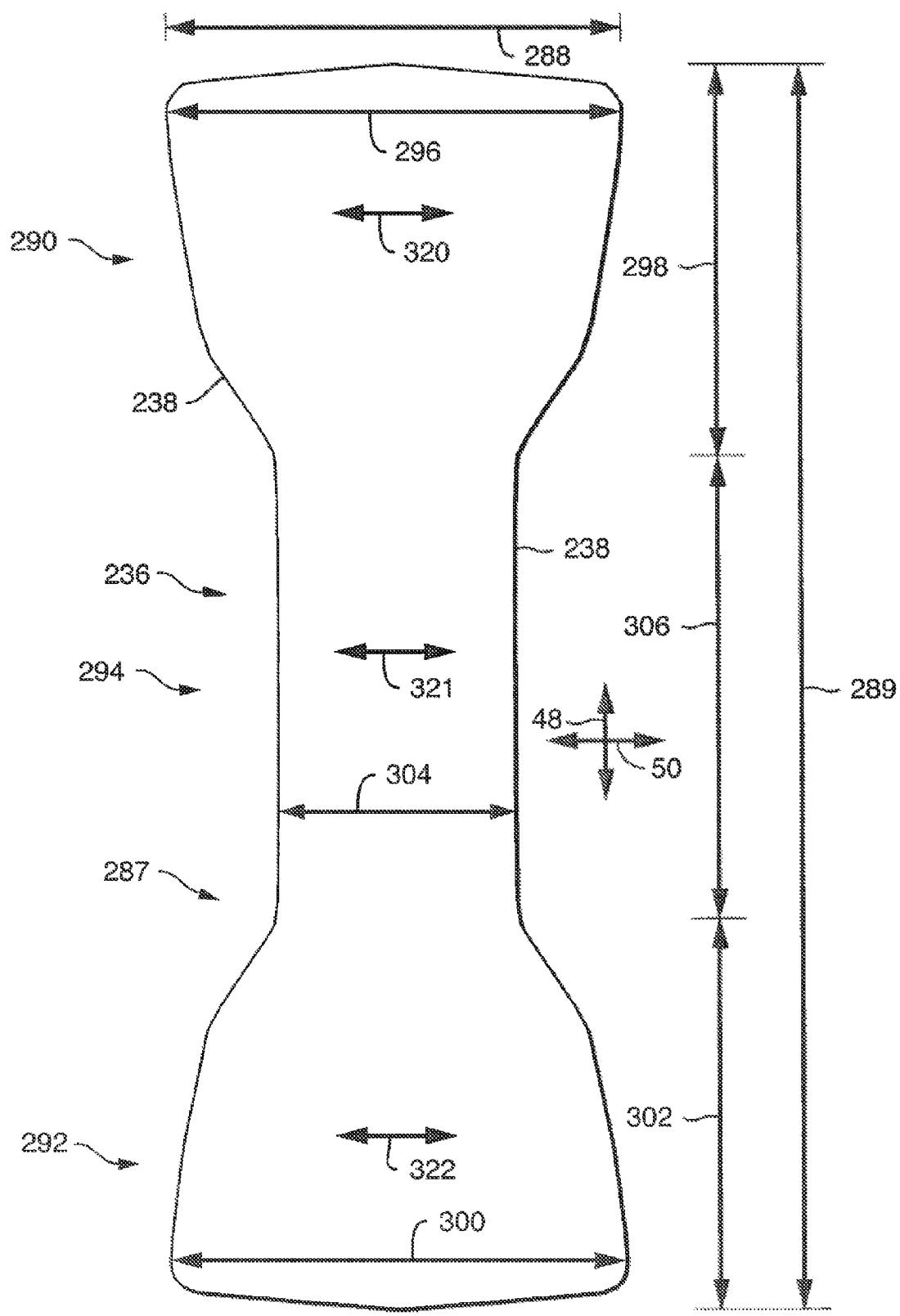
FIG. 38 representatively illustrates a top plan view of the absorbent core of FIG. 36.

The absorbent insert 230 includes a first sheet 232 and a second sheet 234 in facing relation with the first sheet 232. The absorbent insert 230 also includes an absorbent core 236 positioned between the first sheet 232 and the second sheet 234. FIG. 38 is a top plan view of the absorbent core 236 removed from the absorbent insert 230 of FIG. 35 to better illustrate detail. The absorbent core 236 defines a core perimeter 238, and the first sheet 232 and the second sheet 234 extend beyond the core perimeter 238, and are joined together to form a perimeter seal 240. The outer extent of the first sheet 232 and/or the second sheet 234 defines the absorbent insert perimeter 239. The absorbent insert perimeter 239 in turn defines an absorbent insert area 269.

The absorbent insert 230 defines an absorbent insert width 266 and an absorbent insert length 268. The absorbent insert 230 defines a first end section 270, a second end section 272, and a central section 274 in the longitudinal direction 48. The central section 274 extends between the first end section 270 and the second end section 272. The first end section 270 defines a first end section width 276 and a first end section length 278. The second end section 272 defines a second end section width 280 and a second end section length 282. The central section 274 defines a central section width 284 and a central section length 286. The first end section length 278 plus the second end section length 282 plus the central section length 286 equals the absorbent insert length 268. The widths of the various sections are measured in the transverse direction 50 and the lengths of the various sections are measured in the longitudinal direction 48.

In an embodiment adapted for use by a child weighing 60 to 120 pounds, the absorbent insert length may be 425 to 475 mm, or 430 to 450 mm, or about 440 mm. In an embodiment adapted for use by a child weighing 38 to 65 pounds, the absorbent insert length may be 375 to 425 mm, 390 to 410 mm, or about 400 mm. In various embodiments, the first end section length may equal the central section length which may equal the second end section length. In other embodiments, the first end section length may equal the second end section length and the central section length may be different. For example, the first end section length may be about 35% the absorbent insert length, the second end section length may be about 35% the absorbent insert length, and the central section length may be about 30% the absorbent insert length. In another example, the first end section length may be about 30% the absorbent insert length, the second end section length may be about 30% the absorbent insert length, and the central section length may be about 40% the absorbent insert length.

In various embodiments, the absorbent insert may have a width that varies at different points along the longitudinal direction. For example, as illustrated in FIG. 36, the absorbent insert 230 has a variable width at different points along the longitudinal direction. In this embodiment, the first end section 270 and the second end section 272 have a maximum width that is greater than the maximum width of the central section 274. For example, in some embodiments, the first end section and the second end section may have a maximum width of about 160 to 210 mm, 170 to 200 mm, 180 to 190 mm or about 186 mm. In these embodiments, the central section may have a maximum width of about 90 to 130 mm, about 100 to 120 mm, or about 114 mm.

In various embodiments, the first end section, the second end section, and/or the central section may have a variable width at different points along the longitudinal direction or may have a consistent width at different points along the longitudinal direction. In some embodiments, the first end section and the second end section may have variable width at different points along the longitudinal direction and the central section may have a consistent width at different points along the longitudinal direction as illustrated in FIG. 36. In some embodiments, the first end section and the second end section may have a width that varies from 186 mm at the maximum to 114 mm at the minimum. In these embodiments, the central section may have a consistent width of about 114 mm.

In some embodiments, the absorbent insert defines a first reference width 316 measured at ⅛ the absorbent insert length 268, a second reference width 317 measured at ½ the absorbent insert length 268, and a third reference width 318 measured at ⅞ the absorbent insert length 268. In some embodiments, the first reference width 316 may be equal to the third reference width 318 and the second reference width 317 may be less than the first and third reference widths 316 and 318. In some embodiments, the second reference width 317 may be less than 50%, 60%, 70%, or 80% the first reference width 316 and/or the third reference width 318. In some embodiments, the second reference width 317 may be about 60% the first reference width 316 and the third reference width 318.

The absorbent insert 230 also defines an absorbent insert area 269. In various embodiments, the absorbent insert area may be any suitable value. For example, in embodiments adapted for use by a child weighing 60 to 120 pounds, the absorbent insert area may be about 65,000 $mm^2$. In embodiments adapted for use by a child weighing 38 to 65 pounds, the absorbent insert area may be about 57,600 $mm^2$.

In various embodiments, the absorbent insert may define any suitable shape. For example, the absorbent insert may have a symmetric shape about the transverse centerline like that illustrated in FIG. 36 or may have an asymmetric shape about the transverse centerline like that illustrated in FIG. 39. In various embodiments, the absorbent inserts may have a rectangle shape, dog-bone shape, hourglass shape, T-shape, or the like.

Referring again to FIG. 38, the absorbent core 236 defines an absorbent core width 288 and an absorbent core length 289. The absorbent core 236 also defines a first end section 290, a second end section 292, and a central section 294 in the longitudinal direction 48. The central section 294 extends between the first end section 290 and the second end section 292. The first end section 290 defines a first end section width 296 and a first end section length 298. The second end section 292 defines a second end section width 300 and a second end section length 302. The central section 294 defines a central section width 304 and a central section length 306. The first end section length 298 plus the second end section length 302 plus the central section length 306 equals the absorbent core length 289. The widths of the various sections are measured in the transverse direction 50 and the lengths of the various sections are measured in the longitudinal direction 48.

In an embodiment adapted for use by a child weighing 60 to 120 pounds, the absorbent core length may be 350 to 450 mm, 375 to 425 mm, 390 to 410 mm, or about 400 mm. In an embodiment adapted for use by a child weighing 38 to 65 pounds, the absorbent core length may be 340 to 380 mm, 350 to 370 mm, or about 360 mm. In various embodiments, the first end section length may equal the central section length which may equal the second end section length. In other embodiments, the first end section length may equal the second end section length and the central section length may be different. For example, the first end section length may be about 25% the absorbent core length, the second end section length may be about 25% the absorbent core length, and the central section length may be about 50% the absorbent core length.

In another example, the first end section length may be about 30% the absorbent core length, the second end section length may be about 30% the absorbent core length, and the central section length may be about 40% the absorbent core length.

In various embodiments, the absorbent core may have a width that varies at different points along the longitudinal direction. For example, as illustrated in FIG. 38, the absorbent core 236 has a variable width at different points along the longitudinal direction. In this embodiment, the first end section 290 and the second end section 292 have a maximum width that is greater than the maximum width of the central section 294. For example, in various embodiments, the first end section and the second end section may have a maximum width of about 120 to 165 mm, 135 to 150 mm, or about 145 mm. In some embodiments, the maximum width is at least 120 mm, at least 130 mm, at least 140 mm, or at least 145 mm. In these embodiments, the central section may have a maximum width of about 55 to 95 mm, 65 to 85 mm or about 75 mm. In some embodiments, the central section may have a maximum width of less than 110, less than 100, less than 95, less than 90, less than 85, less than 80, or less than 75 mm.

In various embodiments, the first end section, the second end section, and/or the central section may have a variable width at different points along the longitudinal direction or may have a consistent width at different points along the longitudinal direction. In some embodiments, the first end section and the second end section may have variable width at different points along the longitudinal direction and the central section may have a consistent width at different points along the longitudinal direction as illustrated in FIG. 38. In some embodiments, the first end section and the second end section may have a width that varies from 145 mm at the maximum to 75 mm at the minimum. In these embodiments, the central section may have a consistent width of about 75 mm.

In some embodiments, the absorbent core defines a first reference width 320 measured at ⅛ the absorbent core length 289, a second reference width 321 measured at ½ the absorbent core length 289, and a third reference width 322 measured at ⅞ the absorbent core length 289. In some embodiments, the first reference width 320 may be equal to the third reference width 322 and the second reference width 321 may be less than the first and third reference widths 320 and 322. In some embodiments, the second reference width 321 may be less than 40%, 50%, 60%, 70%, or 80% the first reference width 320 and/or the third reference width 322. In some embodiments, the second reference width 321 may be about 50% the first reference width 320 and the third reference width 322.

The absorbent core also defines an absorbent core area. In various embodiments, the absorbent core area may be any suitable value. For example, in an embodiment adapted for use by a child weighing 60 to 120 pounds, the absorbent core area may be about 42,000 mm$^2$. In an embodiment adapted for use by a child weighing 38 to 65 pounds, the absorbent core area may be about 36,300 mm$^2$.

In various embodiments, the absorbent core may define any suitable shape. For example, the absorbent core may have a symmetric shape about the transverse centerline like that illustrated in FIG. 38 or may have an asymmetric shape about the transverse centerline like that illustrated in FIG. 39. In various embodiments, the absorbent cores may have a rectangle shape, dog-bone shape, hourglass shape, T-shape, or the like.

In various embodiments, the perimeter seal may have any suitable width and may be formed by any suitable method. Referring again to FIGS. 36-37, the perimeter seal width 241 is representatively illustrated. In some embodiments, the perimeter seal width may be at least 5, at least 10, at least 15, or at least 20 mm. The perimeter seal may include adhesive bonding, thermal bonding, ultrasonic bonding, pressure bonding, and the like, and combinations thereof. In some embodiments, the first sheet may be joined to the second sheet at the perimeter seal via adhesive bonding and the perimeter seal width may be at least 20 mm. In other embodiments, the first sheet may be joined to the second sheet at the perimeter seal via ultrasonic bonding and the perimeter seal width may be at least 10 mm.

In some embodiments, the absorbent insert may be substantially devoid of fluid-impervious materials. In some embodiments, the absorbent insert does not include a fluid-impervious barrier layer. In comparison, many absorbent articles include a fluid-impervious back sheet or baffle which is provided to prevent fluid from contacting the clothes of the wearer or a delay layer which is provided to slow or divert the fluid. In the present invention, the absorbent insert is positioned within the fluid-impervious pouch and thus does not require a fluid-impervious layer as part of the absorbent insert. Additionally, this design is believed to be beneficial in some embodiments over conventional inserts because fluid can be absorbed into the absorbent insert along the entire pad, including the body-facing surface, the garment-facing surface, and the sides. Additionally, the omission of a fluid-impervious layer eliminates the risk of fluid being trapped between the fluid-impervious pouch and the absorbent insert which might cause leaking during use or leaking when removing the absorbent insert from the pouch.

In some embodiments, the absorbent insert may further include one or more intake layers. For example, the absorbent insert 230 of FIGS. 36 and 37 is illustrated with a first intake material 242 positioned between the first sheet 232 and the absorbent core 236. In some embodiments, the absorbent insert may additionally or alternatively include a second intake material. For example, the absorbent insert 244 of FIGS. 39 and 40 is illustrated with a first intake material 242 and a second intake material 246.

Figure 39:
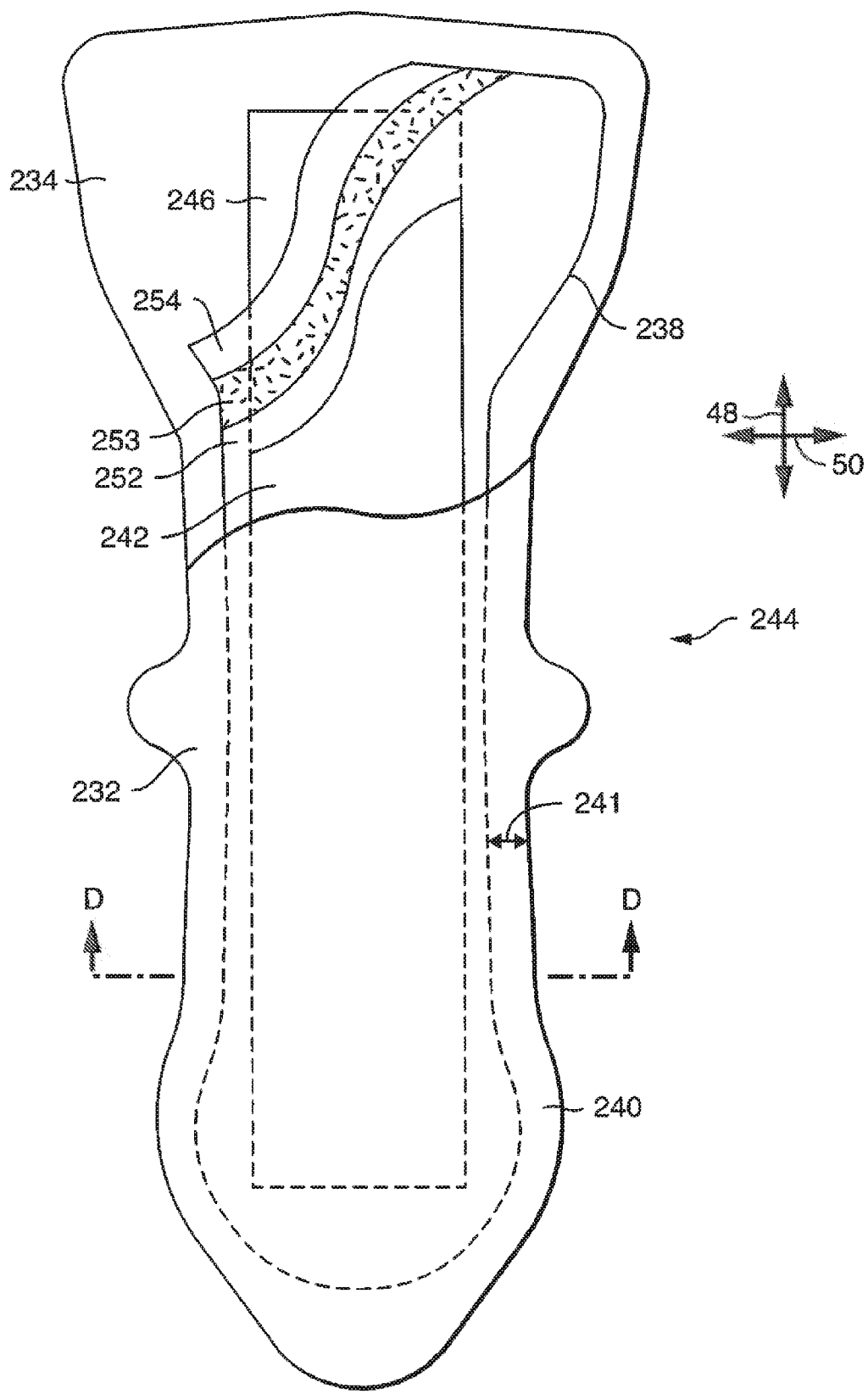
FIG. 39 representatively illustrates a top plan view of another exemplary absorbent insert of the present invention with portions cut away to illustrate underlying structure.
Figure 40:
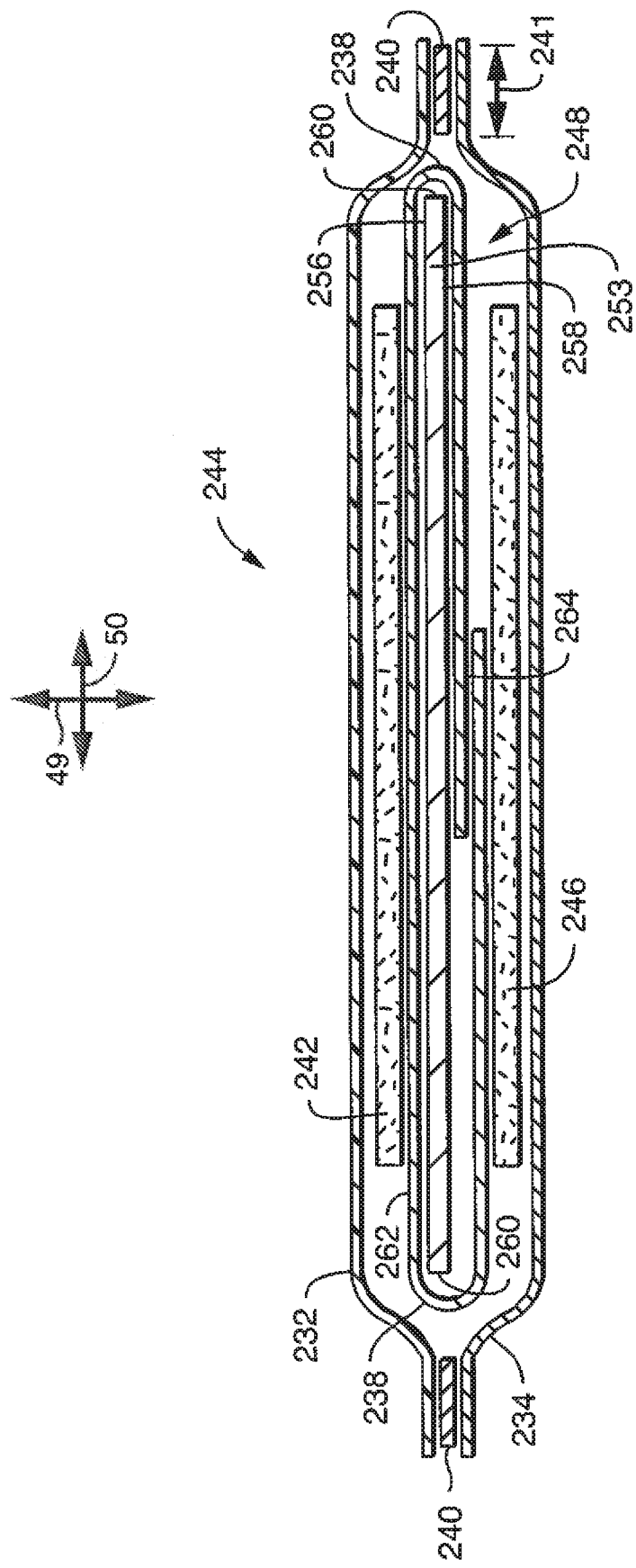
FIG. 40 representatively illustrates a cross sectional view of the absorbent insert of FIG. 39 taken along the line D-D.

Referring now to FIGS. 39 and 40, a second exemplary absorbent insert 244 is representatively illustrated. FIG. 39 is a top plan view of the absorbent insert 244 with portions cut away to better illustrate underlying structure. FIG. 40 is an expanded cross-sectional view of the absorbent insert of FIG. 39 taken along the line D-D. The absorbent insert 244 includes a first sheet 232 and a second sheet 234 in facing relation with the first sheet 232. The absorbent insert 244 also includes an absorbent core 248 positioned between the first sheet 232 and the second sheet 234. The absorbent core 248 defines a core perimeter 238 and the first sheet and the second sheet extend beyond the core perimeter 238 and are joined together to form a perimeter seal 240.

The first intake material 242 is positioned between the absorbent core 248 and the first sheet 232 and the second intake material 246 is positioned between the absorbent core 248 and the second sheet 234.

In various embodiments, the first intake material and/or the second intake material may have any suitable length, width, or shape. For example, referring again to FIG. 35, the first intake material 242 defines an intake material width 324 and an intake material length 325. In various embodiments, the intake material width may be 50 to 70 mm or about 62 mm. In these embodiments, the intake material width may be at least 70%, 80%, or 90% the second reference width 317 of the absorbent core. In some embodiments, the intake material width may be about 84% the second reference width 317 of the absorbent core.

In some embodiments, the intake material length may be about 325 to 375 mm, 340 to 360 mm, or about 355 mm. In these embodiments, the intake material length may be at least 70%, 80%, or 90% the absorbent core length. In some embodiments, the intake material length may be about 88% the absorbent core length.

In various embodiments, the intake materials may be rectangular as illustrated in FIG. 36 or may be any other suitable shape. For example, in various embodiments, the intake materials may be shaped similarly to the absorbent insert and/or the absorbent core.

In various embodiments, any of the absorbent inserts of the present invention may include absorbent cores having absorbent material and one or more wrap sheets. For example, in some embodiments, the absorbent cores may include a single wrap sheet folded around the longitudinal side edges of the absorbent material and overlapping upon itself to form a fully wrapped absorbent core. In other embodiments, the absorbent core may include two wrap sheets. In these embodiments, one of the wrap sheets may be primarily positioned on a first-facing surface of the absorbent material. The other wrap sheet may be primarily positioned on the second-facing surface of the absorbent material. In these embodiments, the wrap sheet on the second-facing surface may extend to the longitudinal side edges of the absorbent material, may wrap around the longitudinal side edges of the absorbent material, or may extend to the first-facing surface of the absorbent material. Likewise, the wrap sheet on the first-facing surface may extend to the longitudinal side edges of the absorbent material, may wrap around the longitudinal side edges of the absorbent material, or may extend to the second-facing surface of the absorbent material. The wrap sheets may overlap themselves or may overlap each other.

Referring again to FIG. 36, the absorbent core 236 is representatively illustrated with a first wrap sheet 252 positioned on a first-facing surface 256 of the absorbent material 253. The first wrap sheet 252 extends between the longitudinal side edges 260 of the absorbent material 253. The absorbent core 236 also includes a second wrap sheet 254 positioned on a second-facing surface 258 of the absorbent material 253. The second wrap sheet 254 extends between the longitudinal side edges 260 of the absorbent material 253.

Referring again to FIG. 40, the absorbent core 248 is representatively illustrated with a wrap sheet 262 positioned on a first-facing surface 256 of the absorbent material 253. The wrap sheet 262 extends around the longitudinal side edges 260 of the absorbent material 253 and is also positioned on a second-facing surface 258 of the absorbent material 253. The wrap sheet 262 may at least partially overlay itself at overlap 264.

In various embodiments, the first sheet and the second sheet may be made of the same material or may be different. In some embodiments, the first sheet and the second sheet may have the same basis weight or may be different. The first sheet and/or the second sheet may be fluid permeable and may be made of substantially hydrophobic fibrous material. For example, the first sheet and/or the second sheet may be a spunbond web composed of synthetic polymer filaments. In some embodiments, the first sheet and/or the second sheet may be a meltblown web or a bonded-carded-web composed of synthetic polymer filaments. Suitable synthetic polymers include, for example, polyethylene, polypropylene, polyester, and the like, and combinations thereof. In some embodiments, both the first sheet and the second sheet are spunbond polypropylene nonwoven webs having an individual basis weight of about 15 gsm. In some embodiments, the first sheet and/or the second sheet may be treated with surfactants to adjust the degree of hydrophobicity and wettability. In some embodiments, the first sheet and/or the second sheet may be embossed, apertured, slit, or otherwise mechanically worked.

The absorbent core typically includes absorbent material composed of airlaid, cellulosic fibers commonly referred to as wood pulp fluff. Other natural fibers, such as cotton, may also be employed to form the absorbent core. The absorbent core can have a density ranging from about 0.18-0.30 grams/cc. This density range allows the absorbent core to be sufficiently flexible to readily conform to the body of the wearer yet maintain sufficient rigidity for insertion into the pouch. In some embodiments, the absorbent core may have a density of about 0.24 grams/cc. The absorbent core may alternatively or additionally include a coform material composed of a mixture of cellulosic fibers and synthetic polymer fibers. For example, the coform material may be composed of an airlaid blend of cellulosic fibers and meltblown polyolefin fibers, such as polyethylene and/or polypropylene fibers. In addition, the absorbent core may have a dry thickness of about 3 to 5 mm or about 4 mm, as measured under a restraining pressure of 0.068 psi (0.47 kPa).

The absorbent core may also include an effective amount of an inorganic or organic high-absorbency (e.g., superabsorbent) material to enhance the absorptive capacity of the absorbent body. For example, the absorbent core can contain 5-95 weight percent high-absorbency material, and preferably includes about 30-70, 40-60, or about 50 weight percent of the high-absorbency material to provide more efficient performance. In some embodiments, the absorbent core can include equal amounts of fluff and superabsorbent. For example, in some embodiments, the absorbent core may include at least 14, at least 15, at least 16, at least 17, at least 18, or at least 19 grams of superabsorbent. In some embodiments, the absorbent core may include at least 14, at least 15, at least 16, at least 17, at least 18, or at least 19 grams of fluff. In some embodiments, the absorbent core may include about 19 grams of superabsorbent and about 19 grams of fluff. In other embodiments, the absorbent core may include about 17 grams of superabsorbent and about 17 grams of fluff.

Suitable inorganic high-absorbency materials include, for example, absorbent clays and silica gels. Organic high-absorbency materials can include natural materials, such as agar, pectin, guar gum and peat moss, as well as synthetic materials, such as synthetic hydrogel polymers. Such hydrogel polymers include, for example, carboxymethylcellulose, alkali metal salts of polyacrylic acids, polyacrylamides, polyvinyl ethers, hydroxypropyl cellulose, polyvinyl morpholinone, polymers and copolymers of vinyl sulfonic acid, polyacrylates, polyacrylamides, polyvinyl pyridine and the like. Other suitable polymers include hydrolyzed acrylonitrile grafted starch, acrylic acid grafted starch, and isobutylene maleic anhydride copolymers, and mixtures thereof. The hydrogel polymers are preferably lightly cross-linked to impart desired levels of water insolubility to the material.

In some embodiments, the wrap sheet may be woven or non-woven material and may be made of any suitable material. For example, the wrap sheet may be made of polypropylene, cellulosic tissue, and the like, and combinations thereof. In some embodiments, the wrap sheet may be nonwoven material made from spunbond polypropylene and may have a basis weight of about 10 gsm.

The intake layer or layers help to decelerate and diffuse surges or gushes of fluid that can be rapidly introduced into the absorbent insert. Desirably, the intake layer can rapidly accept and temporarily hold the fluid prior to releasing the fluid into the absorbent core of the absorbent insert. In some embodiments, the intake layer may be a through air bonded carded web composed of 40% hollow polypropylene fibers (6 denier) and 60% bicomponent fibers (6 denier) (bicomponent sheath: polypropylene core). In various embodiments, the intake layer may have any suitable basis weight. For example, the intake layer may have a basis weight of at least 30, at least 50, at least 75, at least 100, or at least 125 grams per square meter (gsm). In some embodiments, the intake layer may have a basis weight of about 128 gsm. Other examples of suitable intake layers are described in U.S. Pat. No. 5,486,166; U.S. Pat. No. 5,490,846; and U.S. Pat. No. 5,820,973. The entire disclosures of these patents are hereby incorporated by reference herein to the extent they are consistent (i.e., not in conflict) herewith.

In some embodiments, the absorbent insert may have a first intake layer and a second intake layer. In some embodiments, the first intake layer may be the same material as the second intake layer or may be different. In some embodiments, the first intake layer may have the same basis weight as the second intake layer or may be different.

In some embodiments, the absorbent inserts of the present invention may be characterized, at least in part, by specific absorbent properties. For example, in some embodiments, the absorbent inserts may have a total absorbent capacity of at least 600 grams, at least 650 grams, at least 700 grams, or at least 750 grams of 0.9% saline solution. In some embodiments, the absorbent inserts may have an absorbent capacity of about 740 grams or about 827 grams. The total absorbent capacity of the absorbent inserts may be determined by using the Retention Capacity Test Method. This test method measures the amount of fluid retained by an absorbent insert under external pressure. An initial weight of the absorbent insert is measured and then the absorbent insert is submerged in a 0.9% saline solution for 20 minutes. After the saturation time, 0.5 psi pressure is applied across the entire absorbent insert for 5 minutes and the excess saline solution is allowed to drain. After the pressure time, the weight of the saturated absorbent insert is measured. The total absorbent capacity is calculated as the saturated weight minus the initial weight.

In some embodiments, the absorbent inserts may have a first intake rate as measured through a first major surface and may have a second intake rate as measured through a second major surface which is opposite the first major surface. In some embodiments, the first major surface may be adapted for positioning towards the wearer's body and the second major surface may be adapted for positioning towards the fluid-impervious pouch (i.e., towards the wearer's garments). In some embodiments, the first intake rate and/or the second intake rate may be determined by the Cradle Intake Test method. This test measures the time required for an absorbent insert to absorb a specific volume of 0.9% saline solution (insult). The absorbent insert is positioned within a test cradle with the first major surface (body-facing surface) up and the second major surface (garment-facing surface) down toward the cradle to determine the first intake rate. The absorbent insert is positioned within a test cradle with the second major surface (garment-facing surface) up and the first major surface (body facing surface) down towards the cradle to determine the second intake rate. The insult location is located relative to the transverse center line of the pant. For products designed for wearers having a weight of 38 to 65 pounds, the insult location is 150 mm forward of the transverse centerline for boys and is 90 mm forward of the transverse centerline for girls and the insult volume is 120 ml for both. For products designed for wearers having a weight of 60 to 120 pounds, the insult location is 170 mm forward of the transverse centerline for boys and 80 mm forward of the transverse centerline for girls and the insult volume is 220 ml for both. The flow rate of the saline solution is 15 ml/sec and the saline has a temperature of 98.6 degrees F. The respective absorbent inserts are insulted a first time at the aforementioned locations, volumes, and flow rates. The time it takes for the absorbent insert to completely absorb the first insult is recorded. After 15 minutes, the respective absorbent inserts are insulted a second time at the aforementioned locations, volumes, and flow rates. The time it takes for the absorbent insert to completely absorb the second insult is recorded.

In some embodiments, the first intake rate may be less than 30 seconds for the first insult and less than 100 seconds for the second insult. In some embodiments, the second intake rate may be less than 30 seconds for the first insult and less than 100 seconds for the second insult. In some embodiments, the ratio of the first intake rate to the second intake rate for the first insult may be at least 1:3, at least 1:2, at least 1:1.5, or about 1:1.

In some embodiments, the absorbent inserts may be characterized by total absorbent capacity as a ratio of crotch width. In some embodiments, the products designed for wearers having a weight of 60 to 120 pounds may have an absorbent capacity of about 827 grams and a crotch width of about 74 mm. In other embodiments, the products designed for wearers having a weight of 38 to 65 pounds may have an absorbent capacity of about 740 grams and a crotch width of about 74 mm. Thus, in some embodiments, the ratio of total absorbent capacity to crotch width may be at least 9 g/mm, at least 10 g/mm, or at least 11 g/mm.

The absorbent inserts of the present invention may be provided in any suitable manner. For example, the absorbent inserts may be folded, stacked, wrapped, compressed, or the like, and combinations thereof. In some embodiments, the absorbent inserts may be individually wrapped in a wrapper. In some embodiments, the absorbent inserts may be folded one or more times before being placed in a wrapper. In some embodiments, the absorbent inserts may be folded twice before being placed in the wrapper.

In some embodiments, the absorbent inserts of the present invention include a first sheet, a second sheet, an intake layer, and an absorbent core. In these embodiments, the absorbent core may be positioned between the first sheet and the second sheet. Additionally, the intake layer may be positioned between the first sheet and the absorbent core. In this configuration, the first sheet is designated the body side and the second sheet is designated as the garment side of the absorbent insert.

In various embodiments, the absorbent insert may be folded a first time such that a first portion of the body side is in facing relation with a second portion of the body side. In these embodiments, the absorbent insert may be folded a second time such that a third portion of the body side is in facing relation with a first portion of the garment side. In other embodiments, the absorbent insert may be folded a first time such that a first portion of the garment side is in facing relation with a second portion of the garment side. In these embodiments, the absorbent insert may be folded a second time such that a third portion of the garment side is in facing relation with a first portion of the body side.

In some embodiments, the first fold may be positioned such that the absorbent insert is effectively folded into equal halves. In some embodiments, the first fold and the second fold may be positioned such that the absorbent insert is effectively folded into approximately equal thirds.

In various embodiments, the folded absorbent inserts may be individually packaged in any suitable wrapper material. Conventionally, the wrapper consists of one or more layers of a thin sheet or film of thermoplastic material, such as polyethylene, which is folded around the absorbent article and then sealed by the use of heat and/or pressure, ultrasonics, or an adhesive to form a package or pouch. In various embodiments, the wrapper may include films made from poly(vinyl alcohol), polyvinyl acetate, ethylene vinyl alcohol, polyurethane, ethylene methyl acrylate, and ethylene methyl acrylic acid to make them breathable. In some embodiments, the wrapper material may also be a laminate of different materials, such as a film/nonwoven laminate. The package may have a sealed side or edge that is designed to be opened by breaking or tearing the material at or adjacent the seal in order to subsequently remove the absorbent insert. With some package designs, a flap is provided that folds over the pouch opening and may attach to the front of the pouch with adhesive applied between the pouch and flap, or with a piece of adhesive tape. The sides of the flap may be sealed with the sides of the pouch and may be separated prior to removing the absorbent article.

The containment pants and the absorbent inserts of the present invention are adapted to work together as a containment system. In various embodiments, the containment system includes one or more containment pants like those described herein and one or more absorbent inserts like those described herein. Suitable containment systems are also described in patent application U.S. Ser. No. 13/548,012, entitled "Containment System", filed on Jul. 12, 2012, and having attorney docket number 64816460U503, the entirety of which is incorporated herein by reference.

In use and prior to donning, the absorbent inserts are positioned within the pouch which is suspended within the containment pant. After the absorbent insert is positioned, the containment system is pulled into place like conventional underwear. The containment pant is adapted to hold the absorbent insert in position to accept one or more urine insults from the wearer. The absorbent insert is adapted to rapidly intake and absorb the urine. The pouch is fluid-impervious and is adapted to hold any urine that may not be immediately absorbed by the absorbent insert. In some embodiments, the absorbent insert is fluid permeable on the garment-facing surface and/or on the side edges as well as the body-side surface. As such, any urine retained by the fluid-impervious pouch may be drawn into the absorbent insert via the garment-facing surface and/or the side edges. The used absorbent insert can be removed from the fluid-impervious pouch and the containment pant may be laundered prior to reuse with a new absorbent insert.

In various embodiments, the absorbent inserts of the present invention may be secured in the pouches of the containment pants by any suitable means. For example, the absorbent inserts may be secured in the pouches via buttons, snaps, hook and loop fasteners, pressure sensitive adhesive, clasps, and the like, and combinations thereof. In some embodiments, the absorbent inserts may be additionally or alternatively held in place by the structure of the containment flaps of the fluid-impervious pouch. For example, the containment flaps may include end pockets that help secure a portion of the absorbent insert within the pouches. In some embodiments, the containment flaps may include flap elastic that provides retractive forces that assist in securing the absorbent insert within the pouch. In some embodiments, the absorbent inserts are held in place only by the structure of the containment flaps and/or end pockets. In some embodiments, the absorbent inserts are held in place only by the structure of the containment flaps and the containment flap elastic and are devoid of fasteners. In some embodiments, the absorbent inserts are devoid of containment flaps. In these embodiments, the containment of the fluid is managed by the containment flaps of the pouch.

In various embodiments, the containment system may include a containment pant having a pouch with a pouch floor area, a length, width, and/or shape adapted to accommodate a specific absorbent insert having a complementary absorbent insert and/or absorbent core area, length, width, and/or shape. This complementary area, length, width, and/or shape is believed to improve the absorbent insert placement on the body, to help contain the absorbent insert within the pouch, and to provide a smooth discrete fit and appearance for discretion.

In some embodiments, a containment pant may have a pouch with a pouch floor having a pouch floor length. Likewise, the absorbent insert may have an absorbent insert length and/or an absorbent core length that is less than or equal to the pouch floor length. In some embodiments, the absorbent insert length and/or an absorbent core length may be at least 70%, at least 80%, at least 90%, or at least 95% the pouch floor length. In one embodiment, the absorbent core length may be 91% of the pouch floor length. In these embodiments, the absorbent insert length and/or an absorbent core length may be 100% or less of the pouch floor length. Having an absorbent insert length and/or an absorbent core length to pouch floor length in these ranges is believed to keep the absorbent insert secure within the pouch without excessive bunching or shifting that may adversely affect performance and/or comfort. An absorbent insert shorter than this range would be more likely to shift or breach the pouch gasket which would likely result in leakage. An absorbent insert longer than this range would be more likely to buckle and bunch within the pouch and may result in a poor user experience due to discomfort and/or loss of discretion.

In some embodiments, a containment pant may have a pouch with a pouch floor having a pouch floor maximum width and a pouch floor minimum width wherein the maximum width and the minimum width are different. Likewise, the absorbent insert may have an absorbent insert and/or absorbent core maximum width and an absorbent insert and/or absorbent core minimum width wherein the maximum width and the minimum width are different. In some embodiments, the absorbent insert and/or the absorbent core maximum width is at least 80%, at least 90%, or at least 95% the pouch floor maximum width. In one embodiment, the absorbent core maximum width is 85% of the pouch floor maximum width. In these embodiments, the absorbent insert and/or absorbent core maximum width may be 100% or less of the pouch floor maximum width. In some embodiments, the absorbent insert and/or the absorbent core minimum width is at least 80%, at least 90%, or at least 95% the pouch floor minimum width. In one embodiment, the absorbent core minimum width may be 91% of the pouch floor minimum width. In these embodiments, the absorbent insert and/or the absorbent core minimum width may be 100% or less of the pouch floor minimum width.

In some embodiments, a containment pant may have a pouch with a pouch floor having a pouch floor maximum width in a front portion and/or a back portion and a pouch floor minimum width at a central portion wherein the maximum width and the minimum width are different. Likewise, the absorbent insert and/or absorbent core may have an absorbent insert and/or absorbent core maximum width in a front portion and/or a back portion and an absorbent insert and/or absorbent core minimum width at a central portion wherein the maximum width and the minimum width are different. In some embodiments, the minimum width of the pouch floor may be less than 80%, less than 70%, less than 60%, or about 62% the maximum width of the pouch floor. Similarly, the minimum width of the absorbent insert and/or absorbent core may be less than 80%, less than 70%, less than 60%, or about 62% the maximum width of the absorbent insert and/or absorbent core.

In one embodiment, the present invention is a method for providing a containment system. The method includes providing a permanently closed containment pant having a pouch like those disclosed herein. The pouch defines a pouch floor having a longitudinal direction, a first end section, a second end section, and a central section extending between the first end section and the second end section. The first end section, the second end section, and the central section define equal lengths in the longitudinal direction and together define a pouch floor length. The first end section defines a maximum width of at least 130 mm, at least 140 mm, at least 150 mm, or at least 165 mm, the central section defines a maximum width of less than 110 mm, less than 100 mm, less than 95 mm, and the second end section defines a maximum width of at least 130 mm, at least 140 mm, at least 150 mm, or at least 165 mm. The permanently closed containment pant may be substantially devoid of an integrated absorbent core. The method further includes providing a discrete absorbent insert like those disclosed herein. The discrete absorbent insert includes an absorbent core that defines a longitudinal direction, a first end section, a second end section, and a central section. The central section is positioned between the first end section and the second end section. The first end section, the second end section, and a central section define equal lengths in the longitudinal direction. The first end section defines a maximum width of at least 115 mm, at least 125 mm, or at least 135 mm, the central section defines a maximum width of less than 100 mm, less than 90 mm, or less than 85 mm, and the second end section defines a maximum width of at least 115 mm, at least 125 mm, or at least 135 mm. The discrete absorbent insert may be devoid of a fluid impervious layer.

In some embodiments, a containment pant may have a pouch with a pouch floor having a pouch floor area. Likewise, the absorbent insert may have an absorbent insert area and/or absorbent core area that is less than or equal to the pouch floor area. In some embodiments, the absorbent insert area and/or absorbent core area may be at least 80%, at least 90%, or at least 95% the pouch floor area. In some embodiments, the absorbent core area is 76% of the pouch floor area. In these embodiments, the absorbent insert area and/or absorbent core area may be 100% or less of the pouch floor area. For example, in one embodiment, the absorbent core area may be about 42,218 mm$^2$ which is 76% of the pouch floor area of about 55,270 mm$^2$. In another embodiment, the absorbent core area may be about 36,296 mm$^2$ which is 76% of the pouch floor area of about 47,778 mm$^2$.

In some embodiments, a containment pant may have a pouch with a pouch floor having a pouch floor shape and the absorbent insert and/or absorbent core may have an absorbent insert shape and/or absorbent core shape that is substantially the same as the pouch floor shape. In one embodiment, the pouch floor may have a curvilinear perimeter in the shape of a bow-tie and the absorbent insert and/or absorbent core may have a curvilinear perimeter in the shape of a bow-tie of similar length and/or width. For example, the pouch floor may have a bow-tie shape like that illustrated in FIG. 28 and the absorbent core may have a bow-tie shape like that illustrated in FIG. 37. In another embodiment, the pouch floor may have a curvilinear perimeter in the shape of a torch and the absorbent insert and/or absorbent core may have a curvilinear perimeter in the shape of a torch of similar length and/or width. For example, the pouch floor may have a torch shape like that illustrated in FIG. 11 and the absorbent core may have a torch shape like that illustrated in FIG. 38.

In some embodiments, the containment system of the present invention provides a first containment pant, a second containment pant, and an absorbent insert. In these embodiments, the first containment pant has a first configuration and the second containment pant has a second configuration that is different than the first configuration. For example, in some embodiments, the first containment pant may have a chassis designed for use by males like that illustrated in FIG. 1 while the second containment pant may have a chassis designed for use by females like that illustrated in FIG. 6. The differences between the first containment pant and the second containment pant may include chassis shape, chassis design, sling construction, pouch construction, pouch location, and the like, and combinations thereof. For example, in the first containment pant, the pouch may be located more towards the front of the containment pant for better alignment with male anatomy. In contrast, in the second containment pant, the pouch may be more centrally located for better alignment with female anatomy.

In one embodiment, the present invention provides a method for providing a containment system that includes providing a first permanently closed containment pant like those disclosed herein and a second permanently closed containment pant like those disclosed herein. The first containment pant includes a first fluid-impervious pouch that defines a first pouch construction and a first pouch floor. The first pouch floor having a first end section, a second end section and a central section extending between the first end section and the second end section. The first end section of the first containment pant defines a maximum width of at least 135 mm, at least 145 mm, at least 155 mm, or at least 165 mm, the central section of the first containment pant defines a minimum width of less than 110 mm, less than 100 mm, or less than 95 mm, and the second end section of the first containment pant defines a maximum width of at least 135 mm, at least 145 mm, at least 155 mm, or at least 165 mm. Similarly, the second containment pant includes a second fluid-impervious pouch that defines a second pouch construction and a second pouch floor. The second pouch floor having a first end section, a second end section and a central section extending between the first end section and the second end section. The first end section of the second containment pant defines a maximum width of at least 135 mm, at least 145 mm, at least 155 mm, or at least 165 mm, the central section of the second containment pant defines a minimum width of less than 110 mm, less than 100 mm, or less than 95 mm, and the second end section of the second containment pant defines a maximum width of at least 135 mm, at least 145 mm, at least 155 mm, or at least 165 mm. In some embodiments, the first pouch floor defines a first pouch floor length and the second pouch floor defines a second pouch floor length that is 95% to 105% the first pouch floor length. Thus, the first pouch floor has the same or similar dimensions at the same or similar positions as does the second pouch floor. However, while the first pouch construction may be any suitable construction, including those disclosed herein, and the second pouch construction may be any suitable construction, including those disclosed herein, the first pouch construction may be different than the second pouch construction. For example, in some embodiments the first pouch construction may be like that illustrated in FIGS. 28-31 and the second pouch construction may be like that illustrated in FIGS. 17-22.

In some embodiments, the first permanently closed containment pant includes a first containment sling having a first transition that is joined between the first fluid-impervious pouch and the front waist region. The first transition defines a length in a longitudinal direction. The first permanently closed containment pant includes a second transition that is joined between the first fluid-impervious pouch and the back waist region. The second transition defines a length in the longitudinal direction. In these embodiments, the second permanently closed containment pant includes a second containment sling having a first transition that is joined between the second fluid-impervious pouch and the front waist region. The first transition defines a length in a longitudinal direction. The second permanently closed containment pant includes a second transition that is joined between the second fluid-impervious pouch and the back waist region. In some embodiments, the length of the first transition of the first sling is greater than the length of the first transition of the second sling. In some embodiments, the length of the second transition of the first sling is less than the length of the second transition of the second sling.

However, despite the differences between the first containment pant and the second containment pant, both may be constructed with pouches having pouch floors having similar length, width, and/or shape. As such, a single absorbent insert may be provided for use with both the first containment pant and the second containment pant. For example, in some embodiments, the present invention provides a method for providing a containment system. The method includes providing a first permanently closed containment pant like those described herein and providing a second permanently closed containment pant like those described herein. The method also includes providing a discrete absorbent insert that is sized and shaped to work in conjunction with both the first containment pant and the second containment pant. In some embodiments, the first containment pant may include a first pouch and the second containment pant may include a second pouch having a similar size and shape to the first pouch. However, despite the similarities, the first containment pant and the second containment pant may have different chassis construction, pouch construction, sling construction, pouch placement, or other differences, or combinations thereof.

In some embodiments, the containment system of the present invention includes one or more absorbent inserts having a designated body side and a designated garment side. In other words, in some embodiments, the absorbent inserts are designed to be oriented with a particular side towards the user to maximize the performance of the absorbent insert. For example, in some embodiments, the absorbent insert may have a single intake layer located on one side of the absorbent core. In these embodiments, it is desirable for the user to orient the absorbent insert within the pouch such that the intake layer faces the user. In this orientation, the absorbent insert is positioned to intake fluid rapidly through the intake layer and retain the fluid in the absorbent core.

To assist users in properly orienting the absorbent insert in the pouch, various cues may be provided. In some embodiments, the absorbent insert may include a color on one or more of the components. In some embodiments, the absorbent insert may include an intake layer that has a color that is distinguishable from the other components of the absorbent insert. For example, in some embodiments, the intake layer may have a blue color and the surrounding components may have a white color. In these embodiments, the user may be directed to identify the blue intake layer and position it facing the body. In this way, the user has a simple visual cue to quickly, repeatably, and properly orient the absorbent insert within the pouch.

In some embodiments, the absorbent inserts may be provided folded in individual wrappers. In these embodiments, the absorbent inserts may be folded to define a direction of curvature. The absorbent inserts may be bi-folded, tri-folded, or the like. In these embodiments, the absorbent inserts may be folded such that the resulting curvature is directed to the side of the absorbent insert that is desirably oriented towards the wearer. For example, the absorbent insert may have a single intake layer located on one side of the absorbent core. The absorbent insert may be folded such that the absorbent insert is cupped towards the side having the intake layer. In use, this cupped formation naturally fits with the cupped formation of the pouches within the containment pants. As such, the user is cued to position the absorbent insert within the pouch with the intake layer oriented towards the body of the wearer.

While the invention has been described in detail with respect to specific embodiments thereof, it will be appreciated that those skilled in the art, upon attaining understanding of the foregoing will readily appreciate alterations to, variations of, and equivalents to these embodiments. Accordingly, the scope of the present invention should be assessed as that of the appended claims and any equivalents thereto. Additionally, all combinations and/or sub-combinations of the disclosed embodiments, ranges, examples, and alternatives are also contemplated.

The invention claimed is:

1. A permanently closed containment pant comprising,
   an elastically extensible chassis defining a waist opening, a first leg opening, and a second leg opening, the waist opening comprising a front waist region joined with a back waist region, wherein the chassis has a transverse elongation of between 125% and 175% at 2000 g*f and a longitudinal elongation of between 125% and 175% at 2000 g*f, and
   a sling positioned within the chassis and being joined to the front waist region and the back waist region, wherein the sling comprises a fluid-impervious base sheet and a containment flap joined with the base sheet to create a fluid-impervious pouch, the sling further comprising a first transition and a second transition that are elastically extensible in a longitudinal direction and in a transverse direction, wherein the base sheet is a fabric to define a first fabric surface and the containment flap is a fabric to define a second fabric surface wherein the base sheet is joined with the containment flap, wherein the base sheet has a transverse elongation of between 10% and 40% at 1400 g*f and a longitudinal elongation of between 10% and 40% at 1400 g*f;
   wherein the base sheet is a first fabric laminated with polyurethane to define a polyurethane surface and a fabric surface and the containment flap is a second fabric laminated with polyurethane to define a second fabric surface and a second polyurethane surface wherein the first polyurethane surface is joined with the second polyurethane surface.

2. The permanently closed containment pant of claim 1 wherein the sling further comprises the first transition and the second transition that are elastically extensible in a longitudinal direction and in a transverse direction.

3. The permanently closed containment pant of claim 2 wherein the base sheet is a woven polyester fabric laminated with a polyurethane sheet.

4. The permanently closed containment pant of claim 3 wherein the first transition is a discrete piece of material joined between the pouch and the waist elastic in the front waist region and wherein the second transition is a discrete piece of material joined between the pouch and the waist elastic in the back waist region.

5. The permanently closed containment pant of claim 3 wherein the chassis includes a shell material and wherein the first transition is an integral part of and a distinct projection of the shell material joined between the pouch and the waist elastic in the front waist region and wherein the second transition is a discrete piece of material joined between the pouch and the waist elastic in the back waist region.

6. The permanently closed containment pant of claim 1 wherein the sling is attached to the chassis in a crotch region with a tab and wherein
   the tab is a discrete piece of material and is ultrasonically bonded to the pouch and is sewed with thread to the chassis; or
   the tab is an integral part of the containment flap, is a distinct projection of the containment flaps, and is sewed with thread to the chassis; or
   the tab is an integral part of the base sheet, is a distinct projection of the base sheet, and is sewed with thread to the chassis.

7. The permanently closed containment pant of claim 1 wherein the fluid-impervious pouch defines a pouch floor having a first end section, a second end section, and a central section extending between the first end section and the second end section, wherein the first end section defines a maximum width, the second end section defines a maximum width equal to the maximum width of the first end section, and the central section defines a maximum width that is less than 70% the maximum width of the first and second end sections.

8. The permanently closed containment pant of claim 1 wherein the chassis comprises a shell material made of cotton and 2-25% spandex.

9. The permanently closed containment pant of claim 1 further comprising
   a waistband extending around 100% of the waist opening and being cantilevered relative to a shell material and
   a first leg elastic extending around 100% of the first leg opening and a second leg elastic extending around 100% of the second leg opening, wherein the first leg elastic and the second leg elastic are cantilevered relative to the shell material.

10. A permanently closed containment pant comprising,
   an elastically extensible chassis defining a waist opening, a first leg opening, and a second leg opening, the waist opening comprising a front waist region joined with a back waist region, wherein a peak load of the chassis in the transverse direction and in the longitudinal direction is between about 10,000 grams force and about 30,000 grams force, and
   a sling positioned within the chassis and being joined to the front waist region and the back waist region, wherein the sling comprises a fluid-impervious base sheet and a containment flap joined with the base sheet to create a fluid-impervious pouch, the sling further comprising a first transition and a second transition that are elastically extensible in a longitudinal direction and in a transverse direction, wherein the base sheet is a fabric and a first fabric surface and the containment flap is a fabric to define a second fabric surface wherein the first fabric surface is joined with the second fabric surface, and wherein a peak load of the base sheet in the transverse direction and in the longitudinal direction is between about 10,000 grams force and about 30,000 grams force;
   wherein the fluid-impervious pouch defines a pouch floor having a first end section, a second end section, and a central section extending between the first end section and the second end section, wherein the first end section defines a maximum width, the second end section defines a maximum width equal to the maximum width of the first end section, and the central section defines a maximum width that is less than 70% the maximum width of the first and second end sections.

11. The permanently closed containment pant of claim 10 wherein the first transition is made of a first material, the second transition is made of the same first material, and the chassis is made of the same first material, wherein the first material is 75-98% cotton and 2-25% spandex, the base sheet is a polyester fabric laminated with polyurethane, and the containment flap is a polyester fabric laminated with polyurethane.

12. The permanently closed containment pant of claim 10 wherein the sling further comprises the first transition and the second transition that are elastically extensible in a longitudinal direction and in a transverse direction.

13. The permanently closed containment pant of claim 12 wherein the base sheet is a woven polyester fabric laminated with a polyurethane sheet.

14. The permanently closed containment pant of claim 13 wherein the first transition is a discrete piece of material joined between the pouch and the waist elastic in the front waist region and wherein the second transition is a discrete piece of material joined between the pouch and the waist elastic in the back waist region.

15. The permanently closed containment pant of claim 13 wherein the chassis includes a shell material and wherein the first transition is an integral part of and a distinct projection of the shell material joined between the pouch and the waist elastic in the front waist region and wherein the second transition is a discrete piece of material joined between the pouch and the waist elastic in the back waist region.

16. A permanently closed containment pant comprising,
   an elastically extensible chassis defining a waist opening and a pair of leg openings, the chassis comprising a waist elastic joined proximate to and encircling the waist opening and a pair of leg elastics joined proximate to and encircling the leg openings, the waist opening defining a front waist region and a back waist region, wherein the chassis has a breathability of between about 10,000 and about 35,000 grams/(m$^2$-24 hours), and
   a sling comprising a fluid-impervious pouch joined between a first transition and a second transition, wherein the sling is joined with the waist elastic in the front waist region via the first transition and is joined with the waist elastic in the back waist region via the second transition, wherein the first transition and the second transition are elastically extensible in a transverse direction, wherein the fluid-impervious pouch comprises a polyester and polyurethane laminate, wherein the base sheet has a breathability of between about 500 and about 2500 grams/($m^2$-24 hours);

wherein the fluid-impervious pouch comprises a base sheet and a containment flap bonded to the base sheet wherein the base sheet is a polyester fabric laminated with polyurethane to define a polyurethane surface and a polyester fabric surface and the containment flap is a second polyester fabric laminated with polyurethane to define a second polyester fabric surface and a second polyurethane surface wherein the first polyurethane surface is joined with the second polyurethane surface via an ultrasonic bond, thermal bond, or pressure bond.

17. The permanently closed containment pant of claim 16 wherein the containment flap defines a proximal portion and a distal portion having a distal edge, wherein the proximal portion is joined with the base sheet and the distal portion includes a flap elastic folded over the distal edge of the flap, wherein the flap elastic defines a first tension zone, a second tension zone, and a third tension zone along a length of the containment flap, wherein the second tension zone is located between the first tension zone and the third tension zone and wherein the flap elastic has a greater tension in the second tension zone than in the first tension zone or the third tension zone.

18. The containment pant of claim 16 wherein the fluid-impervious pouch defines a pouch floor having a first end section, a second end section, and a central section extending between the first end section and the second end section, wherein the first end section defines a maximum width, the second end section defines a maximum width equal to the maximum width of the first end section, and the central section defines a maximum width that is less than 70% the maximum width of the first and second end sections.

* * * * *